(12) United States Patent
Mascioni et al.

(10) Patent No.: US 12,371,497 B2
(45) Date of Patent: Jul. 29, 2025

(54) ANTIGEN BINDING CONSTRUCTS TO CD4

(71) Applicant: ImaginAb, Inc., Inglewood, CA (US)

(72) Inventors: Alessandro Mascioni, Inglewood, CA (US); Daulet Satpayev, Inglewood, CA (US); Tove Olafsen, Inglewood, CA (US)

(73) Assignee: ImaginAb, Inc., Inglewood, CA (US)

( * ) Notice: Subject to any disclaimer, the term of this patent is extended or adjusted under 35 U.S.C. 154(b) by 1186 days.

(21) Appl. No.: 16/972,724

(22) PCT Filed: Jun. 5, 2019

(86) PCT No.: PCT/US2019/035550
§ 371 (c)(1),
(2) Date: Dec. 7, 2020

(87) PCT Pub. No.: WO2019/236684
PCT Pub. Date: Dec. 12, 2019

(65) Prior Publication Data
US 2021/0371527 A1    Dec. 2, 2021

Related U.S. Application Data

(60) Provisional application No. 62/682,339, filed on Jun. 8, 2018.

(51) Int. Cl.
*C07K 16/28* (2006.01)
*A61K 39/00* (2006.01)

(52) U.S. Cl.
CPC .... *C07K 16/2812* (2013.01); *A61K 2039/505* (2013.01); *C07K 2317/24* (2013.01); *C07K 2317/31* (2013.01); *C07K 2317/53* (2013.01); *C07K 2317/565* (2013.01); *C07K 2317/622* (2013.01); *C07K 2317/626* (2013.01)

(58) Field of Classification Search
USPC ...................................................... 424/133.1
See application file for complete search history.

(56) References Cited

U.S. PATENT DOCUMENTS

| | | | |
|---|---|---|---|
| 8,487,077 B2 | 7/2013 | Olma et al. | |
| 8,772,459 B2 | 7/2014 | Ho et al. | |
| 8,940,298 B2 | 1/2015 | Wu et al. | |
| 8,940,871 B2 | 1/2015 | Wu et al. | |
| 10,301,389 B2 | 5/2019 | Ho et al. | |
| 10,377,826 B2 | 8/2019 | Ho et al. | |
| 10,414,820 B2 | 9/2019 | Ho et al. | |
| 10,882,909 B2 | 1/2021 | Ho et al. | |
| 11,180,570 B2 | 11/2021 | Ho et al. | |
| 11,254,744 B2 | 2/2022 | Chan et al. | |
| 11,266,745 B2 | 3/2022 | Gudas et al. | |
| 2006/0257407 A1 | 11/2006 | Chen et al. | |
| 2014/0234215 A1 | 8/2014 | Ho et al. | |
| 2014/0271462 A1 | 9/2014 | Ho et al. | |
| 2017/0051044 A1 | 2/2017 | Chan et al. | |
| 2018/0051254 A1 | 2/2018 | Fricke et al. | |
| 2019/0262396 A1* | 8/2019 | Emmrich | A61K 35/15 |
| 2019/0382487 A1 | 12/2019 | Ho et al. | |
| 2019/0382488 A1 | 12/2019 | Ho et al. | |
| 2020/0140550 A1 | 5/2020 | Ho | |
| 2021/0371527 A1 | 12/2021 | Mascioni et al. | |
| 2022/0001043 A1 | 1/2022 | Wilson | |
| 2022/0089730 A1 | 3/2022 | Chan et al. | |
| 2022/0135698 A1 | 5/2022 | Ho | |
| 2023/0211024 A1 | 7/2023 | Mascioni et al. | |
| 2024/0390531 A1 | 11/2024 | Mascioni et al. | |

FOREIGN PATENT DOCUMENTS

| | | |
|---|---|---|
| WO | WO 12/072268 | 6/2012 |
| WO | WO 13/072406 | 5/2013 |
| WO | WO 13/072415 | 5/2013 |
| WO | WO 17/140735 | 8/2017 |

OTHER PUBLICATIONS

Examination Report dated Oct. 19, 2022 in patent application No. 19815887.5.
Freise et al., Dec. 13, 2016, ImmunoPET imaging of murine CD4+T cells using anti-CD4 cys-diabody: effects of protein dose on T cell function and imaging, Molecular Imaging & Biology, 19(4):599-609.
International Search Report and Written Opinion dated Oct. 4, 2019 in application No. PCT/US2019/035550.
Extended European Search Report dated Feb. 14, 2022 in patent application No. 19815887.5.

* cited by examiner

*Primary Examiner* — Janet L Epps-Smith
*Assistant Examiner* — Sarah A Alsomairy
(74) *Attorney, Agent, or Firm* — KNOBBE, MARTENS, OLSON & BEAR, LLP

(57) ABSTRACT

Antigen binding constructs that bind to CD4, for example antibodies, including antibody fragments (such as scFv, minibodies, and cys-diabodies) that bind to CD4, are described herein. Methods of use are described herein.

19 Claims, 21 Drawing Sheets

Specification includes a Sequence Listing.

FIGURE 3

CDR annotation (Chotia)

VH

MAX16H5 (mouse)      EVQLQQSGTVLARPGASVQMSCKASGYSFANYWMHWVKQRPGQGLQWIGALYPGNV       SEQ ID NO: 1
IAB41 (humanized)    QVQLVQSGAEVKKPGASVKVSCKASGYSFANYWMHWVRQAPGQRLEWIGALYPGNV       SEQ ID NO: 2

DTTYNQKFKDKAKLTAVTSASTAYMELSSLTNEDSAVYYCTRMGTTLEAPLDYWGQGTTLTVSS
                     DTTYNQKFQGRVTITRDTSASTAYMELSSLRSEDTAVYYCTRMGTTLEAPLDYWGQGTLVTVSS

VL

MAX16H5 (mouse)      QIVLTQSPAIMSASPGEKVAMTCSARSSVSYLYWYQQKPGSSPRLLIYDTSNLASGVP       SEQ ID NO: 3
IAB41 (humanized)    EIVLTQSPATLSLSPGERATLSCSARSSVSYLYWYQQKPGQAPRLLIYDTSNLASGIP       SEQ ID NO: 4

VRFIGSGSGTSYSLTISRMEAEDAATYYCQQWSDYPLTFGAGTKLELK
                     DRFSGSGSGTDFTLTISRLEPEDAAVYYCQQWSDYPLTFGGGTKLEIK

VL-VH EH3 hinge:
Signal peptide:
METDTLLLWVLLLWVPGSTG SEQ ID NO: 22
minibody:
EIVLTQSPATLSLSPGERATLSCSARSSVSYLYWYQQKPGQAPRLLIYDTSNLASGIPDRFSGSGSG
TDFTLTISRLEPEDAAVYYCQQWSDYPLTFGGGTKLEIKGSTSGGGSGGGGSGGGGSQVQLVQSGAE
VKKPGASVKVSCKASGYSFANYWMHWVRQAPGQRLEWIGALYPGNVDTTYNQKFQGRVTITRDTSAS
TAYMELSSLRSEDTAVYYCTRMGTTLEAPLDYWGQGTLVTVSSEPKSSDKTHTCPPCPPCGGGSSGG
GSGGQPREPQVYTLPPSREEMTKNQVSLTCLVKGFYPSDIAVEWESNGQPENNYKTTPPVLDSDGSF
FLYSKLTVDKSRWQQGNVFSCSVMHEALHNHYTQKSLSLSPG

SEQ ID NO: 5

FIGURE 4

VL-VH EH5 hinge:
Signal peptide: METDTLLLWVLLLWVPGSTG   SEQ ID NO: 23
minibody:

EIVLTQSPATLSLSPGERATLSCSARSSVSYLYWYQQKPGQAPRLLIYDTSNLASGIPDRFS    SEQ ID NO: 6
GSGSGTDFTLTISRLEPEDAAVYYCQQWSDYPLTFGGGTKLEIKGSTSGGGSGGGSGGGSS
QVQLVQSGAEVKKPGASVKVSCKASGYSFANYWMHWVRQAPGQRLEWIGALYPGNVDTTYNQ
KFQGRVTITRDTSASTAYMELSSLRSEDTAVYYCTRMGTTLEAPLDYWGQGTLVTVSSEPKS
SDKTHTCPPCPPCGGGSGGGSGGQPREPQVYTLPPSREEMTKNQVSLTCLVKGFYPSD
IAVEWESNGQPENNYKTTPPVLDSDGSFFLYSKLTVDKSRWQQGNVFSCSVMHEALHNHYTQ
KSLSLSPG

VH-VL EH3 hinge:

Signal peptide:
METDTLLLWVLLLWVPGSTG SEQ ID NO: 24 minibody:
QVQLVQSGAEVKKPGASVKVSCKASGYSFANYWMHWVRQAPGQRLEWIGALYPGNVDTTYNQ
KFQGRVTITRDTSASTAYMELSSLRSEDTAVYYCTRMGTTLEAPLDYWGQGTLVTVSSGSTS
GGGSGGGGSGGGGSSEIVLTQSPATLSLSPGERATLSCSARSSVSYLYWYQQKPGQAPRLLIY
DTSNLASGIPDRFSGSGSGTDFTLTISRLEPEDAAVYYCQQWSDYPLTFGGGTKLEIKEPKS
SDKTHTCPPCPPCGGSSGGGSGGQPREPQVYTLPPSREEMTKNQVSLTCLVKGFYPSDIAV
EWESNGQPENNYKTTPPVLDSDGSFFLYSKLTVDKSRWQQGNVFSCSVMHEALHNHYTQKSL
SLSPG                                                            SEQ ID NO: 7

FIGURE 7

VH-VL EH5 hinge:
Signal peptide:
METDTLLLWVLLLWVPGSTG SEQ ID NO: 25
minibody:
QVQLVQSGAEVKKPGASVKVSCKASGYSFANYWMHWVRQAPGQRLEWIGALYPGNVDTTYNQ
KFQGRVTITRDTSASTAYMELSSLRSEDTAVYYCTRMGTTLEAPLDYWGQTLVTVSSGSTS
GGGSGGGGSGGGGSSEIVLTQSPATLSLSPGERATLSCSARSSVSYLYWYQQKPGQAPRLLIY
DTSNLASGIPDRFSGSGSGTDFTLTISRLEPEDAAVYYCQQWSDYPLTFGGGTKLEIKEPKS
SDKTHTCPPCPPCGGGSGGGSGGGGQPREPQVYTLPPSREEMTKNQVSLTCLVKGFYPSD
IAVEWESNGQPENNYKTTPPVLDSDGSFFLYSKLTVDKSRWQQGNVFSCSVMHEALHNHYTQ
KSLSLSPG                                                      SEQ ID NO: 8

FIGURE 8

VL-VH EH3 hinge: SEQ ID NO: 9

```
ATGGAGACCGACACACTGCTGCTGTGGGTGCTGCTGCTGTGGGTGCCCGGAAGCACCGGAGAAA
TCGTGCTGACCCAGTCCCCTGCTACCCTGAGCCTGTCCCCTGGCGAAAGGGCCACACTGTCCTG
CTCCGGAGGCGTGAGCTATCTGTACTGGCTACCAACCTGGCCAGCAGAAGCCCGGACAGGCCCCTAGG
CTGCTGATCTACGACAGCAACAACCTGGCCAGCGGCATCCCTGACAGGTTCTCCGGCTCCGGCA
GCGGCACAGATTTCACCCTGACCATCTCCAGACTGGAGCCCGAAGACGCCGCCGTCTACTACTG
CCAGCAGTGGAGCGATTATCCTCTGACCTTCGGCGGCGGGACCAAGCTGGAGATCAAGGGCAGC
ACCAGCGGCGGCGAGGTGAAGAAGCCTGGGCGCGTGAAGGTGTCCTGTAAGGCTTCCGGCTA
CAGCTTCGCCAACTACTACCCGGATGCAACTGGGATACCAGCAACCTACCACCAACAGAAGTTCCAGGGCAGAGTCACCA
GGGCCCCTGTACCCCAGCAAGCGCCAGCGCCTTATATGGAGCTGTCCTCCCTCAGGAGCGAGGACAC
TTACCAGGACACAAGCGCCAGCACCGCCTTATATGGAGCTGTCCTCCCTCAGGAGCGAGGACAC
CGCCGTCTATTACTGCACCAGGATGGCACCACAGGATGGGCACCTGGACTATTGGGGCCAG
GGCACACTGGTGACAGTGTCCTCCCGAGCCCAAAAGCAGCGGATAAGACCCACACCTGCCCTCCTT
GCCCTCCTTGTGCCCCCCCCCCCCAGCAGGATCCAGCGAGGAAGCGGAGCCAACCAGGAACCTCAGGT
GTACACACTTCTACCCCGAGTCCCCAGCGACATCGCCGTGGAGTGGGAGAGCAACGGCCAGCCTGAGCCTGTCGTG
AAAGGCTTCTACCCAGCGACATCGCCGTGGAGTGGGAGAGCAACGGCCAGCCTGAGAAACAACT
ACAAAACCACCCCCCCCGTGCTGGACAGCGACGGCAGCTTCTTCCTCTACAGCAAGCTGACCGT
GGACAAGAGCAGATGGCAGCAGGGCAACGTGTTCTCCTGTTCCGTGATGCACGAGGCCCTCCAC
AACCACTACACCCAGAAATCCCCTGTCCCCTGTCCCCCGGCTGA
```

FIGURE 9

VH-VL EH3 hinge: SEQ ID NO: 10

ATGGAGACCGATACCCTCCTGCTCTGGGTGCTGCTGCTGTGGGTGCCTGGAAGCACAGGCCAGGTGCA
GCTGGTGCAGAGCGGAGCCGAGGTGAAAAAACCCGGCGAGTCTCCGTGAAGGTGAGCTGCAAGGCCAGCG
GCTACAGCTTCGCCAACTACTGGATGCACTGGGTGAGGCAGGCCCCTGGCCAGAGGCTGGAATGGATT
GGCGCCCTGTACCCTGGCGACCTGGACCACCTACAACCAGAAATTCCAGGGGTGACCATCAC
CAGAGATACCAGCAGCGCCAGCACCGCCTTACATGAACTGAGCAGCCTGAGGAGCGAGGATACCGCCGTGT
ACTACTGCACCAGGATGGGCAGCAGCACAAACCCTGGAGGCTCCCCTGATTACTGGGGCCACACTGGTG
ACAGTCAGCAGCGGCGGAGGCGGCAGCGGAGGAGGCGGCGAGAGACCTGGCGAGGAAGCAGCGA
GATCGTGCTGACCCAGAGTCCCCGCTACACTGGCCTCCCAGGCTCTGTCCTGCT
CCGCCAGAAGCTCCGTGAGCAACCTGGCCTCGGCCATTCCCGGACAGGTTCAGCGGCGTGTATTACTGCCAGCGGA
CTTCACCCCTGACCATCTCCAGACTCCGAGGATGCCGACAGTCTCGAGATCAAGGAGCCCAAATCCTCCGGCGGAACCG
ATTATCCTGACCTTTGGCGAGGGCACCAAGCTGGAGATCAAGCGGACCGTGGCTGCACCAGTCTCCGACCT
CACACCCTGCCCTCAGGTCTACACCCCCCCCGTGCTCTAGCCAGCCTCCAAGCAGCCAGTGACCAGCCTGACCT
AGAGCCTCAGTGGGCTTCTACCCCCCCCGTGCTCTGCAGGGCAGCCAGTCCAAGCCCCCAGCCCGAAAAC
GTCTGGTGAAGGGCACCCAGGATCCACCCGCCAGGCCGTCGAGTGGGAGTCCAATGGCAGTCAACTGCTGCTTTTCCCCTCTACTCCTCCAAGCTGGACCGT
AACTACAAAGTCCAGGTGCAGGGCAACGTGTTCAGCTGCAGCGTGATGCATGAGGCCCTCCACAACC
ACTACACCCAGAGAAATCCCTCTCCCCTGAGCCCCGGCTGA

FIGURE 10

VL-VH E1 terminal:

Signal peptide:
METDTLLLWVLLLWVPGSTG   SEQ ID NO: 26

Cys-Diabody:
EIVLTQSPATLSLSPGERATLSCSARSSVSYLYWYQQKPGQAPRLLIYDTSNLASGIPDRF
SGSGSGTDFTLTISRLEPEDAAVYYCQQWSDYPLTFGGGTKLEIKSGGGGQVQLVQSGAEV
KKPGASVKVSCKASGYSFANYWMHWVRQAPGQRLEWIGALYPGNVDTTYNQKFQGRVTITR
DTSASTAYMELSSLRSEDTAVYYCTRMGTTLEAPLDYWGQGTLVTVSSGGC   SEQ ID NO: 11

FIGURE 11

VL-VH E2 terminal:

Signal peptide:
METDTLLLWVLLLWVPGSTG   SEQ ID NO: 27

Cys-Diabody:
EIVLTQSPATLSLSPGERAT

FIGURE 12

VL-VH E3 terminal:
Signal peptide:
METDTLLLWVLLLWVPGSTG  SEQ ID NO: 28

Cys-Diabody:
EIVLTQSPATLSLSPGERATLSCSARSSVSYLYWYQQKPGQAPRLLIYDTSNLASGIPDR   SEQ ID NO: 13
FSGSGSGTDFTLTISRLEPEDAAVYYCQQWSDYPLTFGGGTKLEIKSGGGGQVQLVQSGA
EVKKPGASVKVSCKASGYSFANYWMHWVRQAPGQRLEWIGALYPGNVDTTYNQKFQGRVT
ITRDTSASTAYMELSSLRSEDTAVYYCTRMGTTLEAPLDYWGQGTLVTVSSGGCPPCPPC

FIGURE 13

VL-VH E4 terminal:
Signal peptide:
METDTLLLWVLLLWVPGSTG  SEQ ID NO: 29
Cys-Diabody:
EIVLTQSPATLSLSPGERATLSCSARSSVSYLYWYQQKPGQAPRLLIYDTSNLASGIPDRF
SGSGSGTDFTLTISRLEPEDAAVYYCQQWSDYPLTFGGGTKLEIKSGGGGQVQLVQSGAEV
KKPGASVKVSCKASGYSFANYWMHWVRQAPGQRLEWIGALYPGNVDTTYNQKFQGRVTITR
DTSASTAYMELSSLRSEDTAVYYCTRMGTTLEAPLDYWGQGTLVTVSSGGCPPCPPCPPC  SEQ ID NO: 14

FIGURE 14

VH-VL E1 terminal:
Signal peptide:
METDTLLLWVLLLLWVPGSTG    SEQ ID NO: 30

Cys-Diabody:
QVQLVQSGAEVKKPGASVKVSCKASGYSFANYWMHWVRQAPGQRLEWIGALYPGNVDTTYN
QKFQGRVTITRDTSASTAYMELSSLRSEDTAVYYCTRMGTTLEAPLDYWGQGTLVTVSSSG    SEQ ID NO: 15
GGGEIVLTQSPATLSLSPGERATLSCSARSSVSYLYWYQQKPGQAPRLLIYDTSNLASGIP
DRFSGSGSGTDFTLTISRLEPEDAAVYYCQQWSDYPLTFGGGTKLEIKGGC

FIGURE 15

VH-VL E2 terminal:
Signal peptide:
METDTLLLWVLLLWVPGSTG  SEQ ID NO: 31

Cys-Diabody:
QVQLVQSGAEVKKPGASVKVSCKASGYSFANYWMHWVRQAPGQRLEWIGALYPGNVDTTY　　SEQ ID NO: 16
NQKFQGRVTITRDTSASTAYMELSSLRSEDTAVYYCTRMGTTLEAPLDYWGQGTLVTVSS
SGGGGEIVLTQSPATLSLSPGERATLSCSARSSVSYLYWYQQKPGQAPRLLIYDTSNLAS
GIPDRFSGSGSGTDFTLTISRLEPEDAAVYYCQQWSDYPLTFGGGTKLEIKGGCPPC

VH-VL E3 terminal:
Signal peptide:
METDTLLLWVLLLWVPGSTG   SEQ ID NO: 32

Cys-Diabody:
QVQLVQSGAEVKKPGASVKVSCKASGYSFANYWMHWVRQAPGQRLEWIGALYPGNVDTTY
NQKFQGRVTITRDTSASTAYMELSSLRSEDTAVYYCTRMGTTLEAPLDYWGQGTLVTVSS
SGGGEIVLTQSPATLSLSPGERATLSCSARSSVSYLYWYQQKPGQAPRLLIYDTSNLAS
GIPDRFSGSGSGTDFTLTISRLEPEDAAVYYCQQWSDYPLTFGGGTKLEIKGGCPPCPPC   SEQ ID NO: 17

VH-VL E4 terminal:
Signal peptide:
METDTLLLWVLLLWVPGSTG    SEQ ID NO: 33

Cys-Diabody:
QVQLVQSGAEVKKPGASVKVSCKASGYSFANYWMHWVRQAPGQRLEWIGALYPGNVDTTY    SEQ ID NO: 18
NQKFQGRVTITRDTSASTAYMELSSLRSEDTAVYYCTRMGTTLEAPLDYWGQGTLVTVSS
SGGGGEIVLTQSPATLSLSPGERATLSCSARSSVSYLYWYQQKPGQAPRLLIYDTSNLAS
GIPDRFSGSGSGTDFTLTISRLEPEDAAVYYCQQWSDYPLTFGGGTKLEIKGGCPPCPPC
PPC

FIGURE 18

VL-VH EH3 hinge: EPKSSDKTHT  CPPCPPC     GGGSSGGGSGG    SEQ ID NO: 34

VL-VH EH5 hinge: EPKSSDKTHT  CPPCPPPCPPC GGGSSGGGSGG    SEQ ID NO: 35

VH-VL EH3 hinge: EPKSSDKTHT  CPPCPPC     GGGSSGGGSGG    SEQ ID NO: 36

VH-VL EH5 hinge: EPKSSDKTHT  CPPCPPPCPPC GGGSSGGGSGG    SEQ ID NO: 37

FIGURE 19

Heavy Chain:

```
                    1         2         3         4         5         6
                    0         0         0         0         0         0
                    .....|....|....|....|....|....|....|....|....|....|....|....|
IMGT                                           xxxxxxx                     xxxxxxx
Chotia                                         xxxxxxx                      xxxxxx
Kabat                                              xxxx                 xxxxxxxxxxx
North                                 xxxxxxxxxxxxxxxxx                xxxxxxxxxxxx-
MAX16H5 (mouse)     EVQLQQSGTVLARPGASVQMSCKASGYSFANYWMHWVKQRPGQGLQWIGALYPGNVDTTYNQ
Chotia              QVQLVQSGAEVKKPGASVKVSCKASGYTFTSYAMHWVRQAPGQRLEWMGWINAGNGNTKYSQ
Human Germline      QVQLVQSGAEVKKPGASVKVSCKASGYSFANYWMHWVRQAPGQRLEWMGWIGALYPGNVDTTYNQ
IAB41 (Humanized)
```

```
                    7         8         9         1         1         1
                    0         0         0         0         1         2
                                                  0         0         0
                    .....|....|....|....|....|....|....|....|....|....|....|....|
IMGT                                             xxxxxxxxxx
Chotia                                           xxxxxxxxxx
Kabat                                            xxxxxxxxxx
North               xxxx
MAX16H5 (mouse)     KFKDKAKLTAVTSASTAYMELSSLINEDSAVYYCTRMGTTLEAPLDYWGQGTTLTVSS    SEQ ID NO: 38
Human Germline      KFQGRVTITRDTSASTAYMELSSLRSEDTAVYYCAR......YFDYWGQGTLVTVSS     SEQ ID NO: 39
IAB41 (Humanized)   KFQGRVTITRDTSASTAYMELSSLRSEDTAVYYCTRMGTTLEAPLDYWGQGTLVTVSS    SEQ ID NO: 40
```

Heavy chain germline: IGHV1-3*01 + IGHJ4*01

FIGURE 20

```
Light Chain:
IMGT                    -----------------------------------xxxxx---------------xxxxxxxxxxx---------xxx----------
Chotia                  -----------------------------------xxxxxxxxxxx---------xxxxxxxxxx---------xxxxxxx-------
Kabat                   --------------------------------------xxxxxxxxxxxx-----xxxxxxxxx----------xxxxxxx-------
North                   ----------------------------------------xxxxxxxxxxxxx--xxxxxxxxxxxxx------xxxxxxxxxx----
MAX16H5 (mouse)         QIVLTQSPAIMSASPGEKVAMTCSARSSVSYLYWYQQKPGSSPRLLIYDTSNLASGVPVR
Human Germline          EIVLTQSPATLSLSPGERATLSC..........WYQQKPGLAPRLLIY......GIPDR
IAB41 (Humanized)       EIVLTQSPATLSLSPGERATLSC SARSSVSYLYWYQQKPGQAPRLLIYDTSNLASGIPDR
                        .........1.........2.........3.........4.........5.........6
                        0         0         0         0         0         0

IMGT                    ------------------xxxxxxxxxx--------------------
Chotia                  ------------------xxxxxxxxxx--------------------
Kabat                   ------------------xxxxxxxxxx--------------------
North                   -----------------xxxxxxxxxxxx-------------------
MAX16H5 (mouse)         FIGSGSGTSYSLTISRMEAEDAATYCQQWSDYPLTFGAGTKLELK    SEQ ID NO: 41
Human Germline          FSGSGSGTDFTLTISRLEPEDFAVYYC......FGQGTKLEIK      SEQ ID NO: 42
IAB41 (Humanized)       FSGSGSGTDFTLTISRLEPEDAAVYYCQQWSDYPLTFGQGTKLEIK   SEQ ID NO: 43
                        .........7.........8.........9.........1
                        0         0         0         0

Light chain germline: IGKV3D-20*01 + IGKJ2*01
```

FIGURE 21

KKVVLGKKGDTVELTCTASQKKSIQFHWKNSNQIK
ILGNQGSFLTKGPSKLNDRADSRRSLWDQGNFPLIIKNLKIEDSDTYICEVEDQKEEVQL
LVFGLTANSDTHLLQGQSLTLTLESPPGSSPSVQCRSPRGKNIQGGKTLSVSQLELQDSG
TWTCTVLQNQKKVEFKIDIVVLAFQKASSIVYKKEGEQVEFSFPLAFTVEKLTGSGELWW
QAERASSSKSWITFDLKNKEVSVKRVTQDPKLQMGKKLPLHLTLPQALPQYAGSGNLTLA
LEAKTGKLHQEVNLVVMRATQLQKNLTCEVWGPTSPKLMLSLKLENKEAKVSKREKAVWV
LNPEAGMWQCLLSDSGQVLLESNIKVLPTWSTPVQPMALIVLGGVAGLLLFIGLGIFFCV
RCRHRRRQAERMSQIKRLLSEKKTCQCPHRFQKTCSPI (SEQ ID NO: 44)

ANTIGEN BINDING CONSTRUCTS TO CD4

CROSS-REFERENCE TO RELATED APPLICATIONS

The present application is a U.S. national phase entry under 35 U.S.C. § 371 of International Application No. PCT/US2019/035550, filed Jun. 5, 2019, which claims the benefit of U.S. Provisional Application No. 62/682,339, filed Jun. 8, 2018, each of which is hereby incorporated by reference in its entirety.

FIELD

Embodiments described herein relate generally to antigen binding constructs, such as antibodies and fragments thereof, including minibodies, cys-diabodies, scFv, etc., that bind to CD4, as well as methods for their use.

REFERENCE TO SEQUENCE LISTING

The present application is being filed along with a Sequence Listing in electronic format. The Sequence Listing is provided as a file entitled IGNAB048WOSEQUENCELIST.TXT, which was created and last modified on Jun. 4, 2019, which is 65,910 bytes in size, and is replaced by a Substitute Sequence Listing provided as a file entitled IGNAB048_REPLACEMENTSEQLIST.txt, which was created and last modified on Aug. 5, 2024, which is 69,073 bytes in size. The information in the electronic Sequence Listing is hereby incorporated by reference in its entirety.

BACKGROUND

CD4 (cluster of differentiation 4) is a membrane glycoprotein which is a specific marker for a subclass of T-cells. CD4 acts as a co-receptor together with the T-cell receptor (TCR) to recognize antigen presentation by MHC Class II cells. CD4 functions to initiate or augment the early phase of T-cell activation.

SUMMARY

Some embodiments provided herein relate to antigen binding constructs, such as antibodies, including antibody fragments, that include a HCDR1 of the HCDR1 in SEQ ID NO: 2; a HCDR2 of the HCDR2 in SEQ ID NO: 2; a HCDR3 of the HCDR3 in SEQ ID NO: 2; a LCDR1 of the LCDR1 in SEQ ID NO: 4; a LCDR2 of the LCDR2 in SEQ ID NO: 4; and a LCDR3 of the LCDR3 in SEQ ID NO: 4. In some embodiments, the antigen binding constructs also include one or more of the point mutations or residues in one or more of the framework regions provided herein.

Some embodiments provided herein relate to antigen binding constructs, such as antibodies, including antibody fragments, that include a HCDR1 of the HCDR1 in SEQ ID NO: 2; a HCDR2 of the HCDR2 in SEQ ID NO: 2; a HCDR3 of the HCDR3 in SEQ ID NO: 2; a LCDR1 of the LCDR1 in SEQ ID NO: 4; a LCDR2 of the LCDR2 in SEQ ID NO: 4; a LCDR3 of the LCDR3 in SEQ ID NO: 4; and at least one VH framework residue selected from the group consisting of: a Glutamine at position 1 of the sequence in SEQ ID NO: 2; a Valine at position 5 of the sequence in SEQ ID NO: 2; an Alanine at position 9 of the sequence in SEQ ID NO: 2; a Valine at position 11 of the sequence in SEQ ID NO: 2; a Lysine at position 13 of the sequence in SEQ ID NO: 2; an Arginine at position 44 of the sequence in SEQ ID NO: 2; a Glutamic acid at position 46 of the sequence in SEQ ID NO: 2; a Glutamine at position 65 of the sequence in SEQ ID NO: 2; a Glycine at position 66 of the sequence in SEQ ID NO: 2; an Arginine at position 67 of the sequence in SEQ ID NO: 2; a Valine at position 68 of the sequence in SEQ ID NO: 2; a Threonine at position 69 of the sequence of SEQ ID NO: 2; an Arginine at position 87 of the sequence in SEQ ID NO: 2; a Serine at position 88 of the sequence in SEQ ID NO: 2.

Some embodiments provided herein relate to antigen binding constructs, such as antibodies, including antibody fragments, that include a HCDR1 of the HCDR1 in SEQ ID NO: 2; a HCDR2 of the HCDR2 in SEQ ID NO: 2; a HCDR3 of the HCDR3 in SEQ ID NO: 2; a LCDR1 of the LCDR1 in SEQ ID NO: 4; a LCDR2 of the LCDR2 in SEQ ID NO: 4; a LCDR3 of the LCDR3 in SEQ ID NO: 4; and at least one VL framework residue selected from the group consisting of: a Glutamic acid at position 1 of the sequence in SEQ ID NO: 4; a Leucine at position 13 of the sequence in SEQ ID NO: 4; an Arginine at position 18 of the sequence in SEQ ID NO: 4; a Threonine at position 20 of the sequence in SEQ ID NO: 4; a Leucine at position 21 of the sequence in SEQ ID NO: 4; a Serine at position 22 of the sequence in SEQ ID NO: 4; a Glutamine at position 41 of the sequence in SEQ ID NO: 4; an Alanine at position 42 of the sequence in SEQ ID NO: 4; an Isoleucine at position 57 of the sequence in SEQ ID NO: 4; an Aspartic acid at position 59 of the sequence in SEQ ID NO: 4; a Phenylalanine at position 70 of the sequence in SEQ ID NO: 4; a Threonine at position 71 of the sequence in SEQ ID NO: 4; a Leucine at position 77 of the sequence in SEQ ID NO: 4; a Proline at position 79 of the sequence in SEQ ID NO: 4; a Valine at position 84 of the sequence in SEQ ID NO: 4; and a Glycine at position 99 of the sequence in SEQ ID NO: 4.

Some embodiments provided herein relate to antigen binding constructs, such as antibodies, including antibody fragments, that include a HCDR1 of the HCDR1 in SEQ ID NO: 2; a HCDR2 of the HCDR2 in SEQ ID NO: 2; a HCDR3 of the HCDR3 in SEQ ID NO: 2; a LCDR1 of the LCDR1 in SEQ ID NO: 4; a LCDR2 of the LCDR2 in SEQ ID NO: 4; a LCDR3 of the LCDR3 in SEQ ID NO: 4; at least one VH framework residue selected from the group consisting of: a Glutamine at position 1 of the sequence in SEQ ID NO: 2; a Valine at position 5 of the sequence in SEQ ID NO: 2; an Alanine at position 9 of the sequence in SEQ ID NO: 2; a Valine at position 11 of the sequence in SEQ ID NO: 2; a Lysine at position 13 of the sequence in SEQ ID NO: 2; an Arginine at position 44 of the sequence in SEQ ID NO: 2; a Glutamic acid at position 46 of the sequence in SEQ ID NO: 2; a Glutamine at position 65 of the sequence in SEQ ID NO: 2; a Glycine at position 66 of the sequence in SEQ ID NO: 2; an Arginine at position 67 of the sequence in SEQ ID NO: 2; a Valine at position 68 of the sequence in SEQ ID NO: 2; a Threonine at position 69 of the sequence of SEQ ID NO: 2; an Arginine at position 87 of the sequence in SEQ ID NO: 2; a Serine at position 88 of the sequence in SEQ ID NO: 2; and at least one VL framework residue selected from the group consisting of: a Glutamic acid at position 1 of the sequence in SEQ ID NO: 4; a Leucine at position 13 of the sequence in SEQ ID NO: 4; an Arginine at position 18 of the sequence in SEQ ID NO: 4; a Threonine at position 20 of the sequence in SEQ ID NO: 4; a Leucine at position 21 of the sequence in SEQ ID NO: 4; a Serine at position 22 of the sequence in SEQ ID NO: 4; a Glutamine at position 41 of the sequence in SEQ ID NO: 4; an Alanine at position 42 of the sequence in SEQ ID NO: 4; an Isoleucine at position 57 of the sequence in SEQ ID NO: 4; an Aspartic acid at position 59 of the sequence in SEQ ID NO: 4; a Phenylalanine at position 70 of the sequence in SEQ ID NO: 4; a Threonine at position 71 of the sequence in SEQ ID NO: 4; a Leucine at position 77 of the sequence in SEQ ID NO: 4; a Proline at position 79 of the sequence in SEQ ID NO: 4; a Valine at position 84 of the sequence in SEQ ID NO: 4; and a Glycine at position 99 of the sequence in SEQ ID NO: 4.

In some embodiments, the antigen binding construct binds specifically to CD4. In some embodiments, the antigen binding construct depletes CD4 T-cells. In some embodiments, the antigen binding construct includes a detectable marker as described herein. In some embodiments, the antigen binding construct includes a therapeutic agent as described herein.

Some embodiments provided herein relate to antigen binding constructs, such as antibodies, including antibody fragments, that include a variable heavy domain (VH), wherein the VH comprises the amino acid sequence in SEQ ID NO: 2.

Some embodiments provided herein relate to antigen binding constructs, such as antibodies, including antibody fragments, that include a variable light domain (VL), wherein the VL comprises the amino acid sequence in SEQ ID NO: 4.

Some embodiments provided herein relate to antigen binding constructs, such as antibodies, including antibody fragments, that include a variable heavy domain (VH) of SEQ ID NO: 2; and a variable light domain (VL), of SEQ ID NO: 4.

Some embodiments provided herein relate to antigen binding constructs, such as antibodies, including antibody fragments, wherein the antigen binding construct is a full-length antibody.

Some embodiments provided herein relate to a humanized minibody that binds to CD4. In some embodiments, the minibody may comprise the amino acid sequence in SEQ ID NO: 5, 6, 7, or 8. Some embodiments provided herein relate to a nucleic acid sequence encoding an antigen binding construct as described herein, for example a CD4 antibody or antibody fragment. In some embodiments, the nucleic acid sequence comprises the nucleic acid sequence in SEQ ID NO: 9 or 10 (as shown in FIG. 9 or 10).

Some embodiments provided herein relate to a humanized cys-diabody that binds to CD4. In some embodiments, the humanized cys-diabody comprises the amino acid sequence in SEQ ID NO: 11, 12, 13, 14, 15, 16, 17, or 18. In some embodiments, the cys-diabody can comprise a variable heavy domain (VH) and a variable light domain (VL), wherein from N terminus to C terminus, is VH, VL. In some embodiments, the cys-diabody can comprise a variable heavy domain (VH) and a variable light domain (VL), wherein from N terminus to C terminus, is VL, VH.

In some embodiments, the antigen binding constructs can comprise a hinge region. In some embodiments, the hinge region can comprise the amino acid sequence in SEQ ID NO: 34, 35, 36, and/or 37.

Some embodiments herein relate to antigen binding constructs, such as antibodies, including antibody fragments, wherein the antigen binding construct comprises a polypeptide that comprises a single-chain variable fragment (scFv) comprising a variable heavy domain (VH) linked to a variable light domain (VL). In some embodiments, the antigen binding construct is a minibody or a diabody.

Some embodiments provided herein relate to antigen binding constructs, such as antibodies, including antibody fragments, that include at least 2 of: a Glutamine at position 1 of the sequence in SEQ ID NO: 2; a Valine at position 5 of the sequence in SEQ ID NO: 2; an Alanine at position 9 of the sequence in SEQ ID NO: 2; a Valine at position 11 of the sequence in SEQ ID NO: 2; a Lysine at position 13 of the sequence in SEQ ID NO: 2; an Arginine at position 44 of the sequence in SEQ ID NO: 2; a Glutamic acid at position 46 of the sequence in SEQ ID NO: 2; a Glutamine at position 65 of the sequence in SEQ ID NO: 2; a Glycine at position 66 of the sequence in SEQ ID NO: 2; an Arginine at position 67 of the sequence in SEQ ID NO: 2; a Valine at position 68 of the sequence in SEQ ID NO: 2; a Threonine at position 69 of the sequence of SEQ ID NO: 2; an Arginine at position 87 of the sequence in SEQ ID NO: 2; a Serine at position 88 of the sequence in SEQ ID NO: 2; a Glutamic acid at position 1 of the sequence in SEQ ID NO: 4; a Leucine at position 13 of the sequence in SEQ ID NO: 4; an Arginine at position 18 of the sequence in SEQ ID NO: 4; a Threonine at position 20 of the sequence in SEQ ID NO: 4; a Leucine at position 21 of the sequence in SEQ ID NO: 4; a Serine at position 22 of the sequence in SEQ ID NO: 4; a Glutamine at position 41 of the sequence in SEQ ID NO: 4; an Alanine at position 42 of the sequence in SEQ ID NO: 4; an Isoleucine at position 57 of the sequence in SEQ ID NO: 4; an Aspartic acid at position 59 of the sequence in SEQ ID NO: 4; a Phenylalanine at position 70 of the sequence in SEQ ID NO: 4; a Threonine at position 71 of the sequence in SEQ ID NO: 4; a Leucine at position 77 of the sequence in SEQ ID NO: 4; a Proline at position 79 of the sequence in SEQ ID NO: 4; a Valine at position 84 of the sequence in SEQ ID NO: 4; a Glycine at position 99 of the sequence in SEQ ID NO: 4.

Some embodiments provided herein relate to antigen binding constructs, such as antibodies, including antibody fragments, that include at least 3 of: a Glutamine at position 1 of the sequence in SEQ ID NO: 2; a Valine at position 5 of the sequence in SEQ ID NO: 2; an Alanine at position 9 of the sequence in SEQ ID NO: 2; a Valine at position 11 of the sequence in SEQ ID NO: 2; a Lysine at position 13 of the sequence in SEQ ID NO: 2; an Arginine at position 44 of the sequence in SEQ ID NO: 2; a Glutamic acid at position 46 of the sequence in SEQ ID NO: 2; a Glutamine at position 65 of the sequence in SEQ ID NO: 2; a Glycine at position 66 of the sequence in SEQ ID NO: 2; an Arginine at position 67 of the sequence in SEQ ID NO: 2; a Valine at position 68 of the sequence in SEQ ID NO: 2; a Threonine at position 69 of the sequence of SEQ ID NO: 2; an Arginine at position 87 of the sequence in SEQ ID NO: 2; a Serine at position 88 of the sequence in SEQ ID NO: 2; a Glutamic acid at position 1 of the sequence in SEQ ID NO: 4; a Leucine at position 13 of the sequence in SEQ ID NO: 4; an Arginine at position 18 of the sequence in SEQ ID NO: 4; a Threonine at position 20 of the sequence in SEQ ID NO: 4; a Leucine at position 21 of the sequence in SEQ ID NO: 4; a Serine at position 22 of the sequence in SEQ ID NO: 4; a Glutamine at position 41 of the sequence in SEQ ID NO: 4; an Alanine at position 42 of the sequence in SEQ ID NO: 4; an Isoleucine at position 57 of the sequence in SEQ ID NO: 4; an Aspartic acid at position 59 of the sequence in SEQ ID NO: 4; a Phenylalanine at position 70 of the sequence in SEQ ID NO: 4; a Threonine at position 71 of the sequence in SEQ ID NO: 4; a Leucine at position 77 of the sequence in SEQ ID NO: 4; a Proline at position 79 of the sequence in SEQ ID NO: 4; a Valine at position 84 of the sequence in SEQ ID NO: 4; a Glycine at position 99 of the sequence in SEQ ID NO: 4.

Some embodiments provided herein relate to antigen binding constructs, such as antibodies, including antibody fragments, that include all of: a Glutamine at position 1 of the sequence in SEQ ID NO: 2; a Valine at position 5 of the sequence in SEQ ID NO: 2; an Alanine at position 9 of the sequence in SEQ ID NO: 2; a Valine at position 11 of the sequence in SEQ ID NO: 2; a Lysine at position 13 of the sequence in SEQ ID NO: 2; an Arginine at position 44 of the sequence in SEQ ID NO: 2; a Glutamic acid at position 46 of the sequence in SEQ ID NO: 2; a Glutamine at position 65 of the sequence in SEQ ID NO: 2; a Glycine at position 66 of the sequence in SEQ ID NO: 2; an Arginine at position 67 of the sequence in SEQ ID NO: 2; a Valine at position 68 of the sequence in SEQ ID NO: 2; a Threonine at position 69 of the sequence of SEQ ID NO: 2; an Arginine at position 87 of the sequence in SEQ ID NO: 2; a Serine at position 88 of the sequence in SEQ ID NO: 2; a Glutamic acid at position 1 of the sequence in SEQ ID NO: 4; a Leucine at position 13 of the sequence in SEQ ID NO: 4; an Arginine at position 18 of the sequence in SEQ ID NO: 4; a Threonine at position 20 of the sequence in SEQ ID NO: 4; a Leucine at position 21 of the sequence in SEQ ID NO: 4; a Serine at position 22 of the sequence in SEQ ID NO: 4; a Glutamine at position 41 of the sequence in SEQ ID NO: 4; an Alanine at position 42 of the sequence in SEQ ID NO: 4; an Isoleucine at position 57 of the sequence in SEQ ID NO: 4; an Aspartic acid at position 59 of the sequence in SEQ ID NO: 4; a Phenylalanine at position 70 of the sequence in SEQ ID NO: 4; a Threonine at position 71 of the sequence in SEQ ID NO: 4; a Leucine at position 77 of the sequence in SEQ ID NO: 4; a Proline at position 79 of the sequence in SEQ ID NO: 4; a Valine at position 84 of the sequence in SEQ ID NO: 4; a Glycine at position 99 of the sequence in SEQ ID NO: 4.

In some aspects an antigen binding construct is provided that comprises: a HCDR1 of the HCDR1 in SEQ ID NO: 2; a HCDR2 of the HCDR2 in SEQ ID NO: 2; a HCDR3 of the HCDR3 in SEQ ID NO: 2; a LCDR1 of the LCDR1 in SEQ ID NO: 4; a LCDR2 of the LCDR2 in SEQ ID NO: 4; a LCDR3 of the LCDR3 in SEQ ID NO: 4; and at least one VH framework residue selected from the group consisting of: a Glutamine at position 1 of the sequence in SEQ ID NO: 2; a Valine at position 5 of the sequence in SEQ ID NO: 2; an Alanine at position 9 of the sequence in SEQ ID NO: 2; a Valine at position 11 of the sequence in SEQ ID NO: 2; a Lysine at position 13 of the sequence in SEQ ID NO: 2; an Arginine at position 44 of the sequence in SEQ ID NO: 2; a Glutamic acid at position 46 of the sequence in SEQ ID NO: 2; a Glutamine at position 65 of the sequence in SEQ ID NO: 2; a Glycine at position 66 of the sequence in SEQ ID NO: 2; an Arginine at position 67 of the sequence in SEQ ID NO: 2; a Valine at position 68 of the sequence in SEQ ID NO: 2; a Threonine at position 69 of the sequence of SEQ ID NO: 2; an Arginine at position 87 of the sequence in SEQ ID NO: 2; a Serine at position 88 of the sequence in SEQ ID NO: 2.

In some aspects, an antigen binding construct is provided that comprises: a HCDR1 of the HCDR1 in SEQ ID NO: 2; a HCDR2 of the HCDR2 in SEQ ID NO: 2; a HCDR3 of the HCDR3 in SEQ ID NO: 2; a LCDR1 of the LCDR1 in SEQ ID NO: 4; a LCDR2 of the LCDR2 in SEQ ID NO: 4; a LCDR3 of the LCDR3 in SEQ ID NO: 4; and at least one VL framework residue selected from the group consisting of: a Glutamic acid at position 1 of the sequence in SEQ ID NO: 4; a Leucine at position 13 of the sequence in SEQ ID NO: 4; an Arginine at position 18 of the sequence in SEQ ID NO: 4; a Threonine at position 20 of the sequence in SEQ ID NO: 4; a Leucine at position 21 of the sequence in SEQ ID NO: 4; a Serine at position 22 of the sequence in SEQ ID NO: 4; a Glutamine at position 41 of the sequence in SEQ ID NO: 4; an Alanine at position 42 of the sequence in SEQ ID NO: 4; an Isoleucine at position 57 of the sequence in SEQ ID NO: 4; an Aspartic acid at position 59 of the sequence in SEQ ID NO: 4; a Phenylalanine at position 70 of the sequence in SEQ ID NO: 4; a Threonine at position 71 of the sequence in SEQ ID NO: 4; a Leucine at position 77 of the sequence in SEQ ID NO: 4; a Proline at position 79 of the sequence in SEQ ID NO: 4; a Valine at position 84 of the sequence in SEQ ID NO: 4; a Glycine at position 99 of the sequence in SEQ ID NO: 4.

In some aspects, a nucleic acid sequence encoding the minibody provided herein is provided, the nucleic acid sequence comprises the nucleic acid sequence in SEQ ID NO: 9 or 10.

In some aspects, a minibody or cys-diabody is provided that comprises: a HCDR1 of the HCDR1 in SEQ ID NO: 2; a HCDR2 of the HCDR2 in SEQ ID NO: 2; a HCDR3 of the HCDR3 in SEQ ID NO: 2; a LCDR1 of the LCDR1 in SEQ ID NO: 4; a LCDR2 of the LCDR2 in SEQ ID NO: 4; a LCDR3 of the LCDR3 in SEQ ID NO: 4; and at least one of: a Glutamine at position 1 of the sequence in SEQ ID NO: 2; a Valine at position 2 of the sequence in SEQ ID NO: 2; a Leucine at position 4 of the sequence in SEQ ID NO: 2; an Alanine at position 24 of the sequence in SEQ ID NO: 2; a Serine at position 25 of the sequence in SEQ ID NO: 2; a Methionine at position 34 of the sequence in SEQ ID NO: 2; a Histidine at position 35 of the sequence in SEQ ID NO: 2; a Glutamic acid position 46 of the sequence in SEQ ID NO: 2; a Tryptophan at position 47 of the sequence in SEQ ID NO: 2; an Isoleucine at position 48 of the sequence in SEQ ID NO: 2; a Glycine at position 49 of the sequence in SEQ ID NO: 2; an Alanine at position 50 of the sequence in SEQ ID NO: 2; a Leucine at position 51 of the sequence in SEQ ID NO: 2; an Asparagine at position 61 of the sequence in SEQ ID NO: 2; a Phenylalanine at position 64 of the sequence in SEQ ID NO: 2; an Isoleucine at position 70 of the sequence in SEQ ID NO: 2; an Arginine at position 72 of the sequence in SEQ ID NO: 2; an Alanine at position 79 of the sequence in SEQ ID NO: 2; a Threonine at position 97 of the sequence in SEQ ID NO: 2; an Arginine at position 98 of the sequence in SEQ ID NO: 2; a Glutamic acid at position 1 of the sequence in SEQ ID NO: 4; an Isoleucine at position 2 of the sequence in SEQ ID NO: 4; a Leucine at position 4 of the sequence in SEQ ID NO: 4; a Glutamine at position 6 of the sequence in SEQ ID NO: 4; a Tryptophan at position 34 of the sequence in SEQ ID NO: 4; a Tyrosine at position 35 of the sequence in SEQ ID NO: 4; a Leucine at position 45 of the sequence in SEQ ID NO: 4; a Leucine at position 46 of the sequence in SEQ ID NO: 4; an Isoleucine at position 47 of the sequence in SEQ ID NO: 4; a Glycine at position 67 of the sequence in SEQ ID NO: 4; a Phenylalanine at position 70 of the sequence in SEQ ID NO: 4; a Phenylalanine at position 97 of the sequence in SEQ ID NO: 4.

In some aspects, an antigen binding construct is provided that comprises: a HCDR1 of the HCDR1 in SEQ ID NO: 2; a HCDR2 of the HCDR2 in SEQ ID NO: 2; a HCDR3 of the HCDR3 in SEQ ID NO: 2; a LCDR1 of the LCDR1 in SEQ ID NO: 4; a LCDR2 of the LCDR2 in SEQ ID NO: 4; a LCDR3 of the LCDR3 in SEQ ID NO: 4; and at least one of: a Glutamine at position 1 of the sequence in SEQ ID NO: 2; a Valine at position 20 of the sequence in SEQ ID NO: 2; an Arginine at position 38 of the sequence in SEQ ID NO: 2; an Alanine at position 40 of the sequence in SEQ ID NO: 2; an Arginine at position 44 of the sequence in SEQ ID NO: 2; a Tyrosine at position 60 of the sequence in SEQ ID NO:

2; a Valine at position 68 of the sequence in SEQ ID NO: 2; an Isoleucine at position 70 of the sequence in SEQ ID NO: 2; an Arginine at position 72 of the sequence in SEQ ID NO: 2; a Threonine at position 74 of the sequence in SEQ ID NO: 2; a Glutamic acid at position 1 of the sequence in SEQ ID NO: 4; a Leucine at position 11 of the sequence in SEQ ID NO: 4; a Leucine at position 13 of the sequence in SEQ ID NO: 4; an Alanine at position 19 of the sequence in SEQ ID NO: 4; a Leucine at position 21 of the sequence in SEQ ID NO: 4; an Isoleucine at position 57 of the sequence in SEQ ID NO: 4; a Phenylalanine at position 70 of the sequence in SEQ ID NO: 4; a Leucine at position 77 of the sequence in SEQ ID NO: 4; a Proline at position 79 of the sequence in SEQ ID NO: 4; a Valine at position 84 of the sequence in SEQ ID NO: 4; a Glycine at position 99 of the sequence in SEQ ID NO: 4.

In some aspects, an antigen binding construct is provided that comprises: a HCDR1 of the HCDR1 in SEQ ID NO: 2; a HCDR2 of the HCDR2 in SEQ ID NO: 2; a HCDR3 of the HCDR3 in SEQ ID NO: 2; a LCDR1 of the LCDR1 in SEQ ID NO: 4; a LCDR2 of the LCDR2 in SEQ ID NO: 4; a LCDR3 of the LCDR3 in SEQ ID NO: 4; and at least one of:
  a) a VH comprising at least one of: E1Q, Q5V, T9A, V10E, L11V, A12K, R13K, Q19K, M20V, K38R, R40A, Q46E, T59, N61, K65Q, D66G, K67R, A68V, K69T, L70I, A72R, V73D, T87R, N88S, S91T, T115L, or L116V;
  b) a VL comprising at least one of: Q1E, I10T, M11L, A13L, K18R, V19A, A20T, M21L, T22S, S41Q, S42A, V57I, V59D, I62S, S69D, Y70F, S71T, M77L, A79P, A82, T84V, A99G, or L106I;
  c) the VH of a) and the VL of b);
  d) any one of a), b), and c), wherein the VH is at least 80% identical to SEQ ID NO: 2;
  e) any one of a), b), and c), wherein the VL is at least 80% identical to SEQ ID NO: 4;
  f) any one of a), b), and c), wherein the VH is at least 80% identical to SEQ ID NO: 2; and any one of a), b), and c), wherein the VL is at least 80% identical to SEQ ID NO: 4;
  g) a VH with T59, N61, or both, wherein the VH is a humanized VH;
  h) a VL with A82, wherein the VL is a humanized VL;
  i) a VH according to g) and a VL according to h);
  j) a VH with Q46E;
  k) a VH with Q46E, wherein
    i) the VH is at least 80% identical to SEQ ID NO: 2
    ii) the VL is at least 80% identical to SEQ ID NO: 4
    iii) the VH is at least 80% identical to SEQ ID NO: 2 and the VL is at least 80% identical to SEQ ID NO: 4;
  l) a VH with at least one of T115L, L116V;
  m) a VL with at least one of S41Q, A99G, or L106I;
  n) a VH with at least one of T115L, L116V and a VL with at least one of S41Q, A99G, or L106I; or
  o) l), m), or n), wherein
    i) the VH is at least 80% identical to SEQ ID NO: 2
    ii) the VL is at least 80% identical to SEQ ID NO: 4
    iii) the VH is at least 80% identical to SEQ ID NO: 2 and the VL is at least 80% identical to SEQ ID NO: 4.

In some aspects, a humanized minibody that binds to human CD4 is provided, wherein the humanized minibody comprises: a HCDR1 of the HCDR1 in SEQ ID NO: 2; a HCDR2 of the HCDR2 in SEQ ID NO: 2; a HCDR3 of the HCDR3 in SEQ ID NO: 2; a LCDR1 of the LCDR1 in SEQ ID NO: 4; a LCDR2 of the LCDR2 in SEQ ID NO: 4; a LCDR3 of the LCDR3 in SEQ ID NO: 4; and at least one of:
  a) a VH with T59, N61, or both, wherein the VH is a humanized VH, wherein the VH is at least 80% identical to SEQ ID NO: 2, and a VL that is at least 80% identical to SEQ ID NO: 4;
  b) a VH and VL that is in the VL-VH orientation (amino to carboxyl);
  c) a VL with A99G;
  d) a VH with T59, N61, or both,
  e) a VL with A99G and ii) a VH with T59, N61, or both,
  f) a VH with T59, N61, or both, wherein the VH is a humanized VH, wherein the VH is at least 80% identical to SEQ ID NO: 2, and a VL that is at least 80% identical to SEQ ID NO: 4 and wherein the VL comprises A99G; or
  g) a VH comprising T59, N61, or both, wherein the VH is a humanized VH as numbered accord to the numbering of SEQ ID NO: 2, and A VL comprising A99G, as numbered accord to the numbering of SEQ ID NO: 4.

In some aspects, a method of treating a subject is provided that comprises providing a subject suffering from a CD4 related disorder; and administering an effective amount of the humanized minibody or the antigen binding construct or the minibody or the cys-diabody to the subject so as to reduce at least one symptom from the CD4 related disorder.

In some aspects, the use of the humanized minibody or the antigen binding construct, or the minibody or the cys-diabody is provided for the preparation of a medicament for the treatment of a CD4 related disorder.

In some aspects, the humanized minibody, or the antigen binding construct, or the minibody or the cys-diabody is provided for use as a medicament.

In some aspects, the humanized minibody, or the antigen binding construct, or the minibody or the cys-diabody is provided for use in at least one of: detection, diagnosis, surgery, staging, treatment, monitoring of treatment, monitoring of disease progression, and monitoring therapy.

In some aspects, the humanized minibody, or the antigen binding construct, or the minibody or the cys-diabody is provided for use in at least one of: detection, diagnosis, surgery, staging, treatment, monitoring of treatment, monitoring of disease progression, and monitoring therapy of a CD4 related disorder.

BRIEF DESCRIPTION OF THE DRAWINGS

FIG. 3 illustrates some embodiments of an anti-CD4 antigen binding construct VH and VL sequences. SEQ ID NO: 2 and 4 include the VH and VL sequences for IAB41-1 (and are both included in SEQ ID NO: 5).

FIG. 4 illustrates some embodiments of amino acid sequences for minibodies.

FIG. 5 illustrates some embodiments of amino acid sequences for minibodies.

FIG. 6 illustrates some embodiments of amino acid sequences for minibodies.

FIG. 7 illustrates some embodiments of amino acid sequences for minibodies.

FIG. 8 illustrates some embodiments of nucleic acid sequences encoding minibodies.

FIG. 9 illustrates some embodiments of nucleic acid sequences encoding minibodies.

FIG. 10 illustrates some embodiments of amino acid sequences for cys-diabodies.

FIG. 11 illustrates some embodiments of amino acid sequences for cys-diabodies.

FIG. 12 illustrates some embodiments of amino acid sequences for cys-diabodies.

FIG. 13 illustrates some embodiments of amino acid sequences for cys-diabodies.

FIG. 14 illustrates some embodiments of amino acid sequences for cys-diabodies.

FIG. 15 illustrates some embodiments of amino acid sequences for cys-diabodies.

FIG. 16 illustrates some embodiments of amino acid sequences for cys-diabodies.

FIG. 17 illustrates some embodiments of amino acid sequences for cys-diabodies.

FIG. 18 illustrates some embodiments for amino acid sequences for hinge regions of minibodies.

FIG. 19 provides an annotated sequence alignment of the heavy chain sequences of some of the antigen binding constructs provided herein. The X denotes the positions of various embodiments of CDRs, as denoted. Solid boxes mark extended CDR regions as defined by North B. et al, J Mol Biol 2011; 406:228-56. Underlined residues are CDR regions as defined by Chotia. The residues highlighted in darker shading are framework residues that are different between the mouse and humanized constructs.

FIG. 20 provides an annotated sequence alignment of the light chain sequences of some of the antigen binding constructs provided herein. The X denotes the positions of various embodiments of CDRs, as denoted. Solid boxes mark extended CDR regions as defined by North B. et al, J Mol Biol 2011; 406:228-56. Underlined residues are CDR regions as defined by Chotia. The X denotes the positions of various embodiments of CDRs, as denoted. The residues highlighted in darker shading are framework residues that are different between the mouse and humanized constructs.

FIG. 21 provides an amino acid sequence of human CD4.

DETAILED DESCRIPTION

Figure 1:
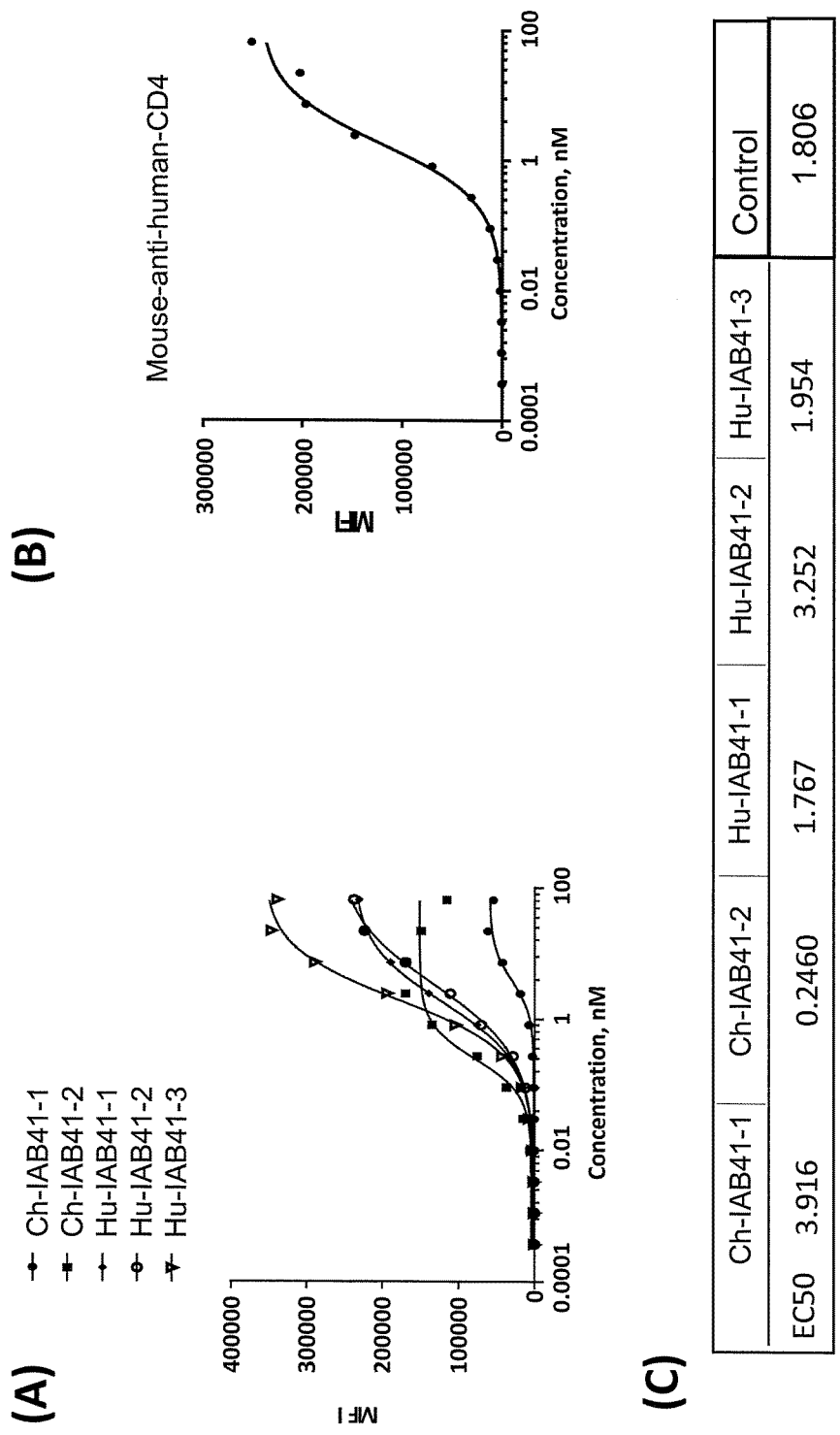
FIG. 1 depicts the results of a flow cytometry binding analysis of chimera and humanized IAB41 variants to HPB-ALL cells. SEQ ID NO: 5 is humanized IAB41-1 (Hu-IAB41-1).

Described herein are antigen binding constructs, including antibodies and fragments thereof, such as cys-diabodies and minibodies. In some embodiments, these constructs bind to CD4. Such antigen binding constructs can be useful for detecting the presence, localization, and/or quantities of the target molecule (CD4 and/or CD4+ cells, for example, certain classes of T-cells). Such antigen binding constructs can also be useful for targeting therapeutic agents to cells that express the target molecule. In some embodiments, the antigen binding constructs can be therapeutics as themselves (without the need for an additional payload). In some embodiments, methods are provided for detecting the presence or absence of the target molecule (or "target") using antigen binding constructs (including antibodies, and constructs such as cys-diabodies and/or minibodies). In some embodiments, methods are provided for using the antigen binding constructs for therapeutic purposes. The following definitions are provided for the context of the application.

Following these definitions and various embodiments, is a more detailed description of various embodiments.

Definitions and Various Embodiments

"Treating" or "treatment" of a condition may refer to preventing the condition, slowing the onset and/or rate of development of the condition, reducing the risk of developing the condition, preventing and/or delaying the development of symptoms associated with the condition, reducing or ending symptoms associated with the condition, generating a complete or partial regression of the condition, or some combination thereof. The term "prevent" does not require the absolute prohibition of the disorder or disease.

Any options or embodiments provided herein regarding treatment or treating can also be applied to the use of the compound in the preparation of a medicament for the treatment of the disorder.

A "therapeutically effective amount" or a "therapeutically effective dose" is an amount that produces a desired therapeutic effect in a subject, such as preventing, treating a target condition, delaying the onset of the disorder and/or symptoms, and/or alleviating symptoms associated with the condition. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and/or the route of administration. One skilled in the clinical and pharmacological arts will be able to determine a therapeutically effective amount through routine experimentation, for example by monitoring a subject's response to administration of a compound and adjusting the dosage accordingly, given the present disclosure. For additional guidance, see Remington: The Science and Practice of Pharmacy 21.sup.st Edition, Univ. of Sciences in Philadelphia (USIP), Lippincott Williams & Wilkins, Philadelphia, Pa., 2005.

The term "antigen binding construct" includes all varieties of antibodies, including binding fragments thereof, and including minibodies and/or diabodies and/or cys-diabodies. Further included are constructs that include 1, 2, 3, 4, 5, and/or 6 CDRs. In some embodiments, these CDRs can be distributed between their appropriate framework regions in a traditional antibody. In some embodiments, the CDRs can be contained within a heavy and/or light chain variable region. In some embodiments, the CDRs can be within a heavy chain and/or a light chain. In some embodiments, the CDRs can be within a single peptide chain. In some embodiments, the CDRs can be within two or more peptides that are covalently linked together. In some embodiments, they can be covalently linked together by a disulfide bond. In some embodiments, they can be linked via a linking molecule or moiety. In some embodiments, the antigen binding proteins are non-covalent, such as a diabody and a monovalent scFv. Unless otherwise denoted herein, the antigen binding constructs described herein bind to the noted target molecule. The term "target" or "target molecule" denotes the CD4 protein. Examples of CD4 proteins are known in the art. Any reference to antigen binding construct provided herein not only references the class of molecules as a genus, but also specifically contemplates any one or more of the species, in any combination, of constructs that fall within that class, e.g., minibodies, diabodies, cys-diabodies, antibodies, etc.

The term "antibody" includes, but is not limited to, genetically engineered or otherwise modified forms of immunoglobulins, such as intrabodies, chimeric antibodies, fully human antibodies, humanized antibodies, antibody fragments, and heteroconjugate antibodies (e.g., bispecific antibodies, diabodies, triabodies, tetrabodies, etc.). The term "antibody" includes cys-diabodies and minibodies. The term antibody includes engineered scFv, minibodies, fibronetic domains, nanobodies, affibodies, cyclic peptides, and cys-diabody antibody fragments. In some embodiments, these constructs are able to bind and specifically target human CD4.

Thus, each and every embodiment provided herein in regard to "antibodies" is also envisioned as cys-diabody and/or minibody embodiments, unless explicitly denoted otherwise. The term "antibody" includes a polypeptide of the immunoglobulin family or a polypeptide comprising fragments of an immunoglobulin that is capable of noncovalently, reversibly, and in a specific manner binding a corresponding antigen. An exemplary antibody structural unit comprises a tetramer. In some embodiments, a full length antibody can be composed of two identical pairs of polypeptide chains, each pair having one "light" and one "heavy" chain, connected through a disulfide bond. The recognized immunoglobulin genes include the kappa, lambda, alpha, gamma, delta, epsilon, and mu constant region genes, as well as the myriad immunoglobulin variable region genes. For full length chains, the light chains are classified as either kappa or lambda. For full length chains, the heavy chains are classified as gamma, mu, alpha, delta, or epsilon, which in turn define the immunoglobulin classes, IgG, IgM, IgA, IgD, and IgE, respectively. The N-terminus of each chain defines a variable region of about 100 to 110 or more amino acids primarily responsible for antigen recognition. The terms variable light chain (VL) and variable heavy chain (VH) refer to these regions of light and heavy chains respectively. As used in this application, an "antibody" encompasses all variations of antibody and fragments thereof. Thus, within the scope of this concept are full length antibodies, chimeric antibodies, humanized antibodies, single chain antibodies (scFv), Fab, Fab', and multimeric versions of these fragments (e.g., F(ab')2) with the same binding specificity. In some embodiments, the antibody binds specifically to a desired target.

"Complementarity-determining domains" or "complementarity-determining regions" ("CDRs") interchangeably refer to the hypervariable regions of VL and VH. The CDRs are the target protein-binding site of the antibody chains that harbors specificity for such target protein. In some embodiments, there are three CDRs (CDR1-3, numbered sequentially from the N-terminus) in each VL and/or VH, constituting about 15-20% of the variable domains. The CDRs are structurally complementary to the epitope of the target protein and are thus directly responsible for the binding specificity. The remaining stretches of the VL or VH, the so-called framework regions (FRs), exhibit less variation in amino acid sequence (Kuby, Immunology, 4th ed., Chapter 4. W.H. Freeman & Co., New York, 2000).

The positions of the CDRs and framework regions can be determined using various well known definitions in the art, e.g., Kabat definition (Wu, T. T., E. A. Kabat. 1970. An analysis of the sequences of the variable regions of Bence Jones proteins and myeloma light chains and their implications for antibody complementarity. J. Exp. Med. 132: 211-250; Kabat, E. A., Wu, T. T., Perry, H., Gottesman, K., and Foeller, C. (1991) Sequences of Proteins of Immunological Interest, 5th ed., NIH Publication No. 91-3242, Bethesda, MD); Chothia definition (Chothia and Lesk, J. Mol. Biol., 196:901-917 (1987); Chothia et al., Nature, 342:877-883 (1989); Chothia et al., J. Mol. Biol., 227:799-817 (1992); Al-Lazikani et al., J. Mol. Biol., 273:927-748 (1997)), ImMunoGeneTics database (IMGT) definition (on the worldwide web at imgt.org, Giudicelli, V., Duroux, P., Ginestoux, C., Folch, G., Jabado-Michaloud, J., Chaume, D. and Lefranc, M.-P. IMGT/LIGM-DB, the IMGT® comprehensive database of immunoglobulin and T cell receptor nucleotide sequences Nucl. Acids Res., 34, D781-D784 (2006), PMID: 16381979; Lefranc, M.-P., Pommié, C., Ruiz, M., Giudicelli, V., Foulquier, E., Truong, L., Thouvenin-Contet, V. and Lefranc, G., IMGT unique numbering for immunoglobulin and T cell receptor variable domains and Ig superfamily V-like domains Dev. Comp. Immunol., 27, 55-77 (2003). PMID: 12477501; Brochet, X., Lefranc, M.-P. and Giudicelli, V. IMGT/V-QUEST: the highly customized and integrated system for IG and TR standardized V-J and V-D-J sequence analysis Nucl. Acids Res, 36, W503-508 (2008)); AbM definition (Martin et al., Proc. Natl. Acad. Sci. USA, 86:9268-9272 (1989)); the contact definition (MacCallum et al., J. Mol. Biol., 262:732-745 (1996)); the automatic modeling and analysis tool Honegger A, and Plückthun A. (world wide web at bioc dot uzh dot ch/antibody/Numbering/index dot html); and the definition by North (North B, Lehmann A, Dunbrack R L. A New Clustering of Antibody CDR Loop Conformations. J Mol Biol 2011; 406:228-56). CDRs according to various definitions are provided within FIGS. 20 and 21.

The term "binding specificity determinant" or "BSD" interchangeably refer to the minimum contiguous or non-contiguous amino acid sequence within a complementarity determining region necessary for determining the binding specificity of an antibody. A minimum binding specificity determinant can be within one or more CDR sequences. In some embodiments, the minimum binding specificity determinants reside within (i.e., are determined solely by) a portion or the full-length of the CDR3 sequences of the heavy and light chains of the antibody. In some embodiments, CDR3 of the heavy chain variable region is sufficient for the antigen binding construct specificity.

An "antibody variable light chain" or an "antibody variable heavy chain" as used herein refers to a polypeptide comprising the VL or VH, respectively. The endogenous VL is encoded by the gene segments V (variable) and J (junctional), and the endogenous VH by V, D (diversity), and J. Each of VL or VH includes the CDRs as well as the framework regions. In this application, antibody variable light chains and/or antibody variable heavy chains may, from time to time, be collectively referred to as "antibody chains." These terms encompass antibody chains containing mutations that do not disrupt the basic structure of VL or VH, as one skilled in the art will readily recognize. In some embodiments, full length heavy and/or light chains are contemplated. In some embodiments, only the variable region of the heavy and/or light chains are contemplated as being present.

Antibodies can exist as intact immunoglobulins or as a number of fragments produced by digestion with various peptidases. Thus, for example, pepsin digests an antibody below the disulfide linkages in the hinge region to produce F(ab)'2, a dimer of Fab' which itself is a light chain (VL-CL) joined to VH-CH1 by a disulfide bond. The F(ab)'2 may be reduced under mild conditions to break the disulfide linkage in the hinge region, thereby converting the F(ab)'2 dimer into a Fab' monomer. The Fab' monomer is a Fab with part of the hinge region. (Paul, Fundamental Immunology 3d ed. (1993)). While various antibody fragments are defined in terms of the digestion of an intact antibody, one of skill will appreciate that such fragments may be synthesized de novo either chemically or by using recombinant DNA methodology. Thus, the term "antibody," as used herein, also includes antibody fragments either produced by the modification of whole antibodies, or those synthesized de novo using recombinant DNA methodologies (e.g., single chain Fv) or those identified using phage, yeast, or mammalian cell display libraries (see, e.g., McCafferty et al., Nature 348:552-554 (1990)), or those identified through hybridoma technology (Tomita M, Tsumoto K, Immunotherapy. March 2011, 3(3): 371-80), or those identified through B-cell cloning (Tiller T., Single B cell antibody technologies. New Biotechnol. 2011; 28:453-457).

For preparation of monoclonal or polyclonal antibodies, any technique known in the art can be used (see, e.g., Kohler & Milstein, Nature 256:495-497 (1975); Kozbor et al., Immunology Today 4:72 (1983); Cole et al., Monoclonal Antibodies and Cancer Therapy, pp. 77-96. Alan R. Liss, Inc. 1985; Advances in the production of human monoclonal antibodies Shixia Wang, Antibody Technology Journal 2011: 1 1-4; J Cell Biochem. 2005 Oct. 1; 96(2):305-13; Recombinant polyclonal antibodies for cancer therapy; Sharon J, Liebman M A, Williams B R; and Drug Discov Today. 2006 July, 11(13-14):655-60, Recombinant polyclonal antibodies: the next generation of antibody therapeutics?, Haurum J S). Techniques for the production of single chain antibodies (U.S. Pat. No. 4,946,778) can be adapted to produce antibodies to polypeptides of this invention. Also, transgenic mice, or other organisms such as other mammals, may be used to express fully human monoclonal antibodies. Alternatively, phage, yeast, or mammalian cells display technologies can be used to identify high affinity binders to selected antigens (see, e.g., McCafferty et al., supra; Marks et al., Biotechnology, 10:779-783, (1992)).

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. In some embodiments, the terms "donor" and "acceptor" sequences can be employed. Humanization can be essentially performed following the method of Winter and co-workers (see, e.g., Jones et al., Nature 321:522-525 (1986); Riechmann et al., Nature 332:323-327 (1988); Verhoeyen et al., Science 239: 1534-1536 (1988) and Presta, Curr. Op. Struct. Biol. 2:593-596 (1992)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some complementarity determining region ("CDR") residues and possibly some framework ("FR") residues are substituted by residues from analogous sites in rodent antibodies.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, and drug; or (b) the variable region, or a portion thereof, is altered, replaced or exchanged with a variable region having a different or altered antigen specificity.

Antibodies further include one or more immunoglobulin chains that are chemically conjugated to, or expressed as, fusion proteins with other proteins. In some embodiments, the antigen binding constructs can be monovalent scFv constructs. In some embodiments, the antigen binding constructs can be bispecific constructs. A bispecific or bifunctional antibody is an artificial hybrid antibody having two different heavy/light chain pairs and two different binding sites. Other antigen-binding fragments or antibody portions of the invention include bivalent scFv (diabody and cys-diabody), bispecific scFv antibodies where the antibody molecule recognizes two different epitopes, single binding domains (sdAb or nanobodies), and minibodies.

The term "antibody fragment" includes, but is not limited to, one or more antigen binding fragments of antibodies alone or in combination with other molecules, including, but not limited to Fab', F(ab')2, Fab, Fv, rIgG (reduced IgG), scFv fragments (monovalent, tri-valent, etc.), single domain fragments (nanobodies), peptibodies, minibodies, diabodies, and cys-diabodies. The term "scFv" refers to a single chain Fv ("fragment variable") antibody in which the variable domains of the heavy chain and of the light chain of a traditional two chain antibody have been joined to form one chain.

A pharmaceutically acceptable carrier may be a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or some combination thereof. Each component of the carrier is "pharmaceutically acceptable" in that it is be compatible with the other ingredients of the formulation. It also must be suitable for contact with any tissue, organ, or portion of the body that it may encounter, meaning that it must not carry a risk of toxicity, irritation, allergic response, immunogenicity, or any other complication that excessively outweighs its therapeutic benefits. The pharmaceutical compositions described herein may be administered by any suitable route of administration. A route of administration may refer to any administration pathway known in the art, including but not limited to aerosol, enteral, nasal, ophthalmic, oral, parenteral, rectal, transdermal (e.g., topical cream or ointment, patch), or vaginal. "Transdermal" administration may be accomplished using a topical cream or ointment or by means of a transdermal patch. "Parenteral" refers to a route of administration that is generally associated with injection, including infraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. In some embodiments, the antigen binding construct can be delivered intraoperatively as a local administration during an intervention or resection.

A minibody is an antibody format that has a smaller molecular weight than the full-length antibody while maintaining the bivalent binding property against an antigen. Because of its smaller size, the minibody has a faster clearance from the system and enhanced penetration when targeting tumor tissue. With the ability for strong targeting combined with rapid clearance, the minibody is advantageous for diagnostic imaging and delivery of cytotoxic/ radioactive payloads for which prolonged circulation times may result in adverse patient dosing or dosimetry.

The phrase "specifically (or selectively) bind," when used in the context of describing the interaction between an antigen, e.g., a protein, to an antibody or antibody-derived binding agent, refers to a binding reaction that is determinative of the presence of the antigen in a heterogeneous population of proteins and other biologics, e.g., in a biological sample, e.g., a blood, serum, plasma or tissue sample. Thus, under designated immunoassay conditions, in some embodiments, the antibodies or binding agents with a particular binding specificity bind to a particular antigen at least two times the background and do not substantially bind in a significant amount to other antigens present in the sample. Specific binding to an antibody or binding agent under such conditions may require the antibody or agent to have been selected for its specificity for a particular protein. A variety of immunoassay formats may be used to select antibodies specifically immunoreactive with a particular protein. For example, solid-phase ELISA and flow cytometry immunoassays are routinely used to select antibodies specifically immunoreactive with a protein (see, e.g., Harlow & Lane, Using Antibodies, A Laboratory Manual (1998), for a description of immunoassay formats and conditions that can be used to determine specific immunoreactivity). Typically, a specific or selective binding reaction will produce a signal at least twice over the background signal and more typically at least than 10 to 100 times over the background.

The term "equilibrium dissociation constant (KD, M)" refers to the dissociation rate constant (kd, time$^{-1}$) divided by the association rate constant (ka, time$^{-1}$*M$^{-1}$). Equilibrium dissociation constants can be measured using any known method in the art. The antibodies of the present invention generally will have an equilibrium dissociation constant of less than about $10^{-7}$ or $10^{-8}$ M, for example, less than about $10^{-9}$ M or $10^{-10}$ M, in some embodiments, less than about $10^{-11}$ M, $10^{-12}$ M, or $10^{-13}$ M.

The term "isolated," when applied to a nucleic acid or protein, denotes that the nucleic acid or protein is essentially free of other cellular components with which it is associated in the natural state. In some embodiments, it can be in either a dry or aqueous solution. Purity and homogeneity can be determined using analytical chemistry techniques such as polyacrylamide gel electrophoresis or high performance liquid chromatography (HPLC). A protein that is the predominant species present in a preparation is substantially purified. In particular, an isolated gene is separated from open reading frames that flank the gene and encode a protein other than the gene of interest. The term "purified" denotes that a nucleic acid or protein gives rise to essentially one band in an electrophoretic gel. In some embodiments, this can denote that the nucleic acid or protein is at least 85% pure, more preferably at least 95% pure, and most preferably at least 99% pure of molecules that are present under in vivo conditions.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

The terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, gamma-carboxyglutamate, and O-phosphoserine. Amino acid analogs refer to compounds that have the same basic chemical structure as a naturally occurring amino acid, i.e., an alpha-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

"Percentage of sequence identity" can be determined by comparing two optimally aligned sequences over a comparison window, wherein the portion of the polynucleotide sequence in the comparison window may comprise additions or deletions (i.e., gaps) as compared to the reference sequence (e.g., a polypeptide of the invention), which does not comprise additions or deletions, for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same sequences. Two sequences are "substantially identical" if two sequences have a specified percentage of amino acid residues or nucleotides that are the same (for example, 70%, 75%, 80%, 85%, 90%, 95%, 96%, 97%, 98% or 99% sequence identity over a specified region, or, when not specified, over the entire sequence of a reference sequence), when compared and aligned for maximum correspondence over a comparison window, or designated region as measured using one of the following sequence comparison algorithms or by manual alignment and visual inspection. Some embodiments provided herein provide polypeptides or polynucleotides that are substantially identical to the polypeptides or polynucleotides, respectively, exemplified herein. Optionally, the identity exists over a region that is at least about 15, 25 or 50 nucleotides in length, or more preferably over a region that is 100 to 500 or 1000 or more nucleotides in length, or over the full length of the reference sequence. With respect to amino acid sequences, identity or substantial identity can exist over a region that is at least 5, 10, 15 or 20 amino acids in length, optionally at least about 25, 30, 35, 40, 50, 75 or 100 amino acids in length, optionally at least about 150, 200 or 250 amino acids in length, or over the full length of the reference sequence. With respect to shorter amino acid sequences, e.g., amino acid sequences of 20 or fewer amino acids, in some embodiments, substantial identity exists when one or two amino acid residues are conservatively substituted, according to the conservative substitutions defined herein.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (Adv. Appl. Math. 2:482c (1970)), by the homology alignment algorithm of Needleman and Wunsch (J. Mol. Biol. 48:443 (1970)), by the search for similarity method of Pearson and Lipman (Proc. Nat'l. Acad. Sci. USA 85:2444 (1988)), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., Current Protocols in Molecular Biology (1995 supplement)).

Two examples of algorithms that are suitable for determining percent sequence identity and sequence similarity are the BLAST and BLAST 2.0 algorithms, which are described in Altschul et al. (1977) Nuc. Acids Res. 25:3389-3402, and Altschul et al. (1990) J. Mol. Biol. 215:403-410, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a word length of 3, and expectation (E) of 10, and the BLOSUM62 scoring matrix (see Henikoff and Henikoff (1989) Proc. Natl. Acad. Sci. USA 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) Proc. Natl. Acad. Sci. USA 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, in some embodiments, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The terms "subject," "patient," and "individual" interchangeably refer to an entity that is being examined and/or treated. This can include, for example, a mammal, for example a human or a non-human primate mammal. The mammal can also be a laboratory mammal, e.g., mouse, rat, rabbit, hamster. In some embodiments, the mammal can be an agricultural mammal (e.g., equine, ovine, bovine, porcine, camelid) or domestic mammal (e.g., canine, feline).

The term "therapeutically acceptable amount" or "therapeutically effective dose" interchangeably refer to an amount sufficient to affect the desired result. In some embodiments, a therapeutically acceptable amount does not induce or cause undesirable side effects. A therapeutically acceptable amount can be determined by first administering a low dose, and then incrementally increasing that dose until the desired effect is achieved.

The term "embodiment" as used herein denotes various components or arrangements as well as groupings and combinations of elements. The term does not necessarily denote discrete inventions. That is, it is contemplated that the various embodiments provided herein can be combined with one another using the guidance provided herein, for various claimed combinations.

Antigen Binding Constructs (Including Antibodies and Binding Fragments)

Antigen binding constructs that bind to the target are described herein. An antigen binding construct is a molecule that includes one or more portions of an immunoglobulin or immunoglobulin-related molecule that specifically binds to, or is immunologically reactive with, the target molecule. For all of the antigen binding constructs provided herein, as minibody, diabody, and/or cys-diabody arrangement is each specifically contemplated in the same context.

In some embodiments, any of the humanized minibodies or antigen binding constructs, or cys-diabodies provided herein (including one or more of SEQ ID Nos: 5-8, for example, 5) can be labeled with a detectable marker, such as one or more of the positron emitters provided herein, $^{18}$F or $^{89}$Zr for example, via a chelator, for example, deferoxamine (DfO). This can form a labeled construct.

In some embodiments, an antigen binding construct includes a heavy chain CDR1 (HCDR1) of the HCDR1 in SEQ ID NO: 2; a heavy chain CDR2 (HCDR2) of the HCDR2 in SEQ ID NOs: 2; a heavy chain CDR3 (HCDR3) of the HCDR3 in SEQ ID NO: 2; a light chain CDR1 (LCDR1) of the LCDR1 in SEQ ID NO: 3; a light chain CDR2 (LCDR2) of the LCDR2 in SEQ ID No: 3; and/or a light chain CDR3 (LCDR3) of the LCDR3 in SEQ ID NO: 3. In some embodiments, the antigen binding construct includes 6, 5, 4, 3, 2, or 1 of the above CDRs. In some embodiments, the antigen binding construct binds specifically to the target molecule. In some embodiments, the antigen binding construct competes for binding with one or more of the antibodies having the herein provided CDRs. In some embodiments, the antigen binding construct is human or humanized. In some embodiments, the antigen binding construct includes a detectable marker. In some embodiments, the antigen binding construct includes a therapeutic agent.

In some embodiments, the antigen binding construct is bivalent. Bivalent antigen binding construct can include at least a first antigen binding domain, for example a first scFv, and at least a second antigen binding domain, for example a second scFv. In some embodiments, a bivalent antigen binding construct is a multimer that includes at least two monomers, for example at least 2, 3, 4, 5, 6, 7, or 8 monomers, each of which has an antigen binding domain. In some embodiments, the antigen binding construct is a minibody. In some embodiments, the antigen binding construct is a diabody, including, for example, a cys-diabody. The scFv, and/or minibody and/or the cys-diabody can include any of the CDR and heavy chain variable region and/or light chain variable region embodiments provided herein.

In some embodiments, the antigen binding construct has a heavy chain variable region of the heavy chain variable region in SEQ ID NO: 2. In some embodiments, the antigen binding construct has a heavy chain variable region that includes a sequence with at least about 80% identity, for example at least about 80%, 85%, 86%, 87%, 88%, 89%, 90%, 91%, 92%, 93%, 94%, 95%, 96%, 97%, 98%, or 99% identity to SEQ ID NO: 2. In some embodiments, the CDRs within SEQ ID NO:2 are maintained, while the other residues can be altered. In some embodiments, the antigen binding construct is as shown in FIG. 4, or includes any one or more of the differences shown in IAB41 as compared to MAX16H5 (in either or both of SEQ ID NO: 2 or 4). In some embodiments, the antigen binding construct has at least 1, 2, 3, 4, 5, 6, 7 or more of the differences shown in IAB41 compared to MAX16H5. In some embodiments, it has sufficient differences to provide for the same level of binding and/or specificity and/or production as IAB41. In some embodiments, the antigen binding construct has at least 50, 60, 70, 80, 90, 95, 98, 99, or 100% of the same level of binding and/or specificity and/or production as IAB41.

In some embodiments, the antigen binding construct has a light chain variable region that includes SEQ ID NO: 4. In some embodiments, the antigen binding construct has a light chain variable region that includes a sequence with least about 80% identity, for example at least about 80%, 85%, 86%, 87%, 88%, 89%, 90%, 91%, 92%, 93%, 94%, 95%, 96%, 97%, 98%, or 99% identity to SEQ ID NO: 4. In some embodiments, the CDRs within SEQ ID NO:4 are maintained, while the other residues can be altered.

Some embodiments provided herein include an antigen binding construct that competes for binding to the target molecule with one or more antigen binding constructs provided herein. In some embodiments, the competing antigen binding construct binds to the same epitope on the target molecule as the reference antigen binding construct. In some embodiments, the reference antigen binding construct binds to a first epitope of the target molecule, and the competing antigen binding construct binds to a second epitope of the target molecule, but interferes with binding of the reference antigen binding construct to the target molecule, for example by sterically blocking binding of the reference antigen binding construct, or by inducing a conformational change in the target molecule. In some embodiments, the first epitope overlaps with the second epitope. In some embodiments, any of the heavy chains variable regions provided herein can be combined with any of the light chain variable regions herein for a scFv, minibody, and/or diabody.

In some embodiments, the minibody and cys-diabody formats have advantageous pharmacokinetic characteristics for diagnostic imaging and certain therapeutic applications while maintaining the high binding affinity and specificity of a parental antibody. Compared to imaging with the full-length parental antibody, the pharmacokinetics are more desirable for these fragments in that they are able to target the antigen and then rapidly clear the system for rapid high-contrast imaging. In some embodiments, the shorter serum half-lives for the minibody and the cys-diabody allow for imaging to occur over a range of times, approximately 8-48 hours post injection for the minibody and 2-24 hours post-injection for the cys-diabody. The rapid serum clearance together with better tissue penetration can allow for same day imaging, providing a significant advantage in the clinic with respect to patient care management.

In some embodiments, an antigen binding construct is provided that comprises a HCDR1 of the HCDR1 in SEQ ID NO: 2, a HCDR2 of the HCDR2 in SEQ ID NO: 2, a HCDR3 of the HCDR3 in SEQ ID NO: 2, a LCDR1 of the LCDR1 in SEQ ID NO: 4, a LCDR2 of the LCDR2 in SEQ ID NO: 4, and a LCDR3 of the LCDR3 in SEQ ID NO: 4. In some embodiments, any of the CDRs as shown in FIGS. 19 and 20 can be employed. The antigen binding construct (which can be, for example, a minibody or a cys-diabody) having these CDRs can include one or more of the following arrangements as well (as provided in a) through n)).

a) At least one VH framework residue selected from the group consisting of: a Glutamine at position 1 of the sequence in SEQ ID NO: 2; a Valine at position 5 of the sequence in SEQ ID NO: 2; an Alanine at position 9 of the sequence in SEQ ID NO: 2; a Valine at position 11 of the sequence in SEQ ID NO: 2; a Lysine at position 13 of the sequence in SEQ ID NO: 2; an Arginine at position 44 of the sequence in SEQ ID NO: 2; a Glutamic acid at position 46 of the sequence in SEQ ID NO: 2; a Glutamine at position 65 of the sequence in SEQ ID NO: 2; a Glycine at position 66 of the sequence in SEQ ID NO: 2; an Arginine at position 67 of the sequence in SEQ ID NO: 2; a Valine at position 68 of the sequence in SEQ ID NO: 2; a Threonine at position 69 of the sequence of SEQ ID NO: 2; an Arginine at position 87 of the sequence in SEQ ID NO: 2; and a Serine at position 88 of the sequence in SEQ ID NO: 2.

b) At least one VL framework residue selected from the group consisting of: a Glutamic acid at position 1 of the sequence in SEQ ID NO: 4; a Leucine at position 13 of the sequence in SEQ ID NO: 4; an Arginine at position 18 of the sequence in SEQ ID NO: 4; a Threonine at position 20 of the sequence in SEQ ID NO: 4; a Leucine at position 21 of the sequence in SEQ ID NO: 4; a Serine at position 22 of the sequence in SEQ ID NO: 4; a Glutamine at position 41 of the sequence in SEQ ID NO: 4; an Alanine at position 42 of the sequence in SEQ ID NO: 4; an Isoleucine at position 57 of the sequence in SEQ ID NO: 4; an Aspartic acid at position 59 of the sequence in SEQ ID NO: 4; a Phenylalanine at position 70 of the sequence in SEQ ID NO: 4; a Threonine at position 71 of the sequence in SEQ ID NO: 4; a Leucine at position 77 of the sequence in SEQ ID NO: 4; a Proline at position 79 of the sequence in SEQ ID NO: 4; a Valine at position 84 of the sequence in SEQ ID NO: 4; and a Glycine at position 99 of the sequence in SEQ ID NO: 4.

c) a) combined with b).

d) At least one of: a Glutamine at position 1 of the sequence in SEQ ID NO: 2; a Valine at position 2 of the sequence in SEQ ID NO: 2; a Leucine at position 4 of the sequence in SEQ ID NO: 2; an Alanine at position 24 of the sequence in SEQ ID NO: 2; a Serine at position 25 of the sequence in SEQ ID NO: 2; a Methionine at position 34 of the sequence in SEQ ID NO: 2; a Histidine at position 35 of the sequence in SEQ ID NO: 2; a Glutamic acid position 46 of the sequence in SEQ ID NO: 2; a Tryptophan at position 47 of the sequence in SEQ ID NO: 2; an Isoleucine at position 48 of the sequence in SEQ ID NO: 2; a Glycine at position 49 of the sequence in SEQ ID NO: 2; an Alanine at position 50 of the sequence in SEQ ID NO: 2; a Leucine at position 51 of the sequence in SEQ ID NO: 2; an Asparagine at position 61 of the sequence in SEQ ID NO: 2; a Phenylalanine at position 64 of the sequence in SEQ ID NO: 2; an Isoleucine at position 70 of the sequence in SEQ ID NO: 2; an Arginine at position 72 of the sequence in SEQ ID NO: 2; an Alanine at position 79 of the sequence in SEQ ID NO: 2; a Threonine at position 97 of the sequence in SEQ ID NO: 2; an Arginine at position 98 of the sequence in SEQ ID NO: 2; a Glutamic acid at position 1 of the sequence in SEQ ID NO: 4; an Isoleucine at position 2 of the sequence in SEQ ID NO: 4; a Leucine at position 4 of the sequence in SEQ ID NO: 4; a Glutamine at position 6 of the sequence in SEQ ID NO: 4; a Tryptophan at position 34 of the sequence in SEQ ID NO: 4; a Tyrosine at position 35 of the sequence in SEQ ID NO: 4; a Leucine at position 45 of the sequence in SEQ ID NO: 4; a Leucine at position 46 of the sequence in SEQ ID NO: 4; an Isoleucine at position 47 of the sequence in SEQ ID NO: 4; a Glycine at position 67 of the sequence in SEQ ID NO: 4; a Phenylalanine at position 70 of the sequence in SEQ ID NO: 4; a Phenylalanine at position 97 of the sequence in SEQ ID NO: 4.

e) At least one of: a Glutamine at position 1 of the sequence in SEQ ID NO: 2; a Valine at position 20 of the sequence in SEQ ID NO: 2; an Arginine at position 38 of the sequence in SEQ ID NO: 2; an Alanine at position 40 of the sequence in SEQ ID NO: 2; an Arginine at position 44 of the sequence in SEQ ID NO: 2; a Tyrosine at position 60 of the sequence in SEQ ID NO: 2; a Valine at position 68 of the sequence in SEQ ID NO: 2; an Isoleucine at position 70 of the sequence in SEQ ID NO: 2; an Arginine at position 72 of the sequence in SEQ ID NO: 2; and a Threonine at position 74 of the sequence in SEQ ID NO: 2.

f) At least one of: a Glutamic acid at position 1 of the sequence in SEQ ID NO: 4; a Leucine at position 11 of the sequence in SEQ ID NO: 4; a Leucine at position 13 of the sequence in SEQ ID NO: 4; an Alanine at position 19 of the sequence in SEQ ID NO: 4; a Leucine at position 21 of the sequence in SEQ ID NO: 4; an Isoleucine at position 57 of the sequence in SEQ ID NO: 4; a Phenylalanine at position 70 of the sequence in SEQ ID NO: 4; a Leucine at position 77 of the sequence in SEQ ID NO: 4; a Proline at position 79 of the sequence in SEQ ID NO: 4; a Valine at position 84 of the sequence in SEQ ID NO: 4; and a Glycine at position 99 of the sequence in SEQ ID NO: 4.

g) e) combined with f).

h) At least one of a Glutamine at position 1 of the sequence in SEQ ID NO: 2; a Valine at position 2 of the sequence in SEQ ID NO: 2; a Leucine at position 4 of the sequence in SEQ ID NO: 2; an Alanine at position 24 of the sequence in SEQ ID NO: 2; a Serine at position 25 of the sequence in SEQ ID NO: 2; a Methionine at position 34 of the sequence in SEQ ID NO: 2; a Histidine at position 35 of the sequence in SEQ ID NO: 2; a Glutamic acid position 46 of the sequence in SEQ ID NO: 2; a Tryptophan at position 47 of the sequence in SEQ ID NO: 2; an Isoleucine at position 48 of the sequence in SEQ ID NO: 2; a Glycine at position 49 of the sequence in SEQ ID NO: 2; an Alanine at position 50 of the sequence in SEQ ID NO: 2; a Leucine at position 51 of the sequence in SEQ ID NO: 2; an Asparagine at position 61 of the sequence in SEQ ID NO: 2; a Phenylalanine at position 64 of the sequence in SEQ ID NO: 2; an Isoleucine at position 70 of the sequence in SEQ ID NO: 2; an Arginine at position 72 of the sequence in SEQ ID NO: 2; an Alanine at position 79 of the sequence in SEQ ID NO: 2; a Threonine at position 97 of the sequence in SEQ ID NO: 2; an Arginine at position 98 of the sequence in SEQ ID NO: 2;

i) At least one of: a Glutamic acid at position 1 of the sequence in SEQ ID NO: 4; an Isoleucine at position 2 of the sequence in SEQ ID NO: 4; a Leucine at position 4 of the sequence in SEQ ID NO: 4; a Glutamine at position 6 of the sequence in SEQ ID NO: 4; a Tryptophan at position 34 of the sequence in SEQ ID NO: 4; a Tyrosine at position 35 of the sequence in SEQ ID NO: 4; a Leucine at position 45 of the sequence in SEQ ID NO: 4; a Leucine at position 46 of the sequence in SEQ ID NO: 4; an Isoleucine at position 47 of the sequence in SEQ ID NO: 4; a Glycine at position 67 of the sequence in SEQ ID NO: 4; a Phenylalanine at position 70 of the sequence in SEQ ID NO: 4; and a Phenylalanine at position 97 of the sequence in SEQ ID NO: 4.

j) h) combined with i).

k) Any one or more of the framework residues that is different in the alignment between the mouse and humanized sequences in FIG. 3.

l) Any one or more of the residues in the Vernier zones of the humanized sequence in FIG. 4, FIG. 20 and/or FIG. 21, where the humanized sequence is different from the mouse sequence.

m) At least 2, 3, 4, 5, 6, 7, 8, 9, 10, 11, 12, 13, 14, 15, 16, or more of the residues noted in any one or more of a-l).

n) At least 50%, 60%, 70%, 80%, 90%, 95%, 96%, 97%, 98%, 99% or 100% of the residues noted in any one of a)-l).

While reference is made to SEQ ID NO: 2 or 4, the references above (unless context dictates otherwise) are for residue positioning. Thus, a reference to a particular residue does not require the presence of any of the other residues in the sequence, unless denoted otherwise.

In some embodiments, an antigen binding construct (such as a minibody, diabody, or cys-diabody) comprises: a HCDR1 of the HCDR1 in SEQ ID NO: 2; a HCDR2 of the HCDR2 in SEQ ID NO: 2; a HCDR3 of the HCDR3 in SEQ ID NO: 2; a LCDR1 of the LCDR1 in SEQ ID NO: 4; a LCDR2 of the LCDR2 in SEQ ID NO: 4; a LCDR3 of the LCDR3 in SEQ ID NO: 4; and at least one of the following:
a) a VH comprising at least one of: E1Q, Q5V, T9A, V10E, L11V, A12K, R13K, Q19K, M20V, K38R, R40A, Q46E, T59, N61, K65Q, D66G, K67R, A68V, K69T, L70I, A72R, V73D, T87R, N88S, S91T, T115L, or L116V; and
b) a VL comprising at least one of: 1E, 10T, 11L, 13L, 18R, 19A, 20T, 21L, 22S, 41Q, 42A, 57I, 59D, 62S, 69D, 70F, 71T, 77L, 79P, A82, 84V, 99G, or 106I.

The CDRs can be any CDR as understood by one of skill in the art, including the CDRs discussed herein and/or including any of the CDRs shown in the accompanying drawings.

In some embodiments, an antigen binding construct comprises a HCDR1 of the HCDR1 in SEQ ID NO: 2; a HCDR2 of the HCDR2 in SEQ ID NO: 2; a HCDR3 of the HCDR3 in SEQ ID NO: 2; a LCDR1 of the LCDR1 in SEQ ID NO: 4; a LCDR2 of the LCDR2 in SEQ ID NO: 4; a LCDR3 of the LCDR3 in SEQ ID NO: 4; and at least one of:
a) a VH comprising at least one of: E1Q, Q5V, T9A, V10E, L11V, A12K, R13K, Q19K, M20V, K38R, R40A, Q46E, T59, N61, K65Q, D66G, K67R, A68V, K69T, L70I, A72R, V73D, T87R, N88S, S91T, T115L, or L116V and
b) a VL comprising at least one of: Q1E, I10T, M11L, A13L, K18R, V19A, A20T, M21L, T22S, S41Q, S42A, V57I, V59D, I62S, S69D, Y70F, S71T, M77L, A79P, A82, T84V, A99G, or L106I. While the residues are denoted in terms of particular positions and in terms of starting amino acid and final amino acid, this does not denote a product by process or other historical process context for the amino acid position. Rather, the initial amino acid denotes what amino acid was present in other constructs and the final amino acid denotes what amino acid residue is actually present in the designated construct. Thus, there is no difference in the present disclosure for the various nomenclature such as E1Q, 1Q, Q1, position 1 is a glutamine, glutamine at position 1, or other such nomenclature. All such designations merely denote that position 1 of the construct is a glutamine (and no historical or process aspects are denoted by the terminology). The nomenclature E1Q is occasionally used to provide additional context of how this particular construct differs from other constructs (for example, one which may have a glutamic acid at position 1).

In some embodiments, the antigen binding construct includes a VH with at least 2, 3, 4, 5, 6, 7, 8, 9, 10, 11, 12, 13, 14, 15, 16, 17, 18, 19, 20, 21, 22, 23, 24, 25, 26, or 27 of a) E1Q, Q5V, T9A, V10E, L11V, A12K, R13K, Q19K, M20V, K38R, R40A, Q46E, T59, N61, K65Q, D66G, K67R, A68V, K69T, L70I, A72R, V73D, T87R, N88S, S91T, T115L, or L116V and/or a VL with at least 1, 2, 3, 4, 5, 6, 7, 8, 9, 10, 11, 12, 13, 14, 15, 16, 17, 18, 19, 20, 21, 22, or 23 of: Q1E, I10T, M11L, A13L, K18R, V19A, A20T, M21L, T22S, S41Q, S42A, V57I, V59D, I62S, S69D, Y70F, S71T, M77L, A79P, A82, T84V, A99G, or L106I. In some embodiments, all of these point mutations, in both chains are present with 1, 2, 3, 4, 5 or 6 of the CDRs (HCDR1-3 and LCDR1-3) in SEQ ID Nos:2 and 4.

In some embodiments, the antigen binding construct comprises a VH with T59, N61, or both, wherein the VH is a humanized VH. In some embodiments, the antigen binding construct comprises a VL with A82, wherein the VL is a humanized VL. In some embodiments, the antigen binding construct comprises a VH with T59, N61, or both, wherein the VH is a humanized VH; and wherein the antigen binding construct comprises a VL with A82, wherein the VL is a humanized VL. In some embodiments, the antigen binding construct comprises SEQ ID NO: 5. In some embodiments, the humanized minibody comprises a VH with T59, N61, or both, wherein the VH is a humanized VH, wherein the VH is at least 80% identical to SEQ ID NO: 2. In some embodiments, the humanized minibody comprises and a VL that is at least 80% identical to SEQ ID NO: 4 and wherein the VL comprises A99G. In some embodiments, the humanized minibody comprises a VH with T59, N61, or both, wherein the VH is a humanized VH, wherein the VH is at least 80% identical to SEQ ID NO: 2; and wherein the humanized minibody comprises and a VL that is at least 80% identical to SEQ ID NO: 4 and wherein the VL comprises A99G. In some embodiments, the humanized minibody comprises a VH comprising T59, N61, or both, wherein the VH is a humanized VH as numbered accord to the numbering of SEQ ID NO: 2.

In some embodiments, the humanized minibody comprises a VL comprising A99G, as numbered accord to the numbering of SEQ ID NO: 4. In some embodiments, the humanized minibody comprises a VH comprising T59, N61, or both, wherein the VH is a humanized VH as numbered accord to the numbering of SEQ ID NO: 2; and wherein the humanized minibody comprises a VL comprising A99G, as numbered accord to the numbering of SEQ ID NO: 4. In some embodiments, the humanized minibody comprises SEQ ID NO: 5.

In some embodiments, an antigen binding construct comprises a HCDR1 of the HCDR1 in SEQ ID NO: 2; a HCDR2 of the HCDR2 in SEQ ID NO: 2; a HCDR3 of the HCDR3 in SEQ ID NO: 2; a LCDR1 of the LCDR1 in SEQ ID NO: 4; a LCDR2 of the LCDR2 in SEQ ID NO: 4; a LCDR3 of the LCDR3 in SEQ ID NO: 4; and at least one of:
  a) a VH comprising at least one of: E1Q, Q5V, T9A, V10E, L11V, A12K, R13K, Q19K, M20V, K38R, R40A, Q46E, T59, N61, K65Q, D66G, K67R, A68V, K69T, L70I, A72R, V73D, T87R, N88S, S91T, T115L, or L116V and/or
  b) a VL comprising at least one of: Q1E, I10T, M11L, A13L, K18R, V19A, A20T, M21L, T22S, S41Q, S42A, V57I, V59D, I62S, S69D, Y70F, S71T, M77L, A79P, A82, T84V, A99G, or L106I, and/or
  c) the VH of a) and the VL of b), and/or
  d) any one of a), b), and c), wherein the VH is at least 80% identical to SEQ ID NO: 2, and/or
  e) any one of a), b), and c), wherein the VL is at least 80% identical to SEQ ID NO: 4, and/or
  f) any one of a), b), and c), wherein the VH is at least 80% identical to SEQ ID NO: 2; and any one of a), b), and c), wherein the VL is at least 80% identical to SEQ ID NO: 4, and/or
  g) a VH with T59, N61, or both, wherein the VH is a humanized VH, and/or
  h) a VL with A82, wherein the VL is a humanized VL, and/or
  i) a VH according to g) and a VL according to h), and/or
  j) a VH with Q46E, and/or
  k) a VH with Q46E, wherein
    i) the VH is at least 80% identical to SEQ ID NO: 2
    ii) the VL is at least 80% identical to SEQ ID NO: 4
    iii) the VH is at least 80% identical to SEQ ID NO: 2 and the VL is at least 80% identical to SEQ ID NO: 4, and/or
  l) a VH with at least one of T115L, L116V, and/or
  m) a VL with at least one of S41Q, A99G, or L106I, and/or
  n) a VH with at least one of T115L, L116V and a VL with at least one of S41Q, A99G, or L106I, and/or
  o) l), m), or n), wherein
    i) the VH is at least 80% identical to SEQ ID NO: 2
    ii) the VL is at least 80% identical to SEQ ID NO: 4
    iii) the VH is at least 80% identical to SEQ ID NO: 2 and the VL is at least 80% identical to SEQ ID NO: 4.

In some embodiments, the antigen binding construct (including an antibody, a minibody, or a cys-diabody for example) can include a heavy and a light chain as follows:
a) a VH comprising at least one of: 1Q, 5V, 9A, 10E, 11V, 12K, 13K, 19K, 20V, 38R, 40A, 46E, T59, N61, 65Q, 66G, 67R, 68V, 69T, 70I, 72R, 73D, 87R, 88S, 91T, 115L, or 116V; and b) a VL comprising at least one of: 1E, 10T, 11L, 13L, 18R, 19A, 20T, 21L, 22S, 41Q, 42A, 57I, 59D, 62S, 69D, 70F, 71T, 77L, 79P, 82, 84V, 99G, or 106I. As noted herein, the numbering denotes the corresponding position in FIGS. 20 and 21. In some embodiments, these constructs bind to CD4. In other embodiments, the constructs can simply be amino acid (or nucleic acids encoding them) that have these particular sequences and no functionality is required.

In some embodiments, the antigen binding construct for any of the above options (a-o) is a minibody.

In some embodiments, of the antigen binding construct (e.g., a minibody), the VH that is at least 90% identical to SEQ ID NO: 2, the VL is at least 90% identical to SEQ ID NO: 4, or the VH and VL are at least 90% identical to SEQ ID Nos: 2 and 4 respectively. In some embodiments, the VH is at least 95% identical to SEQ ID NO: 2, the VL is at least 95% identical to SEQ ID NO: 4, or the VH and VL are at least 95% identical to SEQ ID Nos: 2 and 4 respectively. In some embodiments, the VH is at least 99% identical to SEQ ID NO: 2, the VL is at least 99% identical to SEQ ID NO: 4, or the VH and VL are at least 99% identical to SEQ ID Nos: 2 and 4 respectively. In some embodiments, the percent identity is 91, 92, 93, 94, 95, 96, 97, 98, or greater to SEQ ID NO: 2, 4, or 2 and 4. In some embodiments, the percent identity is the at least 80, 85, 90, 95, 96, 97, 98, 99, or greater to SEQ ID NO: 2 and/or 4 and the CDRs are identical to the CDRs in SEQ ID NO: 2 and/or 4, or the CDRs vary by no more than 1, 2, or 3 conserved mutations.

In some embodiments of the antigen binding construct (e.g., a minibody), the VH is identical to SEQ ID NO: 2, the VL is identical to SEQ ID NO: 4, or the VH and VL are identical to SEQ ID Nos: 2 and 4 respectively.

In some embodiments of the antigen binding construct (e.g., a minibody), the antigen binding construct binds to CD4. In some embodiments, the CD4 is human CD4. In some embodiments, the human CD4 has the amino acid sequence as shown in FIG. 21 (as SEQ ID NO: 44).

In some embodiments, a humanized minibody that binds to human CD4 is provided. The humanized minibody comprises: a HCDR1 of the HCDR1 in SEQ ID NO: 2; a HCDR2 of the HCDR2 in SEQ ID NO: 2; a HCDR3 of the HCDR3 in SEQ ID NO: 2; a LCDR1 of the LCDR1 in SEQ ID NO: 4; a LCDR2 of the LCDR2 in SEQ ID NO: 4; a LCDR3 of the LCDR3 in SEQ ID NO: 4; and at least one of:
  a) a VH with T59, N61, or both, wherein the VH is a humanized VH, wherein the VH is at least 80% identical to SEQ ID NO: 2, and a VL that is at least 80% identical to SEQ ID NO: 4;
  b) a VH and VL that is in the VL-VH orientation (amino to carboxyl) (and can optionally be the sequence of SEQ ID NOs: 2 and 4);
  c) a VL with A99G;
  d) a VH with T59, N61, or both,
  e) i) a VL with A99G and ii) a VH with T59, N61, or both, f) a VH with T59, N61, or both, wherein the VH is a humanized VH, wherein the VH is at least 80% identical to SEQ ID NO: 2, and a VL that is at least 80% identical to SEQ ID NO: 4 and wherein the VL comprises A99G; and/or g) A VH comprising T59, N61, or both, wherein the VH is a humanized VH as numbered accord to the numbering of SEQ ID NO: 2, and A VL comprising A99G, as numbered accord to the numbering of SEQ ID NO: 4.

In some embodiments, an antigen binding construct is provided that binds to human CD4. The antigen binding construct comprises: a HCDR1 of the HCDR1 in SEQ ID NO: 2; a HCDR2 of the HCDR2 in SEQ ID NO: 2; a HCDR3 of the HCDR3 in SEQ ID NO: 2; a LCDR1 of the LCDR1 in SEQ ID NO: 4; a LCDR2 of the LCDR2 in SEQ ID NO: 4; a LCDR3 of the LCDR3 in SEQ ID NO: 4; and at least one of:

a) a VH with T59, N61, or both, wherein the VH is a humanized VH, wherein the VH is at least 80% identical to SEQ ID NO: 2, and a VL that is at least 80% identical to SEQ ID NO: 4;

b) a VH and VL that is in the VL-VH orientation (amino to carboxyl) (and can optionally be the sequence of SEQ ID NOs: 2 and 4);

c) a VL with A99G;

d) a VH with T59, N61, or both, e) i) a VL with A99G and ii) a VH with T59, N61, or both, f) a VH with T59, N61, or both, wherein the VH is a humanized VH, wherein the VH is at least 80% identical to SEQ ID NO: 2, and a VL that is at least 80% identical to SEQ ID NO: 4 and wherein the VL comprises A99G; and/or g) A VH comprising T59, N61, or both, wherein the VH is a humanized VH as numbered accord to the numbering of SEQ ID NO: 2, and A VL comprising A99G, as numbered accord to the numbering of SEQ ID NO: 4.

In some embodiments, a humanized minibody (or an antigen binding construct) that binds to human CD4 is provided. The humanized minibody (or an antigen binding construct) comprises at least one of:

a) a VH with T59, N61, or both, wherein the VH is a humanized VH, wherein the VH is at least 80% identical to SEQ ID NO: 2, and a VL that is at least 80% identical to SEQ ID NO: 4;

b) a VH and VL that is in the VL-VH orientation (amino to carboxyl) (and can optionally be the sequence of SEQ ID NOs: 2 and 4);

c) a VL with A99G;

d) a VH with T59, N61, or both, e) a VL with A99G and ii) a VH with T59, N61, or both, f) a VH with T59, N61, or both, wherein the VH is a humanized VH, wherein the VH is at least 80% identical to SEQ ID NO: 2, and a VL that is at least 80% identical to SEQ ID NO: 4 and wherein the VL comprises A99G; and/or g) A VH comprising T59, N61, or both, wherein the VH is a humanized VH as numbered accord to the numbering of SEQ ID NO: 2, and A VL comprising A99G, as numbered accord to the numbering of SEQ ID NO: 4.

In some embodiments, the minibody (humanized or otherwise) that binds to human CD4 can have the orientation of VL-VH (as opposed to VH-VL). In some embodiments, this arrangement allows for a construct with superior distribution aspects. In some embodiments, the construct will have a superior pharmacokineics, pharmacodynamics, clearance rate and/or production behavior. Any of the antigen binding constructs, minibodies, or methods of use provided herein can be employed in an arrangement in which the construct is in the VL-VH orientation. In some embodiments, the VH-VL orientation provides an improvement for at least one of: production yield, solubility, formulation, aggregation propensity, or the EC50. In some embodiments, the VL-VH orientation provides an improvement for at least one of: production yield, solubility, formulation, aggregation propensity, or the EC50.

In some embodiments of the antigen binding construct (e.g., a minibody) further comprises a hinge region comprising the amino acid sequence in SEQ ID NO: 34, 35, 36, or 37.

In some embodiments of the antigen binding construct (e.g., a minibody), for a)-f), there are at least two of: E1Q, Q5V, T9A, V10E, L11V, A12K, R13K, Q19K, M20V, K38R, R40A, Q46E, T59, N61, K65Q, D66G, K67R, A68V, K69T, L70I, A72R, V73D, T87R, N88S, S91T, T115L, or L116V for VH and/or at least two of Q1E, I10T, M11L, A13L, K18R, V19A, A20T, M21L, T22S, S41Q, S42A, V57I, V59D, I62S, S69D, Y70F, S71T, M77L, A79P, A82, T84V, A99G, or L106I for VL. In some embodiments, there are at least 2, 3, 4, 5, 6, 7, 8, 9, or 10 of these residues, or all of them. In some embodiments, there is at least 10, 20, 30, 40, 50, 60, 70, 80, 90, 95, 96, 97, 98, 99, or 100% of these residues within the construct.

In some embodiments of the antigen binding construct (e.g., a minibody), the minibody is covalently linked to a detectable marker. In some embodiments of the antigen binding construct (e.g., a minibody), the detectable marker is at least one of $^{18}$F or $^{89}$Zr. In some embodiments, any of the detectable markers provided herein can be employed.

Diabodies

In some embodiments, the antigen binding construct can be a diabody. The diabody can include a first polypeptide chain which includes a heavy ($V_H$) chain variable domain connected to a light chain variable domain ($V_L$) on the first polypeptide chain. In some embodiments, the light and heavy variable chain domains can be connected by a linker. The linker can be of the appropriate length to reduce the likelihood of pairing between the two domains on the first polypeptide chain and a second polypeptide chain comprising a light chain variable domain ($V_L$) linked to a heavy chain variable domain $V_H$ on the second polypeptide chain connected by a linker that is too short to allow significant pairing between the two domains on the second polypeptide chain. In some embodiments, any of the embodiments in a)-n) denoted herein can be employed as a diabody and/or cys-diabody arrangement.

In some embodiments, the appropriate length of the linker encourages chain pairing between the complementary domains of the first and the second polypeptide chains and can promote the assembly of a dimeric molecule with two functional antigen binding sites. Thus, in some embodiments, the diabody is bivalent. In some embodiments, the diabody can be a cysteine linked diabody (a Cys-Db).

In some embodiments, the linker can be a peptide. In some embodiments, the linker can be any suitable length that promotes such assembly, for example, between 1 and 20 amino acids, such as 5 and 10 amino acids in length. As described further herein, some cys-diabodies can include a peptide linker that is 5 to 8 amino acids in length. In some embodiments, the linker need not be made from, or exclusively from amino acids, and can include, for example, modified amino acids (see, for example, Increased Resistance of Peptides to Serum Proteases by Modification of their Amino Groups, Rossella Galati, Alessandra Verdina, Giuliana Falasca, and Alberto Chersi, (2003) Z. Naturforsch, 58c, 558-561). In some embodiments, the linker can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 amino acids in length. In some embodiments, the linker can be from 2 to 30 angstroms in length, for example 2.5 to 27 angstroms. In some embodiments, the linker can be from 2 to 60 angstroms in length.

In some embodiments, the antigen binding construct includes a humanized cys-diabody. The humanized cys-diabody can include a single-chain variable fragment (scFv) that includes a variable heavy ($V_H$) domain linked to a variable light ($V_L$) domain, and a C-terminal cysteine. In some embodiments, the humanized cys-diabody is a homodimer. In some embodiments, the humanized diabody is a heterodimer. In some embodiments, individual monomers are provided that each have a cysteine terminal residue.

In some embodiments, the scFv of the humanized cys-diabody has a $V_H$-$V_L$ orientation or a $V_L$-$V_H$ orientation. As used herein, a $V_H$-$V_L$ (which may also be referred to herein as "$V_H V_L$") orientation means that the variable heavy domain ($V_H$) of the scFv is upstream from the variable light domain ($V_L$) and a $V_L V_H$ orientation means that the $V_L$ domain of the scFv is upstream from the $V_H$ domain. As used herein, "upstream" means toward the N-terminus of an amino acid or toward the 5' end of a nucleotide sequence.

The antibody variable regions can be linked together by a linker as described herein. In some embodiments, the linker is a GlySer linker.

In some embodiments, the cys-diabody includes a detectable marker.

In some embodiments, the cys-diabody includes a pair of monomers. Each monomer can include a polypeptide. In some embodiments, the polypeptides of the monomers are identical (for example, cys-diabody can be a homodimer). In some embodiments, the polypeptides of the monomers are different (for example, the cys-diabody can be a heterodimer).

In some embodiments, the antigen binding construct can include SEQ ID NO: 11 (See FIG. 10). In some embodiments, the polypeptide of the monomer includes a sequence with least about 80% identity, for example at least about 80%, 85%, 86%, 87%, 88%, 89%, 90%, 91%, 92%, 93%, 94%, 95%, 96%, 97%, 98%, or 99% identity to SEQ ID NO: 11.

In some embodiments, the CDR sequences (e.g., with FIGS. 20 and 21) are maintained and the rest of the sequence is allowed to vary.

In some embodiments, the antigen binding construct can include SEQ ID NO: 12 (See FIG. 11). In some embodiments, the polypeptide of the monomer includes a sequence with least about 80% identity, for example at least about 80%, 85%, 86%, 87%, 88%, 89%, 90%, 91%, 92%, 93, 94, 95%, 96%, 97%, 98%, or 99% identity to SEQ ID NO: 12.

In some embodiments, the CDR sequences (e.g., as denoted in FIGS. 20 and 21) are maintained and the rest of the sequence is allowed to vary.

In some embodiments, the antigen binding construct can include SEQ ID NO: 13 (See FIG. 12). In some embodiments, the polypeptide of the monomer includes a sequence with least about 80% identity, for example at least about 80%, 85%, 86%, 87%, 88%, 89%, 90%, 91%, 92%, 93, 94, 95%, 96%, 97%, 98%, 99%, or 100% identity to SEQ ID NO: 13.

In some embodiments, the CDR sequences (e.g., as denoted in FIGS. 20 and 21) are maintained and the rest of the sequence is allowed to vary.

In some embodiments, the antigen binding construct can include SEQ ID NO: 14 (See FIG. 13). In some embodiments, the polypeptide of the monomer includes a sequence with least about 80% identity, for example at least about 80%, 85%, 86%, 87%, 88%, 89%, 90%, 91%, 92%, 93, 94, 95%, 96%, 97%, 98%, 99%, or 100% identity to SEQ ID NO: 14.

In some embodiments, the CDR sequences (e.g., as denoted in FIGS. 20 and 21) are maintained and the rest of the sequence is allowed to vary.

In some embodiments, the antigen binding construct can include SEQ ID NO: 15 (See FIG. 14). In some embodiments, the polypeptide of the monomer includes a sequence with least about 80% identity, for example at least about 80%, 85%, 86%, 87%, 88%, 89%, 90%, 91%, 92%, 93, 94, 95%, 96%, 97%, 98%, 99%, or 100% identity to SEQ ID NO: 15.

In some embodiments, the CDR sequences (e.g., as denoted in FIGS. 20 and 21) are maintained and the rest of the sequence is allowed to vary.

In some embodiments, the antigen binding construct can include SEQ ID NO: 16 (See FIG. 15). In some embodiments, the polypeptide of the monomer includes a sequence with least about 80% identity, for example at least about 80%, 85%, 86%, 87%, 88%, 89%, 90%, 91%, 92%, 93, 94, 95%, 96%, 97%, 98%, 99%, or 100% identity to SEQ ID NO: 16.

In some embodiments, the CDR sequences (e.g., as denoted in FIGS. 20 and 21) are maintained and the rest of the sequence is allowed to vary.

In some embodiments, the antigen binding construct can include SEQ ID NO: 17 (See FIG. 16). In some embodiments, the polypeptide of the monomer includes a sequence with least about 80% identity, for example at least about 80%, 85%, 86%, 87%, 88%, 89%, 90%, 91%, 92%, 93, 94, 95%, 96%, 97%, 98%, 99%, or 100% identity to SEQ ID NO: 17.

In some embodiments, the CDR sequences (e.g., as denoted in FIGS. 20 and 21) are maintained and the rest of the sequence is allowed to vary.

In some embodiments, the antigen binding construct can include SEQ ID NO: 18 (See FIG. 17). In some embodiments, the polypeptide of the monomer includes a sequence with least about 80% identity, for example at least about 80%, 85%, 86%, 87%, 88%, 89%, 90%, 91%, 92%, 93, 94, 95%, 96%, 97%, 98%, 99%, or 100% identity to SEQ ID NO: 18.

In some embodiments, the CDR sequences (e.g., as denoted in FIGS. 20 and 21) are maintained and the rest of the sequence is allowed to vary.

In some embodiments, the cysteines are cross-linked with one another. In some embodiments, the cysteines are reduced, and thus, these tails forming cysteines do not form a disulfide bond with one another. In some embodiments, one or more of the "tail forming" cysteines form a covalent bond with one or more detectable marker, such as a fluorescent probe.

As will be appreciated by those of skill in the art, while the present disclosure generally references "cys-diabodies" alternative arrangements can be employed to achieve the same or similar ends. In some embodiments, any covalently modifiable moiety can be employed in place of one or more of the cysteines. For example, this can include a GlySer linker, a GlyLeu linker, and/or an insert cysteine after a short tag. In some embodiments, the connection can be established via a coiled coil or a leucine zipper. In some embodiments, the "tail" itself can include functional groups on its end so that it can selectively bind to a desired residue and/or location at the ends of each of the polypetides, in place of the disulfide bond itself. In some embodiments, rather than the tail providing space between the two polypeptide chains, the covalently modifiable moieties can be attached directly to the end of the heavy or light chain polypeptide, but the two covalently modifiable moieties can be connected by a linker.

In some embodiments, a chimeric cys-diabody that binds to the target molecule is provided. In some embodiments, the chimeric cys-diabody includes a monomer in the $V_L$-$V_H$ format, and includes the sequence of SEQ ID NOs: 11, 12, 13, or 14, or a sequence having at least about 80% identity thereto, for example at least about 80%, 85%, 90%, 95%, 96%, 97%, 98%, or 99% identity thereto. In some embodiments, the chimeric cys-diabody includes a monomer in the $V_H$-$V_L$ format, and includes the sequence of SEQ ID NOs: 15, 16, 17, or 18, or a sequence having at least about 80% identity thereto, for example at least about 80%, 85%, 90%, 95%, 96%, 97%, 98%, or 99%% identity thereto. In some embodiments, the CDR sequences (e.g., as denoted in FIGS. 20 and 21) are maintained and the rest of the sequence is allowed to vary.

In some embodiments, any of the constructs provided herein (including those arrangements noted as cys-diabody embodiments, can be provided as a scFv embodiment. In such embodiments, the construct can still include the cysteine on the tail, but simply not be cross-linked. In other embodiments, the construct need not have the cysteine in a tail or the tail at all.

Linker and/or Tail Options

In some embodiments, for individual antibodies, the heavy and light chain variable domains can associate in different ways. For this reason, the use of different linker lengths allows for conformational flexibility and range-of-motion to ensure formation of the disulfide bonds.

In some embodiments, the two linker lengths can be somewhere between (and including) about 1 to 50 amino acids, for example, 2 to 15, 2 to 14, 3 to 13, 4 to 10, or 5 amino acids to 8 amino acids. In some embodiments, each linker within a pair for a diabody can be the same length. In some embodiments, each linker within the pair can be a different length. In some embodiments, any combination of linker length pairs can be used, as long as they allow and/or promote the desired combinations. In some embodiments, a modified amino acid can be used.

In some embodiments, the linker is a GlySer linker. The GlySer linker can be a polypeptide that is rich in Gly and/or Ser residues. In some embodiments, at least about 40% of the amino acid residues of the GlySer linker are Gly, Ser, or a combination of Gly and Ser, for example at least about 40%, 50%, 60%, 70%, 80%, or 90%. In some embodiments, the GlySer linker is at least about 2 amino acids long, for example at least about 3, 4, 5, 6, 7, 8, 9, 10, 11, 12, 13, 14, 15, 16, 17, 18, 19, 20, 25, 30, 35, or 40 amino acids long.

In some embodiments, a cysteine is added at the C-terminus of the diabody. This cysteine can allow the diabody complex to form covalent cysteine bonds and provides the option for available sulfur residues for site-specific conjugation of functional moieties such as radiolabels. In some embodiments, a terminal end of the antibody itself is altered so as to contain a cysteine. In some embodiments, a tail sequence, for example (Gly-Gly-Cys) is added at the C-terminus. In some embodiments, the cysteine tail sequence allows two monomers of a cys-diabody to form disulfide bonds with each other. In some embodiments, the cysteine tail sequence allows a cys-diabody to form disulfide linkages with a detectable moiety such as a detectable marker and/or therapeutic agent. The sulfhydryl groups of the cysteine tail can undergo mild reduction prior to site-specific conjugation of a desired functional moiety, for example a detectable marker and/or therapeutic agent. In some embodiments, the tail is at least about 1 amino acid long, for example at least about 1, 2, 3, 4, 5, 6, 7, 8, 9, 10, 11, 12, 13, 14, 15, 16, 17, 18, 19, 20, 25, 30, 35, or 40 amino acids long.

In some embodiments, the tail is 3 to 8 amino acids in length. In some embodiments, the tail can and/or include a coiled coil and/or a leucine zipper. As noted above, in some embodiments, the cysteine is located at the c-terminus; however, this does not require that the cysteine be located as the last c-terminal amino acid. Instead, this denotes that the cysteine can be part of any of the residues that are located in the C-terminus of the protein.

In some embodiments, the linking option between the two C-terminuses can be achieved by a cysteine, for direct and/or indirect, cross-linking.

Minibodies

In some embodiments, the antigen binding construct comprises a minibody including the amino acid sequence in SEQ ID NO: 5. In some embodiments, the minibody is at least 70. 75, 80, 85, 90, 95, 96, 97, 98, 99, 99.5, or 100% identical to the noted sequence. In some embodiments, the CDRs are conserved while the other residues change. In some embodiments, 1, 2, 3, 4, 5 residues in 1, 2, 3, 4, 5, or 6 of the CDRs can be varied. In some embodiments, the minibody comprises one or more of the amino acids shown in any one or more of FIGS. 5-8.

In some embodiments, the antigen binding construct comprises a minibody including the amino acid sequence in SEQ ID NOs: 2 and/or 4. In some embodiments, the minibody is at least 70. 75, 80, 85, 90, 95, 96, 97, 98, 99, 99.5, or 100% identical to the noted sequence. In some embodiments, the CDRs are conserved while the other residues change. In some embodiments, 1, 2, 3, 4, 5 residues in 1, 2, 3, 4, 5, or 6 of the CDRs can be varied. In some embodiments, any of the embodiments in a)-n) denoted herein can be employed as a minibody arrangement.

In some embodiments, the antigen binding construct comprises a minibody including the amino acid sequence in SEQ ID NO: 6. In some embodiments, the minibody is at least 70. 75, 80, 85, 90, 95, 96, 97, 98, 99, 99.5, or 100% identical to the noted sequence. In some embodiments, the CDRs are conserved while the other residues change. In some embodiments, 1, 2, 3, 4, 5 residues in 1, 2, 3, 4, 5, or 6 of the CDRs can be varied.

In some embodiments, the antigen binding construct comprises a minibody including the amino acid sequence in SEQ ID NO: 7. In some embodiments, the minibody is at least 70. 75, 80, 85, 90, 95, 96, 97, 98, 99, 99.5, or 100% identical to the noted sequence. In some embodiments, the CDRs are conserved while the other residues change. In some embodiments, 1, 2, 3, 4, 5 residues in 1, 2, 3, 4, 5, or 6 of the CDRs can be varied.

In some embodiments, the antigen binding construct comprises a minibody including the amino acid sequence in SEQ ID NO: 8. In some embodiments, the minibody is at least 70. 75, 80, 85, 90, 95, 96, 97, 98, 99, 99.5, or 100% identical to the noted sequence. In some embodiments, the CDRs are conserved while the other residues change. In some embodiments, 1, 2, 3, 4, 5 residues in 1, 2, 3, 4, 5, or 6 of the CDRs can be varied.

A "minibody" as described herein includes a homodimer, wherein each monomer is a single-chain variable fragment (scFv) linked to a human IgG1 $C_H3$ domain by a linker, such as a hinge sequence. In some embodiments, the hinge sequence is a human IgG1 hinge sequence as shown in FIG. 18, SEQ ID NOs: 34-37. In some embodiments, the hinge sequence is at least 80, 85, 90, 95, 99 or 100% identical to one or more of the sequences in FIG. 18. In some embodiments, the CDR sequences (e.g., as denoted in FIGS. 19 and 20 or FIG. 4) are maintained and the rest of the sequence is allowed to vary.

In some embodiments, the hinge sequence is an artificial hinge sequence. In some embodiments, the hinge sequence can be an IgG hinge from any one or more of the four classes. The artificial hinge sequence may include a portion of a human IgG1 hinge and a GlySer linker sequence. Suitable hinge sequences may also be found as published in WIPO patent publication WO2017027325, hereby incorporated by reference in its entirety.

In some embodiments, the artificial hinge sequence includes approximately the first 14 or 15 residues of the human IgG1 hinge followed by a linker sequence. In some embodiments, the linker can be any of those provided herein. In some embodiments, the linker can be a GlySer linker sequence that is 6, 7, 8, 9 or 10 amino acids in length. In some embodiments, the artificial hinge sequence includes approximately the first 15 residues of the IgG1 hinge followed by a GlySer linker sequence that is about 10 amino acids in length. In some embodiments, association between the $C_H3$ domains causes the minibody to exist as a stable dimer.

In some embodiments, the minibody scFv sequence can include CDR and/or FR, and or variable region sequences that are similar and/or the same to a diabody sequence described herein. In some embodiments, the minibody scFv has a sequence (CDR, CDRs, full set of 6 CDRS, heavy chain variable region, light chain variable region, heavy and light chain variable regions, etc.) that is at identical to a scFv of a cys-diabody described herein.

In some embodiments, the minibody has a variable chain region that is at least about 80% identical to a minibody sequence provided herein. The scFv can have a $V_H$-$V_L$ or a $V_L$-$V_H$ orientation. In some embodiments, the $V_H$ and $V_L$ are linked to each other by an amino acid linker sequence. The amino acid linker can be a linker as described herein. In some embodiments, the linker is GlySer-rich and approximately 15-20 amino acids in length. In another embodiment, the linker is GlySer rich and is 18 amino acids in length. In some embodiments, the linker length varies between (and including) about 1 to 50 amino acids, for example, 2 to 30, 3 to 20, 4 to 15, or 5 amino acids to 8 amino acids. In some embodiments, the minibody scFv has a sequence that is at least about 80% identical to a scFv of a cys-diabody described herein, for example at least about 80%, 85%, 86%, 87%, 88%, 89%, 90%, 91%, 92%, 93, 94, 95%, 96%, 97%, 98%, or 99% identity. The scFv can have a $V_H V_L$ or a $V_L V_H$ orientation.

In some embodiments, each monomer of the minibody includes the following elements, from N-terminus to C-terminus: (a) an scFv sequence that includes a $V_H$ domain linked to a $V_L$ domain and that binds to the target molecule, (b) a hinge-extension domain comprising a human IgG1 hinge region, and (c) a human IgG $C_H3$ sequence. In some embodiments, each monomer of the minibody includes an IgG2, an IgG3, or an IgG4 $C_H3$. In some embodiments, the minibody is encoded by a nucleic acid that can be expressed by a cell, a cell line or other suitable expression system as described herein. Thus, a signal sequence can be fused to the N-terminus of the scFv to enable secretion of the minibody when expressed in the cell or cell line.

Nucleic Acids

In some embodiments, the polypeptides of the antigen binding constructs can be encoded by nucleic acids and expressed in vivo or in vitro, or these peptides can be synthesized chemically. Thus, in some embodiments, a nucleic acid encoding an antigen binding construct is provided. In some embodiments, the nucleic acid encodes one part or monomer of a cys-diabody or minibody. In some embodiments, the nucleic acid encodes two or more monomers, for example, at least 2 monomers. Nucleic acids encoding multiple monomers can include nucleic acid cleavage sites between at least two monomers, can encode transcription or translation start site between two or more monomers, and/or can encode proteolytic target sites between two or more monomers.

In some embodiments, an expression vector contains a nucleic acid encoding an antigen binding construct as disclosed herein. In some embodiments, the expression vector includes pcDNA3.1™/myc-His (−) Version A vector for mammalian expression (Invitrogen, Inc.), or a variant thereof. The pcDNA3.1 expression vector features a CMV promoter for mammalian expression and both mammalian (Neomycin) and bacterial (Ampicillin) selection markers. In some embodiments, the expression vector includes a plasmid. In some embodiments, the vector includes a viral vector, for example a retroviral or adenoviral vector. In embodiments, the vector includes a cosmid, YAC, or BAC.

In some embodiments, the nucleotide sequence encoding at least one of the minibody monomers comprises at least one of SEQ ID NOs: 9 and 10. In some embodiments, the nucleotide sequence can be one that encodes any one of the antigen binding constructs provided herein. In some embodiments, the sequence is one that hybridizes to SEQ ID Nos: 9 and/or 10 under stringent conditions.

Cell Lines

In some embodiments, a cell line is provided that expresses at least one of the antigen binding constructs described herein. In some embodiments, a mammalian cell line (e.g., CHO-K1 cell line) is an expression system to produce the minibodies, cys-diabodies or other antibodies as described herein. In some embodiments, the minibodies, cys-diabodies and other antibodies or antibody fragments described herein are non-glycosylated, and a mammalian expression system is not required, as such post-translational modifications are not needed. Thus, in some embodiments, one or more of a wide variety of mammalian or non-mammalian expression systems are used to produce the antigen binding constructs disclosed herein (for example, anti-CD4 minibodies and cys-diabodies) including, but not limited to mammalian expression systems (e.g., CHO-K1 cells), bacterial expression systems (e.g., *E. coli, B. subtilis*) yeast expression systems (e.g., *Pichia, S. cerevisiae*) or any other known expression system, including cell free expression systems (Shaorong C.; Curr Protoc Mol Biol. (2014); 108: 16.30.1-16.30.11.). Other systems can include insect cells and/or plant cells.

Antigen Binding Construct Modifications

In some embodiments, the antigen binding construct includes at least one modification. Exemplary modifications include, but are not limited to, antigen binding constructs that have been modified by glycosylation, acetylation, pegylation, phosphorylation, amidation, derivatization by known protecting/blocking groups, proteolytic cleavage, and linkage to a cellular ligand or other protein. Any of numerous chemical modifications may be carried out by known techniques, including, but not limited to, specific chemical cleavage, acetylation, formylation and metabolic synthesis of tunicamycin. In some embodiments, the derivative can contain one or more non-natural amino acids.

In some embodiments, the antigen binding construct is conjugated to another substance to form an anti-target conjugate. The conjugates described herein can be prepared by known methods of linking antigen binding constructs with lipids, carbohydrates, protein or other atoms and molecules. In some embodiments, the conjugate is formed by site-specific conjugation using a suitable linkage or bond. Site-specific conjugation is more likely to preserve the binding activity of an antigen binding construct. The substance may be conjugated or attached at the hinge region of a reduced antigen binding construct via disulfide bond formation. For example, introduction of cysteine residues at the C-terminus of a scFv fragment, such as those that can be introduced in the cys-diabodies described herein, allows site-specific thiol-reactive coupling at a site away from the antigen binding site to a wide variety of agents. Other linkages or bonds used to form the conjugate can include, but are not limited to, a covalent bond, a non-covalent bond, a sulfide linkage, a hydrazone linkage, a hydrazine linkage, an ester linkage, an amido linkage, and amino linkage, an imino linkage, a thiosemicabazone linkage, an emicarbazone linkage, an oxime linkage and a carbon-carbon linkage.

Detectable Markers

In some embodiments, a modified antigen binding construct is conjugated to a detectable marker. As used herein, a "detectable marker" includes an atom, molecule, or compound that is useful in diagnosing, detecting or visualizing a location and/or quantity of a target molecule, cell, tissue, organ and the like. Detectable markers that can be used in accordance with the embodiments herein include, but are not limited to, radioactive substances (e.g., radioisotopes, radionuclides, radiometals, radiolabels or radiotracers), dyes, contrast agents, fluorescent compounds or molecules, bioluminescent compounds or molecules, enzymes and enhancing agents (e.g., paramagnetic ions). In addition, some nanoparticles, for example quantum dots and metal nanoparticles (described below) can be suitable for use as a detection agent. In some embodiments, the detectable marker is Indo-Cyanine Green (ICG).

Exemplary radioactive substances that can be used as detectable markers in accordance with the embodiments herein include, but are not limited to, $^{18}$F, $^{18}$F-FAC, $^{32}$P, $^{33}$P, $^{45}$Ti, $^{47}$Sc, $^{52}$Fe, $^{59}$Fe, $^{62}$Cu, $^{64}$Cu, $^{67}$Cu, $^{67}$Ga, $^{68}$Ga, $^{75}$Sc, $^{77}$As, $^{86}$Y, $^{90}$Y, $^{89}$Sr, $^{89}$Zr, $^{94}$Tc, $^{94}$Tc, $^{99}$mTc, $^{99}$Mo, $^{105}$Pd, $^{105}$Rh, $^{111}$Ag, $^{111}$In, $^{123}$I, $^{124}$I, $^{125}$I, $^{131}$I, $^{142}$Pr, $^{143}$Pr, $^{149}$Pm, $^{153}$Sm, $^{154-158}$Pb, $^{212}$Tb, $^{166}$Dy, $^{166}$Ho, $^{169}$Er, $^{175}$Lu, $^{177}$Lu, $^{186}$Re, $^{188}$Re, $^{189}$Re, $^{194}$Ir, $^{198}$Au, $^{199}$Au, $^{211}$At, $^{211}$Pb, $^{212}$Bi, $^{212}$Pb, $^{213}$Bi, $^{223}$Ra, $^{225}$Ac, and $^{227}$Th. Exemplary Paramagnetic ions substances that can be used as detectable markers include, but are not limited to ions of transition and lanthanide metals (e.g. metals having atomic numbers of 6 to 9, 21-29, 42, 43, 44, or 57-71). These metals include ions of Cr, V, Mn, Fe, Co, Ni, Cu, La, Ce, Pr, Nd, Pm, Sm, Eu, Gd, Tb, Dy, Ho, Er, Tm, Yb and Lu. In some embodiments, the antigen binding construct of can be linked to a detectable marker that is a positron (β+) emitter, optionally at least one of $^{18}$F, $^{89}$Zr, $^{68}$Ga and $^{64}$Cu, optionally at least one of $^{18}$F or $^{89}$Zr.

When the detectable marker is a radioactive metal or paramagnetic ion, in some embodiments, the marker can be reacted with a reagent having a long tail with one or more chelating groups attached to the long tail for binding these ions. The long tail can be a polymer such as a polylysine, polysaccharide, or other derivatized or derivatizable chain having pendant groups to which may be bound to a chelating group for binding the ions. Examples of chelating groups that may be used according to the embodiments herein include, but are not limited to, ethylenediaminetetraacetic acid (EDTA), diethylenetriaminepentaacetic acid (DTPA), DOTA, NOTA, NOGADA, NETA, deferoxamine (DfO), porphyrins, polyamines, crown ethers, bis-thiosemicarbazones, polyoximes, and like groups. The chelate can be linked to the antigen binding construct by a group which allows formation of a bond to the molecule with minimal loss of immunoreactivity and minimal aggregation and/or internal cross-linking. The same chelates, when complexed with non-radioactive metals, such as manganese, iron and gadolinium are useful for MRI, when used along with the antigen binding constructs and carriers described herein. Macrocyclic chelates such as NOTA, NOGADA, DOTA, and TETA are of use with a variety of metals and radiometals including, but not limited to, radionuclides of gallium, yttrium and copper, respectively. Other ring-type chelates such as macrocyclic polyethers, which are of interest for stably binding radionuclides, such as Radium-223 for RAIT may be used. In certain embodiments, chelating moieties may be used to attach a PET imaging agent, such as an Aluminum-$^{18}$F complex, to a targeting molecule for use in PET analysis. In some embodiments, one or more of the antigen binding constructs can be used for SPECT-single photon imaging. In some embodiments, the antigen binding construct can be associated with technetium. In some embodiments, the antigen binding construct can be associated with PET isotopes. In some embodiments, the antigen binding construct can be used in Cerenkov imaging.

Exemplary contrast agents that can be used as detectable markers in accordance with the embodiments of the disclosure include, but are not limited to, barium, diatrizoate, ethiodized oil, gallium citrate, iocarmic acid, iocetamic acid, iodamide, iodipamide, iodoxamic acid, iogulamide, iohexyl, iopamidol, iopanoic acid, ioprocemic acid, iosefamic acid, ioseric acid, iosulamide meglumine, iosemetic acid, iotasul, iotetric acid, iothalamic acid, iotroxic acid, ioxaglic acid, ioxotrizoic acid, ipodate, meglumine, metrizamide, metrizoate, propyliodone, thallous chloride, or combinations thereof.

Bioluminescent and fluorescent compounds or molecules and dyes that can be used as detectable markers in accordance with the embodiments of the disclosure include, but are not limited to, fluorescein, fluorescein isothiocyanate (FITC), OREGON GREEN™ rhodamine, Texas red, tetrarhodimine isothiocynate (TRITC), Cy3, Cy5, and the like), fluorescent markers (e.g., green fluorescent protein (GFP), phycoerythrin, and the like), autoquenched fluorescent compounds that are activated by tumor-associated proteases, enzymes (e.g., luciferase, horseradish peroxidase, alkaline phosphatase, and the like), fluorescent compounds that are sensitive to environment (e.g pH sensitive and activated probes) nanoparticles, biotin, digoxigenin or combination thereof. In some embodiments, fluorescence can be used for photoacoustic imaging and/or photodynamic therapy.

Enzymes that can be used as detectable markers in accordance with the embodiments of the disclosure include, but are not limited to, horseradish peroxidase, alkaline phosphatase, acid phosphatase, glucose oxidase, β-galactosidase, β-glucoronidase or β-lactamase. Such enzymes may be used in combination with a chromogen, a fluorogenic compound or a luminogenic compound to generate a detectable signal.

In some embodiments, the antigen binding construct is conjugated to a nanoparticle. The term "nanoparticle" refers to a microscopic particle whose size is measured in nanometers, e.g., a particle with at least one dimension less than about 100 nm. Nanoparticles can be used as detectable substances because they are small enough to scatter visible light rather than absorb it. For example, gold nanoparticles possess significant visible light extinction properties and appear deep red to black in solution. As a result, compositions comprising antigen binding constructs conjugated to nanoparticles can be used for the in vivo imaging of T-cells in a subject. At the small end of the size range, nanoparticles are often referred to as clusters. Metal, dielectric, and semiconductor nanoparticles have been formed, as well as hybrid structures (e.g. core-shell nanoparticles). Nanospheres, nanorods, and nanocups are just a few of the shapes that have been grown. Semiconductor quantum dots and nanocrystals are examples of additional types of nanoparticles. Such nanoscale particles, when conjugated to an antigen binding construct, can be used as imaging agents for the in vivo detection of T-cells as described herein. In some embodiments, the antigen binding construct is conjugated or contained in or within particles and/or liposomes. In some embodiments, the liposomes can be used for ultrasound imaging.

Therapeutic Agents

In some embodiments, an antigen binding construct is conjugated to a therapeutic agent. A "therapeutic agent" as used herein is an atom, molecule, or compound that is useful in the treatment of cancer, inflammation, other disease conditions, or to otherwise suppress an immune response, for example immunosuppression in organ transplants. Examples of therapeutic agents include, but are not limited to, drugs, chemotherapeutic agents, therapeutic antibodies and antibody fragments, toxins, radioisotopes, enzymes (e.g., enzymes to cleave prodrugs to a cytotoxic agent at the site of the antigen binding construct binding), nucleases, hormones, immunomodulators, antisense oligonucleotides, chelators, boron compounds, photoactive agents and dyes, and nanoparticles.

When bound to a therapeutic agent, the antigen binding constructs can be used to target diseases associated with cells that present CD4 antigens, or diseases which attract CD4+ T-cells. These diseases include neoplasms such as solid tumors, and cancers derived from T helper cells, including but not limited to peripheral T cell lymphoma and related malignant conditions. The CD4 antigen has also been associated with a number of autoimmune diseases such as vitiligo, type I diabetes mellitus, Rheumatoid Arthritis, Crohn's disease, inflammatory bowel disease, Ulcerative colitis. The CD4 antigen has also been associated with a number of neurodegenerative disorders such Parkinson's disease and Multiple Sclerosis. The CD4 antigen has also been associated with a number of cardiovascular diseases, such as Ischemic Heart Failure. The CD4 antigen has also been associated with Human Immunodeficiency Virus (HIV) and Graft vs Host Disease (GvHD). Selective targeting of CD4-bearing cells with therapeutic agents may also have an impact on autoinflammatory diseases.

Chemotherapeutic agents are often cytotoxic or cytostatic in nature and may include alkylating agents, antimetabolites, anti-tumor antibiotics, topoisomerase inhibitors, mitotic inhibitors hormone therapy, targeted therapeutics and immunotherapeutics. In some embodiments the chemotherapeutic agents that may be used as detectable markers in accordance with the embodiments of the disclosure include, but are not limited to, 13-cis-Retinoic Acid, 2-Chlorodeoxyadenosine, 5-Azacitidine, 5-Fluorouracil, 6-Mercaptopurine, 6-Thioguanine, actinomycin-D, adriamycin, aldesleukin, alemtuzumab, alitretinoin, all-transretinoic acid, alpha interferon, altretamine, amethopterin, amifostine, anagrelide, anastrozole, arabinosylcytosine, arsenic trioxide, amsacrine, aminocamptothecin, aminoglutethimide, asparaginase, azacytidine, bacillus calmette-guerin (BCG), bendamustine, bevacizumab, bexarotene, bicalutamide, bortezomib, bleomycin, busulfan, calcium leucovorin, citrovorum factor, capecitabine, canertinib, carboplatin, carmustine, cetuximab, chlorambucil, cisplatin, cladribine, cortisone, cyclophosphamide, cytarabine, darbepoetin alfa, dasatinib, daunomycin, decitabine, denileukin diftitox, dexamethasone, dexasone, dexrazoxane, dactinomycin, daunorubicin, decarbazine, docetaxel, doxorubicin, doxifluridine, eniluracil, epirubicin, epoetin alfa, erlotinib, everolimus, exemestane, estramustine, etoposide, filgrastim, fluoxymesterone, fulvestrant, flavopiridol, floxuridine, fludarabine, fluorouracil, flutamide, gefitinib, gemcitabine, gemtuzumab ozogamicin, goserelin, granulocyte-colony stimulating factor, granulocyte macrophage-colony stimulating factor, hexamethylmelamine, hydrocortisone hydroxyurea, ibritumomab, interferon alpha, interleukin-2, interleukin-11, isotretinoin, ixabepilone, idarubicin, imatinib mesylate, ifosfamide, irinotecan, lapatinib, lenalidomide, letrozole, leucovorin, leuprolide, liposomal Ara-C, lomustine, mechlorethamine, megestrol, melphalan, mercaptopurine, mesna, methotrexate, methylprednisolone, mitomycin C, mitotane, mitoxantrone, nelarabine, nilutamide, octreotide, oprelvekin, oxaliplatin, paclitaxel, pamidronate, pemetrexed, panitumumab, PEG Interferon, pegaspargase, pegfilgrastim, PEG-L-asparaginase, pentostatin, plicamycin, prednisolone, prednisone, procarbazine, raloxifene, rituximab, romiplostim, ralitrexed, sapacitabine, sargramostim, satraplatin, sorafenib, sunitinib, semustine, streptozocin, tamoxifen, tegafur, tegafur-uracil, temsirolimus, temozolamide, teniposide, thalidomide, thioguanine, thiotepa, topotecan, toremifene, tositumomab, trastuzumab, tretinoin, trimitrexate, alrubicin, vincristine, vinblastine, vindestine, vinorelbine, vorinostat, or zoledronic acid.

Additional detectable markers that can be used in accordance with the embodiments of the disclosure include, but are not limited to, ricin, abrin, ribonuclease (RNase), DNase I, Staphylococcal enterotoxin-A, pokeweed antiviral protein, gelonin, diphtheria toxin, Pseudomonas exotoxin, and Pseudomonas endotoxin.

In some embodiments, nanoparticles, particles, and/or liposomes are used in therapeutic applications as drug carriers that, when conjugated to an antigen binding construct, deliver chemotherapeutic agents, hormonal therapeutic agents, radiotherapeutic agents, toxins, or any other cytotoxic or anti-cancer agent known in the art to cancerous cells that overexpress the target on the cell surface.

Kits

In some embodiments, kits are provided. In some embodiments, the kit includes an antigen binding construct as described herein. In some embodiments, the kit includes a nucleic acid that encodes an antigen binding construct as described herein. In some embodiments, the kit includes a cell line that produces an antigen binding construct as described herein. In some embodiments, the kit includes a detectable marker as described herein. In some embodiments, the kit includes a therapeutic agent as described herein. In some embodiments, the kit includes buffers. In some embodiments, the kit includes positive controls, for example CD4, CD4+ cells, or fragments thereof. In some embodiments, the kit includes negative controls, for example a surface or solution that is substantially free of CD4. In some embodiments, the kit includes packaging. In some embodiments, the kit includes instructions.

Methods of Detecting the Presence or Absence of the Target Molecule

In some embodiments, antigen binding constructs can be used to detect the presence or absence of the target molecule in vivo and/or in vitro. Accordingly, some embodiments include methods of detecting the presence or absence of the target. The method can include applying an antigen binding construct to a sample. The method can include detecting a binding or an absence of binding of the antigen binding construct to the target molecule, CD4. In some embodiments, the antigen binding construct with a detectable marker can be applied to simply monitor CD4 levels and/or distribution. In some embodiments, it can be applied to a subject that has or is suspected of having a CD4 related disease or disorder. These diseases can include neoplasms such solid tumors, and cancers derived from T helper cells, including but not limited to peripheral T cell lymphoma and related malignant conditions. The diseases can also include autoimmune diseases such as vitiligo, type I diabetes mellitus, Rheumatoid Arthritis, Crohn's disease, inflammatory bowel disease, Ulcerative colitis. The diseases can also include neurodegenerative disorders such Parkinson's disease and Multiple Sclerosis; and cardiovascular diseases, such as Ischemic Heart Failure; and Human Immunodeficiency Virus (HIV) and Graft vs Host Disease (GvHD).

In some embodiments, an antigen binding construct as described herein is applied to a sample in vivo. The antigen binding construct can be administered to a subject. In some embodiments, the subject is a human. In some embodiments, the subject is a non-human mammal, for example a rat, mouse, guinea pig, hamster, rabbit, dog, cat, cow, horse, goat, sheep, donkey, pig, monkey, or ape. In some embodiments, the antigen binding construct is infused into the subject. In some embodiments, the infusion is intravenous. In some embodiments, the infusion is intraperitoneal. In some embodiments, the antigen binding construct is applied topically or locally (as in the case of an interventional or intraoperative application) to the subject. In some embodiments, a capsule containing the antigen binding construct is applied to the subject, for example orally or intraperitoneally. In some embodiments, the antigen binding construct is selected to reduce the risk of an immunogenic response by subject. For example, for a human subject, the antigen binding construct can be humanized as described herein. In some embodiments, following in vivo application of the antigen binding construct, the sample, or a portion of the sample is removed from the host. In some embodiments, the antigen binding construct is applied in vivo, is incubated in vivo for a period of time as described herein, and a sample is removed for analysis in vitro, for example in vitro detection of antigen binding construct bound to the target molecule or the absence thereof as described herein.

In some embodiments, the antigen binding construct is applied to a sample in vitro. In some embodiments, the sample is freshly harvested from a subject, for example a biopsy. In some embodiments, the sample is incubated following harvesting from a subject. In some embodiments, the sample is fixed. In some embodiments the sample includes a whole organ and/or tissue. In some embodiments, the sample includes one or more whole cells. In some embodiments the sample is from cell extracts, for example lysates. In some embodiments, antigen binding construct in solution is added to a solution in the sample. In some embodiments, antigen binding construct in solution is added to a sample that does not contain a solution, for example a lyophilized sample, thus reconstituting the sample. In some embodiments, lyophilized antigen binding construct is added to a sample that contains solution, thus reconstituting the antigen binding construct.

In some embodiments, the antigen binding construct is optionally incubated with the sample. The antigen binding construct can be incubated for a period of no more than about 10 days, for example no more than about 10 days, 9, 8, 7, 6, 5, 4, 3, 2, or 1 day, or no more than about 23 hours, for example no more than about 23 hours, 22, 21, 20, 19, 18, 17, 16, 15, 14, 13, 12, 11, 10, 9, 8, 7, 6, 5, 4, 3, 2, 1, 0.75, 0.5, 0.25, or 0.1 hour, including ranges between any two of the listed values. In some embodiments, the incubation is within a subject to which the antigen binding construct was administered. In some embodiments, the incubation is within an incubator. In some embodiments, the incubator is maintained at a fixed temperature, for example about 21° C., room temperature, 25° C., 29° C., 34° C., 37° C., or 40° C.

In some embodiments, the antigen binding construct that is not bound to the target is optionally removed from the sample. In some embodiments, the sample is washed. Washing a sample can include removing solution that contains unbound antigen binding construct, and adding solution that does not contain antigen binding construct, for example buffer solution. In some embodiments, an in vitro sample is washed, for example by aspirating, pipetting, pumping, or draining solution that contains unbound antigen binding construct, and adding solution that does not contain antigen binding construct. In some embodiments, an in vivo sample is washed, for example by administering to the subject solution that does not contain antigen binding construct, or by washing a site of topical antigen binding construct administration. In some embodiments, the wash is performed at least two times, for example at least 2, 3, 4, 5, 6, 7, 8, 9, 10, 15, or 20 times. In some embodiments, following the wash or washes, at least about 50% of unbound antibody is removed from the sample, for example at least about 50%, 60%, 70%, 75%, 80%, 85%, 90%, 95%, 97%, 98%, 99% or greater.

In some embodiments, unbound antigen binding construct is eliminated from the sample. Following application of the antigen binding construct to the sample, antigen binding construct bound to the target reaches an equilibrium with antigen binding construct unbound to the target, so that at some time after application of the antigen binding construct, the amount of antigen binding construct bound to the target does not substantially increase. After this time, at least part of the quantity of the antigen binding construct that is unbound to the target can be eliminated. In some embodiments, unbound antigen binding construct is eliminated by metabolic or other bodily processes of the subject to whom the antibody or fragment was delivered. In some embodiments, unbound antigen binding construct is eliminated by the addition of an agent that destroys or destabilized the unbound antigen binding construct, for example a protease or a neutralizing antibody. In some embodiments, 1 day after application of the antigen binding construct, at least about 30% of the antigen binding construct that was applied has been eliminated, for example at least about 30%, 40%, 60%, 70%, 75%, 80%, 85%, 90%, 95%, 97%, 98%, 99%, or 99.9%. In some embodiments, 2 days after application of the antigen binding construct, at least about 40% of the antigen binding construct that was applied has been eliminated, for example at least about 40%, 50%, 60%, 70%, 75%, 80%, 85%, 90%, 95%, 97%, 98%, 99%, or 99.9%.

In some embodiments, the presence or absence of the target, CD4, is detected. The presence or absence of the target can be detected based on the presence or absence of the antigen binding construct in the sample. After removal and/or elimination of the antigen binding construct from the sample, for example by washing and/or metabolic elimination, remaining antigen binding construct in the sample can indicate the presence of the target, while an absence of the antigen binding construct in the sample can indicate the absence of the target.

In some embodiments, the antigen binding construct includes a detectable marker as described herein. Thus, the presence of the antigen binding construct can be inferred by detecting the detectable marker.

In some embodiments, a secondary antigen binding construct is used to detect the antigen binding construct. The secondary antigen binding construct can bind specifically to the antigen binding construct. For example, the secondary antigen binding construct can include a polyclonal or monoclonal antibody, diabody, minibody, etc. against the host type of the antibody, or against the antigen binding construct itself. The secondary antigen binding construct can be conjugated to a detectable marker as described herein. The secondary antigen binding construct can be applied to the sample. In some embodiments, the secondary antigen binding construct is applied to the sample in substantially the same manner as the antigen binding construct. For example, if the antigen binding construct was infused into a subject, the secondary antigen binding construct can also be infused into the subject.

In some situations, using full-length antibodies for imaging is not optimal as they can require imaging times to be scheduled more than 1 week after administration due to the long serum half-lives of full-length antibodies. Thus, in some embodiments, by using the antigen binding constructs provided herein, imaging times can be scheduled for less than a week after administration (e.g. 1, 2, 3, 4, 5, 6, or 7 days or fewer).

In some embodiments, the antigen binding constructs are useful for imaging T-cell localization for immunotherapy. This can especially relevant in adoptive immunotherapy, which is a form of therapy where a patient's own T-cells are manipulated in vitro and re-introduced into the patient. For this form of treatment, imaging of T-cells is useful for determining the status of the treatment. Thus, in some embodiments, the antigen binding constructs provided herein can be used in the imaging of T-cells in immunotherapy.

In some embodiments, the antigen binding constructs allow for the detection of human CD4, which is a specific biomarker found on the surface of a subset of T-cells, for diagnostic imaging of the immune system. Imaging of CD4 allows for the in vivo detection of T-cell localization. Changes in T-cell localization can reflect the progression of an immune response and can occur over time as a result of various therapeutic treatments or even disease states. In some embodiments, the presence CD4 contributes to the regulation of antitumor immune responses. The activation state of CD4 can play an important role in determining the outcome of the antitumor immune response.

An alternative target-based approach for imaging subtypes of immune cells involves small molecules is provided. For example, one approach for diagnostic imaging of the endogenous immune system has involved the use of small molecule tracers which detect changes in the cell's metabolic pathway such as $^{18}$F-fluoroacetate ([$^{18}$F]FAC). Since such tracers detect changes in the metabolic pathway, they target cell populations with elevated metabolic activities which primarily include activated T-cells. A limitation of this approach is that it will only detect the activated subset of T-cells, in contrast, imaging with anti-CD4 antibody fragments as provided herein will detect the entire population of CD4 expressing T-cells as the target is expressed on both activated and resting CD4 cells. In addition, another restriction on the other approaches is that it is limited to the extent that it is not T-cell specific.

In some embodiments, CD4 antibody-based imaging allows for the depiction of cell surface markers expressed on tumors in vivo. Various applications exist for these depictions, including primary and metastatic tumor detection, patient staging and stratification in treatment groups, determination of radioimmunotherapy dosing and receptor occupancy, and/or evaluation of response to therapy. In some embodiments, any of these methods or techniques can employ one or more of the antigen binding constructs provided herein.

Anti-CD4 immuno-positron emission tomography (PET) has the ability to monitor helper and cytotoxic T cell expansion and localization noninvasively and has the potential to detect enhanced T cell repopulation. Thus, in some embodiments, any one or more of the antigen binding constructs provided herein can be used for PET.

In some embodiments, a method is provided for monitoring a distribution of CD4 within a subject. The method can comprise providing any of the humanized minibodies or antigen binding constructs, or cys-diabodies provided herein (including one or more of SEQ ID Nos: 5-8, for example, 5). The construct can include a detectable marker, such as one or more of the positron emitters provided herein, $^{18}$F or $^{89}$Zr for example. In addition, the detectable marker can be linked to the antigen binding construct by, for example, deferoxamine (DfO). This labeled construct can be administered to the subject. Following administration of the labeled construct, a PET scan can be taken of the subject to determine a distribution of the labeled construct within the subject. This can then, optionally, be used to assist in diagnosing or treating the subject for a CD4 related disorder. In some embodiments, the PET scan is not a micro-PET scan.

In some embodiments, the humanized minibody or the antigen binding construct can be used as a medicament. In some embodiments, the humanized minibody or the antigen binding construct or the minibody or the cys-diabody can be for use in at least one of: detection, diagnosis, surgery, staging, treatment, monitoring of treatment, monitoring of disease progression, and monitoring therapy. In some embodiments, the humanized minibody or the antigen binding construct or the minibody or the cys-diabody can be for use in at least one of: detection, diagnosis, surgery, staging, treatment, monitoring of treatment, monitoring of disease progression, and monitoring therapy of a CD4 related disorder.

In some embodiments, binding or the absence of binding of the antigen binding construct is detected via positron emission tomography (PET).

Methods of Targeting a Therapeutic Agent to a Cell

Antigen binding constructs can be used to target a therapeutic molecule, for example a cytotoxin to a target positive cell, such as a cell expressing CD4. Thus, some embodiments include methods of targeting a therapeutic agent to a target positive cell. The method can include administering an antigen binding construct as described herein to a subject. The subject can be a subject in need, for example a subject in need of elimination or neutralization of at least some target positive cells. In some embodiments, the antigen binding construct includes at least on therapeutic agent as described herein. In some embodiments, the therapeutic can be directly conjugated to the antigen binding construct via a covalent bond, such as a disulfide bond. In some embodiments, the subject can benefit from the localization of a CD4 positive cell to another cell or agent.

Optionally, before and/or after administration of the antigen binding construct that includes at least one therapeutic agent, the number and/or localization of the target positive cells of the patient is determined. For example, determining the number and/or localization of target positive cells prior to administration can indicate whether the patient is likely to benefit from neutralization and/or elimination of the target positive cells. Determining the number and/or localization of the target positive cells after administration can indicate whether the target positive cells were eliminated in the patient.

In some embodiments, any of the antigen binding constructs provided herein can be used in a method of treating a subject. The method can comprise providing a subject suffering from a CD4 related disorder; and administering an effective amount of the antigen binding construct (as provided herein) to the subject so as to reduce at least one symptom from the CD4 related disorder. These diseases can include neoplasms such solid tumors, and cancers derived from T helper cells, including but not limited to peripheral T cell lymphoma and related malignant conditions. The diseases can also include autoimmune diseases such as vitiligo, type I diabetes mellitus, Rheumatoid Arthritis, Crohn's disease, inflammatory bowel disease, Ulcerative colitis. The diseases can also include neurodegenerative disorders such Parkinson's disease and Multiple Sclerosis; and cardiovascular diseases, such as Ischemic Heart Failure; and Human Immunodeficiency Virus (HIV) and Graft vs Host Disease (GvHD). In some embodiments, the antigen binding construct is linked to a therapeutic agent, such as a toxin, that can kill the cell to which the antigen binding construct is targeted and binds to. In some embodiments, rather than a therapy, the antigen binding construct can be used to diagnose or monitor a subject suspected of having one or more of these disorders (for example, by any of the methods provided herein).

Additional Embodiments

Some embodiments include detection of human CD4 which is a specific biomarker found on the surface of a subset of T-cells for diagnostic imaging of the immune system. Imaging of the target molecule can allow for the in vivo detection of T-cell localization. Changes in T-cell localization can reflect the progression of an immune response and can occur over time as a result of various therapeutic treatments or disease states such as infections. For example, imaging T-cell localization can be useful in immunotherapy. Adoptive immunotherapy is a form of therapy where a patient's own T-cells are manipulated in vitro and re-introduced into the patient. For this form of treatment, imaging of T-cells can be useful for monitoring and/or determining the status of the treatment. Thus, in some embodiments, monitoring the localization of the target molecule can be used in analyzing a mechanism of action, efficacy, and/or safety in the development of drugs and/or can aid in the clinical management of disease.

In some embodiments, the CDRs of an antigen binding construct that binds specifically to a target have been adjusted to minibody and cys-diabody arrangements.

In some embodiments, the anti-CD4 antigen binding constructs can be imaging agents that specifically target human CD4+ T-cells. In some embodiments, the anti-CD4 fragments can directly bind and detect the localization of the specific subclass of T-cells that express CD4. In some embodiments, engineered fragments able to cross link CD4 can potentiate signaling through the T cell receptor and enhance the ability of a subject to clear viral pathogens and respond to tumor antigens and vaccines.

In some embodiments, the minibody and cys-diabody antibody formats have desired pharmacokinetic characteristics for diagnostic imaging while maintaining the high binding affinity and specificity of the parental antibody. Compared to imaging with the full-length parental antibody, these fragments clear much faster; yet they are able to target the antigen for rapid high-contrast imaging. The same favorable pharmacokinetic properties are advantageous for targeting immune responses allowing for more controlled T cell stimulation and preventing undesirable effects of overstimulation (for example, cytokine storms). In preclinical models, the shorter blood half-lives for the minibody and the cys-diabody allow for optimal imaging at approximately 16-20 or 16-24 hours post injection for the minibody and 2-6 hours post-injection for the cys-diabody. Same day imaging can provide a significant advantage in the clinic with respect to patient care management.

In some embodiments, these antigen binding constructs can be diagnostic imaging agents (following labeling with an appropriate radioisotope such as Iodine-124, Cu-64 or Zr-89 (for PET imaging) or fluorophore (for fluorescent imaging)). As clinical imaging agents, these CD4 antigen binding constructs can help to monitor treatment and be used as a patient selection tool.

In some embodiments, the antigen binding constructs can be used for applications where highly specific and high-affinity binding to CD4 is required. Outside of diagnostic imaging, these fragments could serve different purposes depending on the attachment of different functional groups.

With the attachment of the appropriate infrared or fluorescent dye, these constructs can be used as the targeting agent for image-guided intraoperative surgery and endoscopic detection.

In some embodiments, in addition to the modifications to the functional groups attached to the fragments, through the use of bispecific fragments (where the fragment is able to bind 2 different antigens) it is possible to bring together CD4+ cells to a second antigen. Bispecific full-length antibodies have been used in cancer immunotherapy to bring cytotoxic cells of the immune system to tumor cells. Thus, such embodiments are also contemplated for the appropriate antigen binding constructs.

In some embodiments, CD4-specific antigen binding proteins can be bound, via chelation or direct conjugation, to radiolabels. In some embodiments, radiolabeled CD4-specific binding proteins can be utilized to classify or select a human subject for clinical trial, recommend or determine eligibility of a human subject for a therapeutic treatment, predict response to therapy of a human subject, and/or analyze or detect a change in the migration and/or distribution pattern of a CD4-bearing cell population in a human subject.

Additional, non-limiting numbered arrangements of the various elements and embodiments provided herein are as follows (which can be combined in a variety of was):

1. An antigen binding construct that comprises:
   a HCDR1 of the HCDR1 in SEQ ID NO: 2;
   a HCDR2 of the HCDR2 in SEQ ID NO: 2;
   a HCDR3 of the HCDR3 in SEQ ID NO: 2;

a LCDR1 of the LCDR1 in SEQ ID NO: 4;
a LCDR2 of the LCDR2 in SEQ ID NO: 4;
a LCDR3 of the LCDR3 in SEQ ID NO: 4; and
at least one VH framework residue selected from the group consisting of:
a Glutamine at position 1 of the sequence in SEQ ID NO: 2;
a Valine at position 5 of the sequence in SEQ ID NO: 2;
an Alanine at position 9 of the sequence in SEQ ID NO: 2;
a Valine at position 11 of the sequence in SEQ ID NO: 2;
a Lysine at position 13 of the sequence in SEQ ID NO: 2;
an Arginine at position 44 of the sequence in SEQ ID NO: 2;
a Glutamic acid at position 46 of the sequence in SEQ ID NO: 2;
a Glutamine at position 65 of the sequence in SEQ ID NO: 2;
a Glycine at position 66 of the sequence in SEQ ID NO: 2;
an Arginine at position 67 of the sequence in SEQ ID NO: 2;
a Valine at position 68 of the sequence in SEQ ID NO: 2;
a Threonine at position 69 of the sequence of SEQ ID NO: 2;
an Arginine at position 87 of the sequence in SEQ ID NO: 2;
a Serine at position 88 of the sequence in SEQ ID NO: 2.

2. An antigen binding construct that comprises:
a HCDR1 of the HCDR1 in SEQ ID NO: 2;
a HCDR2 of the HCDR2 in SEQ ID NO: 2;
a HCDR3 of the HCDR3 in SEQ ID NO: 2;
a LCDR1 of the LCDR1 in SEQ ID NO: 4;
a LCDR2 of the LCDR2 in SEQ ID NO: 4;
a LCDR3 of the LCDR3 in SEQ ID NO: 4; and
at least one VL framework residue selected from the group consisting of:
a Glutamic acid at position 1 of the sequence in SEQ ID NO: 4;
a Leucine at position 13 of the sequence in SEQ ID NO: 4;
an Arginine at position 18 of the sequence in SEQ ID NO: 4;
a Threonine at position 20 of the sequence in SEQ ID NO: 4;
a Leucine at position 21 of the sequence in SEQ ID NO: 4;
a Serine at position 22 of the sequence in SEQ ID NO: 4;
a Glutamine at position 41 of the sequence in SEQ ID NO: 4;
an Alanine at position 42 of the sequence in SEQ ID NO: 4;
an Isoleucine at position 57 of the sequence in SEQ ID NO: 4;
an Aspartic acid at position 59 of the sequence in SEQ ID NO: 4;
a Phenylalanine at position 70 of the sequence in SEQ ID NO: 4;
a Threonine at position 71 of the sequence in SEQ ID NO: 4;
a Leucine at position 77 of the sequence in SEQ ID NO: 4;
a Proline at position 79 of the sequence in SEQ ID NO: 4;
a Valine at position 84 of the sequence in SEQ ID NO: 4;
a Glycine at position 99 of the sequence in SEQ ID NO: 4.

3. The antigen binding construct of numbered arrangement 2, further comprising at least one VH framework residue selected from the group consisting of:
a Glutamine at position 1 of the sequence in SEQ ID NO: 2;
a Valine at position 5 of the sequence in SEQ ID NO: 2;
an Alanine at position 9 of the sequence in SEQ ID NO: 2;
a Valine at position 11 of the sequence in SEQ ID NO: 2;
a Lysine at position 13 of the sequence in SEQ ID NO: 2;
an Arginine at position 44 of the sequence in SEQ ID NO: 2;
a Glutamic acid at position 46 of the sequence in SEQ ID NO: 2;
a Glutamine at position 65 of the sequence in SEQ ID NO: 2;
a Glycine at position 66 of the sequence in SEQ ID NO: 2;
an Arginine at position 67 of the sequence in SEQ ID NO: 2;
a Valine at position 68 of the sequence in SEQ ID NO: 2;
a Threonine at position 69 of the sequence of SEQ ID NO: 2;
an Arginine at position 87 of the sequence in SEQ ID NO: 2;
a Serine at position 88 of the sequence in SEQ ID NO: 2.

4. The antigen binding construct of any of numbered arrangements 1-3, wherein the antigen binding construct binds specifically to CD4.

5. The antigen binding construct of numbered arrangement 4, wherein the antigen binding construct depletes CD4 T-cells.

6. The antigen binding construct of any of numbered arrangements 1-3, further comprising a detectable marker.

7. The antigen binding construct of any of numbered arrangements 1-3, further comprising a variable heavy domain (VH), wherein the VH comprises the amino acid sequence in SEQ ID NO: 2.

8. The antigen binding construct of any of numbered arrangements 1-3, further comprising a variable light domain (VL), wherein the VL comprises the amino acid sequence in SEQ ID NO: 4.

9. The antigen binding construct of any of numbered arrangements 1-3, further comprising:
a variable heavy domain (VH) of SEQ ID NO: 2; and
a variable light domain (VL), of SEQ ID NO: 4.

10. The antigen binding construct of any of numbered arrangements 1-3, wherein the antigen binding construct is a full-length antibody.

11. The antigen binding construct of any of numbered arrangements 1-3, wherein the antigen binding construct is a minibody.

12. The antigen binding construct of numbered arrangement 11, further comprising the amino acid sequence in SEQ ID NO: 5, 6, 7, or 8.

13. A nucleic acid sequence encoding the minibody of numbered arrangement 11, wherein the nucleic acid sequence comprises the nucleic acid sequence in SEQ ID NO: 9 or 10.

14. The antigen binding construct of any of numbered arrangements 1-3, wherein the antigen binding construct is a humanized cys-diabody.

15. The humanized cys-diabody of numbered arrangement 14 comprising the amino acid sequence in SEQ ID NO: 11, 12, 13, 14, 15, 16, 17, or 18.

16. The antigen binding construct of numbered arrangement 1, wherein the antigen binding construct comprises a polypeptide that comprises a single-chain variable fragment (scFv) comprising a variable heavy domain (VH) linked to a variable light domain (VL).

17. The humanized cys-diabody of numbered arrangement 14, wherein from N terminus to C terminus, is VH, VL.

18. The humanized cys-diabody of numbered arrangement 15, wherein from N terminus to C terminus, is VL, VH.

19. The antigen binding construct of any of numbered arrangements 1-3, further comprising a hinge region comprising the amino acid sequence in SEQ ID NO: 34, 35, 36, or 37.

20. The antigen binding construct of any of numbered arrangements 1-3, further comprising at least of:
   a Glutamine at position 1 of the sequence in SEQ ID NO: 2;
   a Valine at position 5 of the sequence in SEQ ID NO: 2;
   an Alanine at position 9 of the sequence in SEQ ID NO: 2;
   a Valine at position 11 of the sequence in SEQ ID NO: 2;
   a Lysine at position 13 of the sequence in SEQ ID NO: 2;
   an Arginine at position 44 of the sequence in SEQ ID NO: 2;
   a Glutamic acid at position 46 of the sequence in SEQ ID NO: 2;
   a Glutamine at position 65 of the sequence in SEQ ID NO: 2;
   a Glycine at position 66 of the sequence in SEQ ID NO: 2;
   an Arginine at position 67 of the sequence in SEQ ID NO: 2;
   a Valine at position 68 of the sequence in SEQ ID NO: 2;
   a Threonine at position 69 of the sequence of SEQ ID NO: 2;
   an Arginine at position 87 of the sequence in SEQ ID NO: 2;
   a Serine at position 88 of the sequence in SEQ ID NO: 2;
   a Glutamic acid at position 1 of the sequence in SEQ ID NO: 4;
   a Leucine at position 13 of the sequence in SEQ ID NO: 4;
   an Arginine at position 18 of the sequence in SEQ ID NO: 4;
   a Threonine at position 20 of the sequence in SEQ ID NO: 4;
   a Leucine at position 21 of the sequence in SEQ ID NO: 4;
   a Serine at position 22 of the sequence in SEQ ID NO: 4;
   a Glutamine at position 41 of the sequence in SEQ ID NO: 4;
   an Alanine at position 42 of the sequence in SEQ ID NO: 4;
   an Isoleucine at position 57 of the sequence in SEQ ID NO: 4;
   an Aspartic acid at position 59 of the sequence in SEQ ID NO: 4;
   a Phenylalanine at position 70 of the sequence in SEQ ID NO: 4;
   a Threonine at position 71 of the sequence in SEQ ID NO: 4;
   a Leucine at position 77 of the sequence in SEQ ID NO: 4;
   a Proline at position 79 of the sequence in SEQ ID NO: 4;
   a Valine at position 84 of the sequence in SEQ ID NO: 4;
   a Glycine at position 99 of the sequence in SEQ ID NO: 4.

21. The antigen binding construct of any of numbered arrangements 1-3, further comprising at least of:
   a Glutamine at position 1 of the sequence in SEQ ID NO: 2;
   a Valine at position 5 of the sequence in SEQ ID NO: 2;
   an Alanine at position 9 of the sequence in SEQ ID NO: 2;
   a Valine at position 11 of the sequence in SEQ ID NO: 2;
   a Lysine at position 13 of the sequence in SEQ ID NO: 2;
   an Arginine at position 44 of the sequence in SEQ ID NO: 2;
   a Glutamic acid at position 46 of the sequence in SEQ ID NO: 2;
   a Glutamine at position 65 of the sequence in SEQ ID NO: 2;
   a Glycine at position 66 of the sequence in SEQ ID NO: 2;
   an Arginine at position 67 of the sequence in SEQ ID NO: 2;
   a Valine at position 68 of the sequence in SEQ ID NO: 2;
   a Threonine at position 69 of the sequence of SEQ ID NO: 2;
   an Arginine at position 87 of the sequence in SEQ ID NO: 2;
   a Serine at position 88 of the sequence in SEQ ID NO: 2;
   a Glutamic acid at position 1 of the sequence in SEQ ID NO: 4;
   a Leucine at position 13 of the sequence in SEQ ID NO: 4;
   an Arginine at position 18 of the sequence in SEQ ID NO: 4;
   a Threonine at position 20 of the sequence in SEQ ID NO: 4;
   a Leucine at position 21 of the sequence in SEQ ID NO: 4;
   a Serine at position 22 of the sequence in SEQ ID NO: 4;
   a Glutamine at position 41 of the sequence in SEQ ID NO: 4;
   an Alanine at position 42 of the sequence in SEQ ID NO: 4;
   an Isoleucine at position 57 of the sequence in SEQ ID NO: 4;
   an Aspartic acid at position 59 of the sequence in SEQ ID NO: 4;
   a Phenylalanine at position 70 of the sequence in SEQ ID NO: 4;
   a Threonine at position 71 of the sequence in SEQ ID NO: 4;
   a Leucine at position 77 of the sequence in SEQ ID NO: 4;
   a Proline at position 79 of the sequence in SEQ ID NO: 4;
   a Valine at position 84 of the sequence in SEQ ID NO: 4;
   a Glycine at position 99 of the sequence in SEQ ID NO: 4.

22. The antigen binding construct of any of numbered arrangements 1-3, further comprising all of:
   a Glutamine at position 1 of the sequence in SEQ ID NO: 2;
   a Valine at position 5 of the sequence in SEQ ID NO: 2;
   an Alanine at position 9 of the sequence in SEQ ID NO: 2;
   a Valine at position 11 of the sequence in SEQ ID NO: 2;
   a Lysine at position 13 of the sequence in SEQ ID NO: 2;
   an Arginine at position 44 of the sequence in SEQ ID NO: 2;

a Glutamic acid at position 46 of the sequence in SEQ ID NO: 2;
a Glutamine at position 65 of the sequence in SEQ ID NO: 2;
a Glycine at position 66 of the sequence in SEQ ID NO: 2;
an Arginine at position 67 of the sequence in SEQ ID NO: 2;
a Valine at position 68 of the sequence in SEQ ID NO: 2;
a Threonine at position 69 of the sequence of SEQ ID NO: 2;
an Arginine at position 87 of the sequence in SEQ ID NO: 2;
a Serine at position 88 of the sequence in SEQ ID NO: 2;
a Glutamic acid at position 1 of the sequence in SEQ ID NO: 4;
a Leucine at position 13 of the sequence in SEQ ID NO: 4;
an Arginine at position 18 of the sequence in SEQ ID NO: 4;
a Threonine at position 20 of the sequence in SEQ ID NO: 4;
a Leucine at position 21 of the sequence in SEQ ID NO: 4;
a Serine at position 22 of the sequence in SEQ ID NO: 4;
a Glutamine at position 41 of the sequence in SEQ ID NO: 4;
an Alanine at position 42 of the sequence in SEQ ID NO: 4;
an Isoleucine at position 57 of the sequence in SEQ ID NO: 4;
an Aspartic acid at position 59 of the sequence in SEQ ID NO: 4;
a Phenylalanine at position 70 of the sequence in SEQ ID NO: 4;
a Threonine at position 71 of the sequence in SEQ ID NO: 4;
a Leucine at position 77 of the sequence in SEQ ID NO: 4;
a Proline at position 79 of the sequence in SEQ ID NO: 4;
a Valine at position 84 of the sequence in SEQ ID NO: 4;
a Glycine at position 99 of the sequence in SEQ ID NO: 4.

23. A minibody or cys-diabody that comprises:
a HCDR1 of the HCDR1 in SEQ ID NO: 2;
a HCDR2 of the HCDR2 in SEQ ID NO: 2;
a HCDR3 of the HCDR3 in SEQ ID NO: 2;
a LCDR1 of the LCDR1 in SEQ ID NO: 4;
a LCDR2 of the LCDR2 in SEQ ID NO: 4;
a LCDR3 of the LCDR3 in SEQ ID NO: 4; and at least one of:
a Glutamine at position 1 of the sequence in SEQ ID NO: 2;
a Valine at position 2 of the sequence in SEQ ID NO: 2;
a Leucine at position 4 of the sequence in SEQ ID NO: 2;
an Alanine at position 24 of the sequence in SEQ ID NO: 2;
a Serine at position 25 of the sequence in SEQ ID NO: 2;
a Methionine at position 34 of the sequence in SEQ ID NO: 2;
a Histidine at position 35 of the sequence in SEQ ID NO: 2;
a Glutamic acid position 46 of the sequence in SEQ ID NO: 2;
a Tryptophan at position 47 of the sequence in SEQ ID NO: 2;
an Isoleucine at position 48 of the sequence in SEQ ID NO: 2;
a Glycine at position 49 of the sequence in SEQ ID NO: 2;
an Alanine at position 50 of the sequence in SEQ ID NO: 2;
a Leucine at position 51 of the sequence in SEQ ID NO: 2;
an Asparagine at position 61 of the sequence in SEQ ID NO: 2;
a Phenylalanine at position 64 of the sequence in SEQ ID NO: 2;
an Isoleucine at position 70 of the sequence in SEQ ID NO: 2;
an Arginine at position 72 of the sequence in SEQ ID NO: 2;
an Alanine at position 79 of the sequence in SEQ ID NO: 2;
a Threonine at position 97 of the sequence in SEQ ID NO: 2;
an Arginine at position 98 of the sequence in SEQ ID NO: 2;
a Glutamic acid at position 1 of the sequence in SEQ ID NO: 4;
an Isoleucine at position 2 of the sequence in SEQ ID NO: 4;
a Leucine at position 4 of the sequence in SEQ ID NO: 4;
a Glutamine at position 6 of the sequence in SEQ ID NO: 4;
a Tryptophan at position 34 of the sequence in SEQ ID NO: 4;
a Tyrosine at position 35 of the sequence in SEQ ID NO: 4;
a Leucine at position 45 of the sequence in SEQ ID NO: 4;
a Leucine at position 46 of the sequence in SEQ ID NO: 4;
an Isoleucine at position 47 of the sequence in SEQ ID NO: 4;
a Glycine at position 67 of the sequence in SEQ ID NO: 4;
a Phenylalanine at position 70 of the sequence in SEQ ID NO: 4;
a Phenylalanine at position 97 of the sequence in SEQ ID NO: 4.

24. An antigen binding construct that comprises:
a HCDR1 of the HCDR1 in SEQ ID NO: 2;
a HCDR2 of the HCDR2 in SEQ ID NO: 2;
a HCDR3 of the HCDR3 in SEQ ID NO: 2;
a LCDR1 of the LCDR1 in SEQ ID NO: 4;
a LCDR2 of the LCDR2 in SEQ ID NO: 4;
a LCDR3 of the LCDR3 in SEQ ID NO: 4; and at least one of:
a Glutamine at position 1 of the sequence in SEQ ID NO: 2;
a Valine at position 20 of the sequence in SEQ ID NO: 2;
an Arginine at position 38 of the sequence in SEQ ID NO: 2;
an Alanine at position 40 of the sequence in SEQ ID NO: 2;
an Arginine at position 44 of the sequence in SEQ ID NO: 2;
a Tyrosine at position 60 of the sequence in SEQ ID NO: 2;
a Valine at position 68 of the sequence in SEQ ID NO: 2;
an Isoleucine at position 70 of the sequence in SEQ ID NO: 2;

an Arginine at position 72 of the sequence in SEQ ID NO: 2;
a Threonine at position 74 of the sequence in SEQ ID NO: 2;
a Glutamic acid at position 1 of the sequence in SEQ ID NO: 4;
a Leucine at position 11 of the sequence in SEQ ID NO: 4;
a Leucine at position 13 of the sequence in SEQ ID NO: 4;
an Alanine at position 19 of the sequence in SEQ ID NO: 4;
a Leucine at position 21 of the sequence in SEQ ID NO: 4;
an Isoleucine at position 57 of the sequence in SEQ ID NO: 4;
a Phenylalanine at position 70 of the sequence in SEQ ID NO: 4;
a Leucine at position 77 of the sequence in SEQ ID NO: 4;
a Proline at position 79 of the sequence in SEQ ID NO: 4;
a Valine at position 84 of the sequence in SEQ ID NO: 4;
a Glycine at position 99 of the sequence in SEQ ID NO: 4.

25. An antigen binding construct that comprises:
a HCDR1 of the HCDR1 in SEQ ID NO: 2;
a HCDR2 of the HCDR2 in SEQ ID NO: 2;
a HCDR3 of the HCDR3 in SEQ ID NO: 2;
a LCDR1 of the LCDR1 in SEQ ID NO: 4;
a LCDR2 of the LCDR2 in SEQ ID NO: 4;
a LCDR3 of the LCDR3 in SEQ ID NO: 4; and at least one of:
a) a VH comprising at least one of: E1Q, Q5V, T9A, V10E, L11V, A12K, R13K, Q19K, M20V, K38R, R40A, Q46E, T59, N61, K65Q, D66G, K67R, A68V, K69T, L70I, A72R, V73D, T87R, N88S, S91T, T115L, or L116V;
b) a VL comprising at least one of: Q1E, I10T, M11L, A13L, K18R, V19A, A20T, M21L, T22S, S41Q, S42A, V57I, V59D, I62S, S69D, Y70F, S71T, M77L, A79P, A82, T84V, A99G, or L106I;
c) the VH of a) and the VL of b);
d) any one of a), b), and c), wherein the VH is at least 80% identical to SEQ ID NO: 2;
e) any one of a), b), and c), wherein the VL is at least 80% identical to SEQ ID NO: 4;
f) any one of a), b), and c), wherein the VH is at least 80% identical to SEQ ID NO: 2; and any one of a), b), and c), wherein the VL is at least 80% identical to SEQ ID NO: 4;
g) a VH with T59, N61, or both, wherein the VH is a humanized VH;
h) a VL with A82, wherein the VL is a humanized VL;
i) a VH according to g) and a VL according to h);
j) a VH with Q46E;
k) a VH with Q46E, wherein
  i) the VH is at least 80% identical to SEQ ID NO: 2
  ii) the VL is at least 80% identical to SEQ ID NO: 4
  iiii) the VH is at least 80% identical to SEQ ID NO: 2 and the VL is at least 80% identical to SEQ ID NO: 4;
l) a VH with at least one of T115L, L116V;
m) a VL with at least one of S41Q, A99G, or L106I;
n) a VH with at least one of T115L, L116V and a VL with at least one of S41Q, A99G, or L106I; or
o) l), m), or n), wherein
  i) the VH is at least 80% identical to SEQ ID NO: 2
  ii) the VL is at least 80% identical to SEQ ID NO: 4
  iiii) the VH is at least 80% identical to SEQ ID NO: 2 and the VL is at least 80% identical to SEQ ID NO: 4.

26. The antigen binding construct of any one of numbered arrangements 1-12 or 19-25, wherein the antigen binding construct is a minibody.

27. The antigen binding construct of any one of numbered arrangements 1-12 or 19-26, wherein the VH is at least 90% identical to SEQ ID NO: 2, the VL is at least 90% identical to SEQ ID NO: 4, or the VH and VL are at least 90% identical to SEQ ID Nos: 2 and 4 respectively.

28. The antigen binding construct of any one of numbered arrangements 1-12 or 19-27, wherein the VH is at least 95% identical to SEQ ID NO: 2, the VL is at least 95% identical to SEQ ID NO: 4, or the VH and VL are at least 95% identical to SEQ ID Nos: 2 and 4 respectively.

29. The antigen binding construct of any one of numbered arrangements 1-12 or 19-28, wherein the VH is at least 99% identical to SEQ ID NO: 2, the VL is at least 99% identical to SEQ ID NO: 4, or the VH and VL are at least 99% identical to SEQ ID Nos: 2 and 4 respectively.

30. The antigen binding construct of any one of numbered arrangements 1-12 or 19-29, wherein the VH is identical to SEQ ID NO: 2, the VL is identical to SEQ ID NO: 4, or the VH and VL are identical to SEQ ID Nos: 2 and 4 respectively.

31. The antigen binding construct of any one of numbered arrangements 1-12 or 19-30, wherein the antigen binding construct binds to CD4.

32. The antigen binding construct of numbered arrangement 31, wherein the CD4 is human CD4.

33. The antigen binding construct of any one of numbered arrangements 1-12 or 19-32, further comprising a hinge region comprising the amino acid sequence in SEQ ID NO: 34, 35, 36, or 37.

34. The antigen binding construct of any one of numbered arrangements 1-12 or 19-33, wherein for a)-f), there are at least two of: E1Q, Q5V, T9A, V10E, L11V, A12K, R13K, Q19K, M20V, K38R, R40A, Q46E, T59, N61, K65Q, D66G, K67R, A68V, K69T, L70I, A72R, V73D, T87R, N88S, S91T, T115L, or L116V for VH and/or at least two of Q1E, I10T, M11L, A13L, K18R, V19A, A20T, M21L, T22S, S41Q, S42A, V57I, V59D, I62S, S69D, Y70F, S71T, M77L, A79P, A82, T84V, A99G, or L106I for VL.

35. The antigen binding construct of any one of numbered arrangements 1-12 or 19-34, wherein the antigen binding construct is a minibody, and wherein the minibody is covalently linked to a detectable marker.

36. The antigen binding construct of numbered arrangement 35, wherein the detectable marker is at least one of $^{18}$F or $^{89}$Zr.

37. The antigen binding construct of any one of numbered arrangements 1-12 or 19-36, wherein the antigen binding construct comprises a VH with T59, N61, or both, wherein the VH is a humanized VH.

38. The antigen binding construct of any one of numbered arrangements 1-12 or 19-37, wherein the antigen binding construct comprises a VL with A82, wherein the VL is a humanized VL.

39. The antigen binding construct of any one of numbered arrangements 1-12 or 19-38, wherein the antigen binding construct comprises a VH with T59, N61, or both, wherein the VH is a humanized VH; and wherein the antigen binding construct comprises a VL with A82, wherein the VL is a humanized VL.

40. The antigen binding construct of any one of numbered arrangements 1-12 or 19-39, wherein the antigen binding construct comprises SEQ ID NO: 5.

41. A humanized minibody that binds to human CD4, wherein the humanized minibody comprises:
   a HCDR1 of the HCDR1 in SEQ ID NO: 2;
   a HCDR2 of the HCDR2 in SEQ ID NO: 2;
   a HCDR3 of the HCDR3 in SEQ ID NO: 2;
   a LCDR1 of the LCDR1 in SEQ ID NO: 4;
   a LCDR2 of the LCDR2 in SEQ ID NO: 4;
   a LCDR3 of the LCDR3 in SEQ ID NO: 4; and at least one of:
      a) a VH with T59, N61, or both, wherein the VH is a humanized VH, wherein the VH is at least 80% identical to SEQ ID NO: 2, and a VL that is at least 80% identical to SEQ ID NO: 4;
      b) a VH and VL that is in the VL-VH orientation (amino to carboxyl);
      c) a VL with A99G;
      d) a VH with T59, N61, or both,
      e) a VL with A99G and ii) a VH with T59, N61, or both,
      f) a VH with T59, N61, or both, wherein the VH is a humanized VH, wherein the VH is at least 80% identical to SEQ ID NO: 2, and a VL that is at least 80% identical to SEQ ID NO: 4 and wherein the VL comprises A99G; or
      g) a VH comprising T59, N61, or both, wherein the VH is a humanized VH as numbered accord to the numbering of SEQ ID NO: 2, and A VL comprising A99G, as numbered accord to the numbering of SEQ ID NO: 4.

42. The humanized minibody of numbered arrangement 41, wherein the humanized minibody comprises a VH with T59, N61, or both, wherein the VH is a humanized VH, wherein the VH is at least 80% identical to SEQ ID NO: 2.

43. The humanized minibody of numbered arrangement 41 or numbered arrangement 42, wherein the humanized minibody comprises and a VL that is at least 80% identical to SEQ ID NO: 4 and wherein the VL comprises A99G.

44. The humanized minibody of any one of numbered arrangements 41-43, wherein the humanized minibody comprises a VH with T59, N61, or both, wherein the VH is a humanized VH, wherein the VH is at least 80% identical to SEQ ID NO: 2; and wherein the humanized minibody comprises and a VL that is at least 80% identical to SEQ ID NO: 4 and wherein the VL comprises A99G.

45. The humanized minibody of any one of numbered arrangements 41-44, wherein the humanized minibody comprises a VH comprising T59, N61, or both, wherein the VH is a humanized VH as numbered accord to the numbering of SEQ ID NO: 2.

46. The humanized minibody of any one of numbered arrangements 41-45, wherein the humanized minibody comprises a VL comprising A99G, as numbered accord to the numbering of SEQ ID NO: 4.

47. The humanized minibody of any one of numbered arrangements 41-46, wherein the humanized minibody comprises a VH comprising T59, N61, or both, wherein the VH is a humanized VH as numbered accord to the numbering of SEQ ID NO: 2; and wherein the humanized minibody comprises a VL comprising A99G, as numbered accord to the numbering of SEQ ID NO: 4.

48. The humanized minibody of any one of numbered arrangements 41-47, wherein the humanized minibody comprises SEQ ID NO: 5.

49. A method of treating a subject, the method comprising:
   providing a subject suffering from a CD4 related disorder; and
   administering an effective amount of the humanized minibody of any one of numbered arrangements 41-48 or the antigen binding construct of any one of numbered arrangements 1-12, 14-22, 24-40, or the minibody or the cys-diabody of numbered arrangement 23 to the subject so as to reduce at least one symptom from the CD4 related disorder.

50. The method of numbered arrangement 49, wherein the humanized minibody, antigen binding construct, minibody, or cys-diabody is linked to a therapeutic agent.

51. Use of the humanized minibody of any one of numbered arrangements 41-48 or the antigen binding construct of any one of numbered arrangements 1-12, 14-22, 24-40, or the minibody or the cys-diabody of numbered arrangement 23 for the preparation of a medicament for the treatment of a CD4 related disorder.

52. The humanized minibody of any one of numbered arrangements 41-48, or the antigen binding construct of any one of numbered arrangements 1-12, 14-22, 24-40, or the minibody or the cys-diabody of numbered arrangement 23 for use as a medicament.

53. The humanized minibody of numbered arrangements 41-48, or the antigen binding construct of any one of numbered arrangements 1-12, 14-22, 24-40, or the minibody or the cys-diabody of numbered arrangement 23 for use in at least one of: detection, diagnosis, surgery, staging, treatment, monitoring of treatment, monitoring of disease progression, and monitoring therapy.

54. The humanized minibody of numbered arrangements 41-48, or the antigen binding construct of any one of numbered arrangements 1-12, 14-22, 24-40, or the minibody or the cys-diabody of numbered arrangement 23 for use in at least one of: detection, diagnosis, surgery, staging, treatment, monitoring of treatment, monitoring of disease progression, and monitoring therapy of a CD4 related disorder.

EXAMPLE 1: CYTOMETRY

The antibody was tested in cytometry experiments (binding to primary T-cells). FIG. 1 illustrates the flow cytometry binding results of unconjugated anti-human-CD4 minibodies to HPB-ALL cells (Species: human (Homo sapiens); Cell type: T cell leukemia; DSMZ no.: ACC 483). (A) illustrates binding of different chimera and humanized constructs tested by flow cytometry. (B) illustrates positive control: commercial anti-human-CD4 antibody. (C) illustrates the EC50 values for the chimera and humanized minibodies as compared to a commercial positive control.

Figure 2:
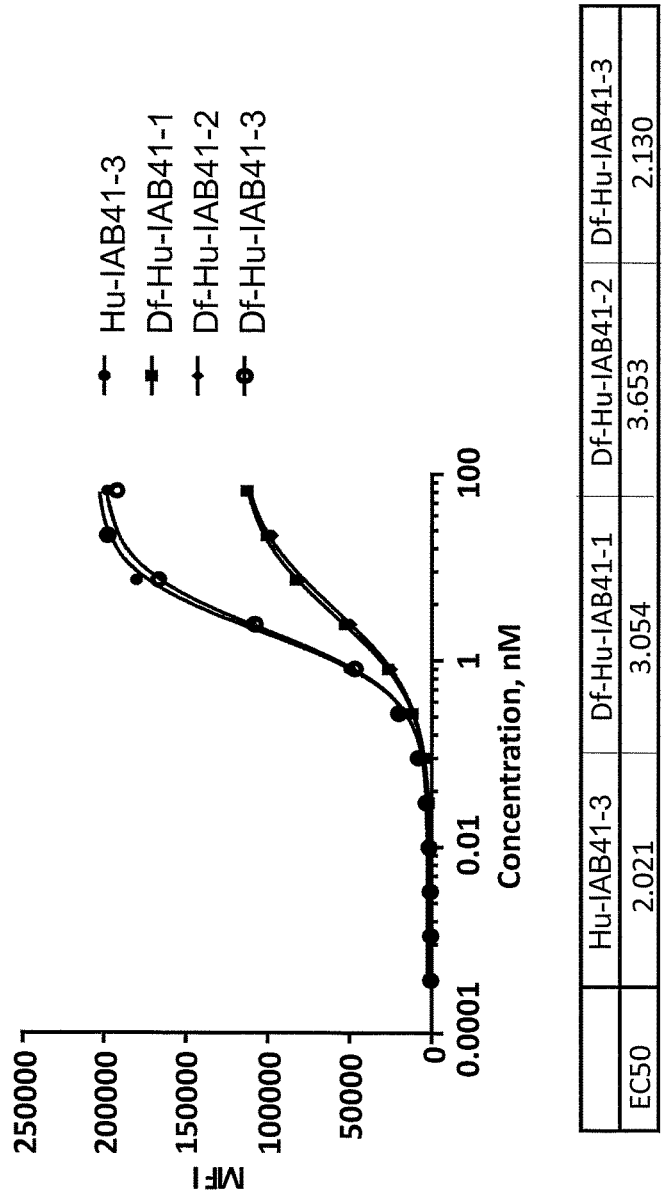
FIG. 2 depicts the results of a flow cytometry binding analysis of deferoxamine conjugated humanized anti-human-CD4 minibodies to HPB-ALL cells, as compared to an unconjugated minibody. Df-Hu-IAB41-1 includes the sequence from SEQ ID NO:5, along with the Df chelator.

FIG. 2 illustrates the flow cytometry binding of deferoxamine conjugated humanized anti-human-CD4 minibodies to HPB-ALL cells, as compared to an unconjugated minibody. Conjugation with deferoxamine did not affect the binding to HPC-ALL. The constructs tested for the results are as follows: IAB41-1 in FIG. 4, SEQ ID 5; IAB41-2 in FIG. 5, SEQ ID 6; and IAB41-3 in FIG. 7, SEQ ID 8. Construct 41-1 is FIG. 4.

EXAMPLE 2: IN VIVO DETECTION OF CD4

A humanized CD4 cys-diabody is conjugated with a relevant chelator via C-terminal cysteines on the cys-diabody and subsequently radiolabeled with an isotope of In111, (or in the alternative, Zr89 or Cu64). Alternatively, the cys-diabody is radiolabeled after attaching relevant chelators to Lysine residues or directly radiolabeled with Iodine. Alternatively, the cys-diabody is radiolabeled with F18 via reductive amination with [18F]-fluorobenzaldehyde, or via reaction with [18F]-N-succinimidyl-fluorobenzoate.

The cys-diabody is infused or injected intravenously into a human subject. The cys-diabody circulates and diffuses through the subject post-infusion. Within the same day as the incubation, the localization of the cys-diabody is detected via a PET scan or external scintillation system.

Localization of cys-diabody is used to determine localization of CD4-bearing cells in the subject. Presence or absence of accumulations of CD4-bearing cells in organs or neoplasia can be used, among other purposes, to classify or select a human subject for clinical trial, recommend or determine eligibility of a human subject for a therapeutic treatment, predict response to therapy of a human subject, and/or analyze or detect a change in the migration and/or distribution pattern of a CD4-bearing cell population in a human subject in response to a therapeutic treatment.

EXAMPLE 3: IN VIVO DETECTION OF CD4

A CD4 minibody is conjugated with a relevant chelator via Lysine residues on the minibody and subsequently radiolabeled with an isotope of In111 (or in the alternative, Zr89 or Cu64), or directly labelling of lysine residues with Iodine containing compounds such as Bolten-Huntrer. Alternatively, the minibody can be radiolabeled by directly radiolabeling with Iodine via Tyrosine residues. Alternatively, the minibody is radiolabeled with F18 via reductive amination with [18F]-fluorobenzaldehyde, or via reaction with [18F]-N-succinimidyl-fluorobenzoate.

The minibody is infused intravenously into a human subject. The minibody circulates and diffuses through the subject post-infusion. On the same day as the incubation, the localization of the minibody is detected via a PET scan or external scintillation system.

Localization of minibody is used to determine localization of CD4-bearing cells in the subject. Presence or absence of accumulations of CD4-bearing cells in organs or neoplasia can be used, among other purposes, to classify or select a human subject for clinical trial, recommend or determine eligibility of a human subject for a therapeutic treatment, predict response to therapy of a human subject, and/or analyze or detect a change in the migration and/or distribution pattern of a CD4-bearing cell population in a human subject in response to a therapeutic treatment.

EXAMPLE 4

The IAB41 minibodies were produced by transient expression in mammalian cells. The DNA sequence was cloned in a plasmid suitable for mammalian expression and transfected in Expi293 cells according to the manufacturer provided protocol. The cell culture was incubated under agitation for 4 days at 37° C., in sterile polycarbonate conical flasks with vented cap. The cell viability and concentration were monitored during the culture. On the fourth day after transfection, the conditioned media containing the minibody was separated by centrifugation at 600 rpm, followed by sterile filtration through a sterile 0.22 µm filter bottle.

The minibody was purified from the conditioned media by affinity chromatography with a chromatographic resin comprising camelid-derived single domain antibody fragments conjugated to agarose beads. The conditioned media was passed through the affinity matrix while monitoring the absorbance at 280 nm. Following this loading step, the column was washed with phosphate buffer saline until the absorbance at 280 nm reached baseline value. The minibody was then eluted from the affinity resin with buffer at pH 3.5. The pH of the elution fraction was immediately corrected to pH 7.2 with concentrated Tris buffer, and the antibody concentration calculated by measuring the absorbance at 280 nm. The purity of the minibody was tested by analytical size exclusion chromatography and sodium dodecyl sulfate polyacrylamide gel electrophoresis. The minibody was further polished by preparative size exclusion chromatography on a Sephacryl 200 column using phosphate buffer saline as mobile phase. Fractions corresponding to the monomeric minibody were combined and the concentration confirmed by measuring the absorbance at 280 nm.

Conjugation of the minibody with deferoxamine (Df) was performed by incubation of the minibody with Df at ratio of 1:7 for 2 hours at 35° C., in solution buffered at pH 8.5. At the end of the conjugation reaction, the concentration and the chelator to minibody ratio were measured by UV spectroscopy, and the purity of the conjugated product was assessed by analytical size exclusion chromatography. Radiolabeling of the Df-conjugated minibody was performed by incubation of the conjugate with $^{89}$Zr-oxalate at neutral pH. The reaction mixture was challenged with Diethylenetriamine Penta-acetic Acid (DTPA), to capture free $^{89}$Zr. The radiolabeled minibody was purified by gel filtration chromatography. Radiochemical purity was measured by instant thin layer chromatography (iTLC).

Singular Terms

In this application, the use of the singular can include the plural unless specifically stated otherwise or unless, as will be understood by one of skill in the art in light of the present disclosure, the singular is the only functional embodiment. Thus, for example, "a" can mean more than one, and "one embodiment" can mean that the description applies to multiple embodiments.

Incorporation By Reference

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application; including but not limited to defined terms, term usage, described techniques, or the like, this application controls.

Equivalents

The foregoing description and Examples detail certain embodiments. It will be appreciated, however, that no matter how detailed the foregoing may appear in text, the invention may be practiced in many ways and the invention should be construed in accordance with the appended claims and any equivalents thereof.

What is claimed is:

1. An antigen binding construct that comprises:
   a HCDR1 having the amino acid sequence KASGYSFANYWMH (SEQ ID NO: 45);
   a HCDR2 having the amino acid sequence EWIGALYPGNVDTT (SEQ ID NO: 46);
   a HCDR3 having the amino acid sequence TRMGTTLEAPLDY (SEQ ID NO: 47);
   a LCDR1 having the amino acid sequence SARSSVSYLY (SEQ ID NO:48);
   a LCDR2 having the amino acid sequence YDTSNLAS (SEQ ID NO:49); and
   a LCDR3 having the amino acid sequence QQWSDYPLT (SEQ ID NO:50).

2. The antigen binding construct of claim 1, further comprising at least one VL framework residue selected from the group consisting of:
   a Glutamic acid at position 1 of the sequence in SEQ ID NO: 4;
   a Leucine at position 13 of the sequence in SEQ ID NO: 4;
   an Arginine at position 18 of the sequence in SEQ ID NO: 4;
   a Threonine at position 20 of the sequence in SEQ ID NO: 4;
   a Leucine at position 21 of the sequence in SEQ ID NO: 4;
   a Serine at position 22 of the sequence in SEQ ID NO: 4;
   a Glutamine at position 41 of the sequence in SEQ ID NO: 4;
   an Alanine at position 42 of the sequence in SEQ ID NO: 4;
   an Isoleucine at position 57 of the sequence in SEQ ID NO: 4;
   an Aspartic acid at position 59 of the sequence in SEQ ID NO: 4;
   a Phenylalanine at position 70 of the sequence in SEQ ID NO: 4;
   a Threonine at position 71 of the sequence in SEQ ID NO: 4;
   a Leucine at position 77 of the sequence in SEQ ID NO: 4;
   a Proline at position 79 of the sequence in SEQ ID NO: 4;

a Valine at position 84 of the sequence in SEQ ID NO: 4; and a Glycine at position 99 of the sequence in SEQ ID NO: 4.

3. The antigen binding construct of claim 1, further comprising at least one VH framework residue selected from the group consisting of:
a Glutamine at position 1 of the sequence in SEQ ID NO: 2;
a Valine at position 5 of the sequence in SEQ ID NO: 2;
an Alanine at position 9 of the sequence in SEQ ID NO: 2;
a Valine at position 11 of the sequence in SEQ ID NO: 2;
a Lysine at position 13 of the sequence in SEQ ID NO: 2;
an Arginine at position 44 of the sequence in SEQ ID NO: 2;
a Glutamine at position 65 of the sequence in SEQ ID NO: 2;
a Glycine at position 66 of the sequence in SEQ ID NO: 2;
an Arginine at position 67 of the sequence in SEQ ID NO: 2;
a Valine at position 68 of the sequence in SEQ ID NO: 2;
a Threonine at position 69 of the sequence of SEQ ID NO: 2;
an Arginine at position 87 of the sequence in SEQ ID NO: 2; and
a Serine at position 88 of the sequence in SEQ ID NO: 2.

4. The antigen binding construct of claim 1, further comprising a detectable marker.

5. The antigen binding construct of claim 1, further comprising a variable heavy domain (VH), wherein the VH comprises the amino acid sequence in SEQ ID NO: 2.

6. The antigen binding construct of claim 1, further comprising a variable light domain (VL), wherein the VL comprises the amino acid sequence in SEQ ID NO: 4.

7. The antigen binding construct of claim 1, wherein the antigen binding construct is a minibody.

8. The antigen binding construct of claim 7, further comprising the amino acid sequence in SEQ ID NO: 5, 6, 7, or 8.

9. A nucleic acid sequence encoding the antigen binding construct of claim 7, wherein the nucleic acid sequence comprises the nucleic acid sequence in SEQ ID NO: 9 or 10.

10. The antigen binding construct of claim 1, wherein the antigen binding construct is a humanized cys-diabody.

11. The antigen binding construct of claim 10 comprising the amino acid sequence in SEQ ID NO: 11, 12, 13, 14, 15, 16, 17, or 18.

12. The antigen binding construct of claim 1, wherein the antigen binding construct comprises a polypeptide that comprises a single-chain variable fragment (scFv) comprising a variable heavy domain (VH) linked to a variable light domain (VL).

13. The antigen binding construct of claim 1, further comprising a hinge region comprising the amino acid sequence in SEQ ID NO: 34, 35, 36, or 37.

14. An antigen binding construct that comprises:
a HCDR1 of the HCDR1 in SEQ ID NO: 2;
a HCDR2 of the HCDR2 in SEQ ID NO: 2;
a HCDR3 of the HCDR3 in SEQ ID NO: 2;
a LCDR1 of the LCDR1 in SEQ ID NO: 4;
a LCDR2 of the LCDR2 in SEQ ID NO: 4;
a LCDR3 of the LCDR3 in SEQ ID NO: 4; and
at least one of:
a) a VH comprising at least one of: E1Q, Q5V, T9A, V10E, L11V, A12K, R13K, Q19K, M20V, K38R, R40A, Q46E, T59, N61, K65Q, D66G, K67R, A68V, K69T, L70I, A72R, V73D, T87R, N88S, S91T, T115L, or L116V;
b) a VL comprising at least one of: Q1E, I10T, M11L, A13L, K18R, V19A, A20T, M21L, T22S, S41Q, S42A, V57I, V59D, I62S, S69D, Y70F, S71T, M77L, A79P, A82, T84V, A99G, or L106I;
c) the VH of a) and the VL of b);
d) any one of a), b), and c), wherein the VH is at least 80% identical to SEQ ID NO: 2;
e) any one of a), b), and c), wherein the VL is at least 80% identical to SEQ ID NO: 4;
f) any one of a), b), and c), wherein the VH is at least 80% identical to SEQ ID NO: 2; and any one of a), b), and c), wherein the VL is at least 80% identical to SEQ ID NO: 4;
g) a VH with T59, N61, or both, wherein the VH is a humanized VH;
h) a VL with A82, wherein the VL is a humanized VL;
i) a VH according to g) and a VL according to h);
j) a VH with Q46E;
k) a VH with Q46E, wherein
i) the VH is at least 80% identical to SEQ ID NO: 2;
ii) the VL is at least 80% identical to SEQ ID NO: 4; or
iii) the VH is at least 80% identical to SEQ ID NO: 2 and the VL is at least 80% identical to SEQ ID NO: 4;
l. A VH with at least one of T115L, L116V;
m) a VL with at least one of S41Q, A99G, or L106I;
n) a VH with at least one of T115L, L116V and a VL with at least one of S41Q, A99G, or L106I; or
o) l), m), or n), wherein
i) the VH is at least 80% identical to SEQ ID NO: 2;
ii) the VL is at least 80% identical to SEQ ID NO: 4; or
iii) the VH is at least 80% identical to SEQ ID NO: 2 and the VL is at least 80% identical to SEQ ID NO: 4.

15. The antigen binding construct of claim 1, comprising:
a variable heavy domain (VH), wherein the VH is at least 90% identical to SEQ ID NO: 2; and/or
a variable light domain (VL), wherein the VL is at least 90% identical to SEQ ID NO: 4.

16. The antigen binding construct of claim 1, wherein the antigen binding construct binds to CD4.

17. The antigen binding construct of claim 1, wherein the antigen binding construct is a minibody, and wherein the minibody is covalently linked to a detectable marker.

18. The antigen binding construct of claim 17, wherein the detectable marker is $^{18}$F or $^{89}$Zr.

19. The antigen binding construct of claim 1, wherein the antigen binding construct comprises a VH with T59, N61, or both, wherein the VH is a humanized VH; and wherein the antigen binding construct comprises a VL with A82, wherein the VL is a humanized VL.

* * * * *

SEQUENCE LISTING

<160> NUMBER OF SEQ ID NOS: 50

<210> SEQ ID NO 1
<211> LENGTH: 120

```
<212> TYPE: PRT
<213> ORGANISM: Artificial Sequence
<220> FEATURE:
<223> OTHER INFORMATION: MAX16H5

<400> SEQUENCE: 1

Glu Val Gln Leu Gln Gln Ser Gly Thr Val Leu Ala Arg Pro Gly Ala
1               5                   10                  15

Ser Val Gln Met Ser Cys Lys Ala Ser Gly Tyr Ser Phe Ala Asn Tyr
                20                  25                  30

Trp Met His Trp Val Lys Gln Arg Pro Gly Gln Gly Leu Gln Trp Ile
            35                  40                  45

Gly Ala Leu Tyr Pro Gly Asn Val Asp Thr Thr Tyr Asn Gln Lys Phe
    50                  55                  60

Lys Asp Lys Ala Lys Leu Thr Ala Val Thr Ser Ala Ser Thr Ala Tyr
65                  70                  75                  80

Met Glu Leu Ser Ser Leu Thr Asn Glu Asp Ser Ala Val Tyr Tyr Cys
                85                  90                  95

Thr Arg Met Gly Thr Thr Leu Glu Ala Pro Leu Asp Tyr Trp Gly Gln
            100                 105                 110

Gly Thr Thr Leu Thr Val Ser Ser
            115                 120

<210> SEQ ID NO 2
<211> LENGTH: 116
<212> TYPE: PRT
<213> ORGANISM: Artificial Sequence
<220> FEATURE:
<223> OTHER INFORMATION: IAB41

<400> SEQUENCE: 2

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Ala Asn Tyr
                20                  25                  30

Trp Met His Trp Val Arg Gln Ala Pro Gly Gln Arg Leu Glu Trp Ile
            35                  40                  45

Gly Ala Leu Tyr Pro Gly Asn Val Asp Thr Thr Tyr Asn Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Met Gly Thr Thr Leu Glu Ala Pro Leu Asp Tyr Trp Gly Gln
            100                 105                 110

Gly Thr Leu Val
            115

<210> SEQ ID NO 3
<211> LENGTH: 106
<212> TYPE: PRT
<213> ORGANISM: Artificial Sequence
<220> FEATURE:
<223> OTHER INFORMATION: MAX16H5

<400> SEQUENCE: 3

Gln Ile Val Leu Thr Gln Ser Pro Ala Ile Met Ser Ala Ser Pro Gly
1               5                   10                  15

Glu Lys Val Ala Met Thr Cys Ser Ala Arg Ser Ser Val Ser Tyr Leu
```

```
                    20                  25                  30
Tyr Trp Tyr Gln Gln Lys Pro Gly Ser Ser Pro Arg Leu Leu Ile Tyr
                35                  40                  45
Asp Thr Ser Asn Leu Ala Ser Gly Val Pro Val Arg Phe Ile Gly Ser
            50                  55                  60
Gly Ser Gly Thr Ser Tyr Ser Leu Thr Ile Ser Arg Met Glu Ala Glu
65                  70                  75                  80
Asp Ala Ala Thr Tyr Tyr Cys Gln Gln Trp Ser Asp Tyr Pro Leu Thr
                85                  90                  95
Phe Gly Ala Gly Thr Lys Leu Glu Leu Lys
            100                 105

<210> SEQ ID NO 4
<211> LENGTH: 106
<212> TYPE: PRT
<213> ORGANISM: Artificial Sequence
<220> FEATURE:
<223> OTHER INFORMATION: IAB41

<400> SEQUENCE: 4

Glu Ile Val Leu Thr Gln Ser Pro Ala Thr Leu Ser Leu Ser Pro Gly
1               5                   10                  15
Glu Arg Ala Thr Leu Ser Cys Ser Ala Arg Ser Ser Val Ser Tyr Leu
                20                  25                  30
Tyr Trp Tyr Gln Gln Lys Pro Gly Gln Ala Pro Arg Leu Leu Ile Tyr
                35                  40                  45
Asp Thr Ser Asn Leu Ala Ser Gly Ile Pro Asp Arg Phe Ser Gly Ser
            50                  55                  60
Gly Ser Gly Thr Asp Phe Thr Leu Thr Ile Ser Arg Leu Glu Pro Glu
65                  70                  75                  80
Asp Ala Ala Val Tyr Tyr Cys Gln Gln Trp Ser Asp Tyr Pro Leu Thr
                85                  90                  95
Phe Gly Gly Gly Thr Lys Leu Glu Ile Lys
            100                 105

<210> SEQ ID NO 5
<211> LENGTH: 377
<212> TYPE: PRT
<213> ORGANISM: Artificial Sequence
<220> FEATURE:
<223> OTHER INFORMATION: minibody

<400> SEQUENCE: 5

Glu Ile Val Leu Thr Gln Ser Pro Ala Thr Leu Ser Leu Ser Pro Gly
1               5                   10                  15
Glu Arg Ala Thr Leu Ser Cys Ser Ala Arg Ser Ser Val Ser Tyr Leu
                20                  25                  30
Tyr Trp Tyr Gln Gln Lys Pro Gly Gln Ala Pro Arg Leu Leu Ile Tyr
                35                  40                  45
Asp Thr Ser Asn Leu Ala Ser Gly Ile Pro Asp Arg Phe Ser Gly Ser
            50                  55                  60
Gly Ser Gly Thr Asp Phe Thr Leu Thr Ile Ser Arg Leu Glu Pro Glu
65                  70                  75                  80
Asp Ala Ala Val Tyr Tyr Cys Gln Gln Trp Ser Asp Tyr Pro Leu Thr
                85                  90                  95
Phe Gly Gly Gly Thr Lys Leu Glu Ile Lys Gly Ser Thr Ser Gly Gly
            100                 105                 110
```

Gly Ser Gly Gly Ser Gly Gly Gly Ser Ser Gln Val Gln Leu
            115                 120                 125

Val Gln Ser Gly Ala Glu Val Lys Lys Pro Gly Ala Ser Val Lys Val
    130                 135                 140

Ser Cys Lys Ala Ser Gly Tyr Ser Phe Ala Asn Tyr Trp Met His Trp
145                 150                 155                 160

Val Arg Gln Ala Pro Gly Gln Arg Leu Glu Trp Ile Gly Ala Leu Tyr
                165                 170                 175

Pro Gly Asn Val Asp Thr Thr Tyr Asn Gln Lys Phe Gln Gly Arg Val
            180                 185                 190

Thr Ile Thr Arg Asp Thr Ser Ala Ser Thr Ala Tyr Met Glu Leu Ser
        195                 200                 205

Ser Leu Arg Ser Glu Asp Thr Ala Val Tyr Tyr Cys Thr Arg Met Gly
210                 215                 220

Thr Thr Leu Glu Ala Pro Leu Asp Tyr Trp Gly Gln Gly Thr Leu Val
225                 230                 235                 240

Thr Val Ser Ser Glu Pro Lys Ser Ser Asp Lys Thr His Thr Cys Pro
                245                 250                 255

Pro Cys Pro Cys Gly Gly Gly Ser Ser Gly Gly Gly Ser Gly Gly
            260                 265                 270

Gln Pro Arg Glu Pro Gln Val Tyr Thr Leu Pro Pro Ser Arg Glu Glu
        275                 280                 285

Met Thr Lys Asn Gln Val Ser Leu Thr Cys Leu Val Lys Gly Phe Tyr
    290                 295                 300

Pro Ser Asp Ile Ala Val Glu Trp Glu Ser Asn Gly Gln Pro Glu Asn
305                 310                 315                 320

Asn Tyr Lys Thr Thr Pro Pro Val Leu Asp Ser Asp Gly Ser Phe Phe
                325                 330                 335

Leu Tyr Ser Lys Leu Thr Val Asp Lys Ser Arg Trp Gln Gln Gly Asn
            340                 345                 350

Val Phe Ser Cys Ser Val Met His Glu Ala Leu His Asn His Tyr Thr
        355                 360                 365

Gln Lys Ser Leu Ser Leu Ser Pro Gly
    370                 375

<210> SEQ ID NO 6
<211> LENGTH: 380
<212> TYPE: PRT
<213> ORGANISM: Artificial Sequence
<220> FEATURE:
<223> OTHER INFORMATION: minibody

<400> SEQUENCE: 6

Glu Ile Val Leu Thr Gln Ser Pro Ala Thr Leu Ser Leu Ser Pro Gly
1               5                   10                  15

Glu Arg Ala Thr Leu Ser Cys Ser Ala Arg Ser Ser Val Ser Tyr Leu
            20                  25                  30

Tyr Trp Tyr Gln Gln Lys Pro Gly Gln Ala Pro Arg Leu Leu Ile Tyr
        35                  40                  45

Asp Thr Ser Asn Leu Ala Ser Gly Ile Pro Asp Arg Phe Ser Gly Ser
    50                  55                  60

Gly Ser Gly Thr Asp Phe Thr Leu Thr Ile Ser Arg Leu Glu Pro Glu
65                  70                  75                  80

Asp Ala Ala Val Tyr Tyr Cys Gln Gln Trp Ser Asp Tyr Pro Leu Thr
                85                  90                  95

```
Phe Gly Gly Gly Thr Lys Leu Glu Ile Lys Gly Ser Thr Ser Gly Gly
                100                 105                 110

Gly Ser Gly Gly Ser Gly Gly Gly Ser Ser Gln Val Gln Leu
            115                 120                 125

Val Gln Ser Gly Ala Glu Val Lys Lys Pro Gly Ala Ser Val Lys Val
        130                 135                 140

Ser Cys Lys Ala Ser Gly Tyr Ser Phe Ala Asn Tyr Trp Met His Trp
145                 150                 155                 160

Val Arg Gln Ala Pro Gly Gln Arg Leu Glu Trp Ile Gly Ala Leu Tyr
                165                 170                 175

Pro Gly Asn Val Asp Thr Thr Tyr Asn Gln Lys Phe Gln Gly Arg Val
            180                 185                 190

Thr Ile Thr Arg Asp Thr Ser Ala Ser Thr Ala Tyr Met Glu Leu Ser
        195                 200                 205

Ser Leu Arg Ser Glu Asp Thr Ala Val Tyr Tyr Cys Thr Arg Met Gly
210                 215                 220

Thr Thr Leu Glu Ala Pro Leu Asp Tyr Trp Gly Gln Gly Thr Leu Val
225                 230                 235                 240

Thr Val Ser Ser Glu Pro Lys Ser Ser Asp Lys Thr His Thr Cys Pro
                245                 250                 255

Pro Cys Pro Cys Pro Cys Pro Cys Gly Gly Ser Ser Gly Gly Gly
            260                 265                 270

Ser Gly Gly Gln Pro Arg Glu Pro Gln Val Tyr Thr Leu Pro Pro Ser
        275                 280                 285

Arg Glu Glu Met Thr Lys Asn Gln Val Ser Leu Thr Cys Leu Val Lys
290                 295                 300

Gly Phe Tyr Pro Ser Asp Ile Ala Val Glu Trp Glu Ser Asn Gly Gln
305                 310                 315                 320

Pro Glu Asn Asn Tyr Lys Thr Thr Pro Pro Val Leu Asp Ser Asp Gly
                325                 330                 335

Ser Phe Phe Leu Tyr Ser Lys Leu Thr Val Asp Lys Ser Arg Trp Gln
            340                 345                 350

Gln Gly Asn Val Phe Ser Cys Ser Val Met His Glu Ala Leu His Asn
        355                 360                 365

His Tyr Thr Gln Lys Ser Leu Ser Leu Ser Pro Gly
370                 375                 380

<210> SEQ ID NO 7
<211> LENGTH: 377
<212> TYPE: PRT
<213> ORGANISM: Artificial Sequence
<220> FEATURE:
<223> OTHER INFORMATION: minbody

<400> SEQUENCE: 7

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Ala Asn Tyr
                20                  25                  30

Trp Met His Trp Val Arg Gln Ala Pro Gly Gln Arg Leu Glu Trp Ile
            35                  40                  45

Gly Ala Leu Tyr Pro Gly Asn Val Asp Thr Thr Tyr Asn Gln Lys Phe
        50                  55                  60

Gln Gly Arg Val Thr Ile Thr Arg Asp Thr Ser Ala Ser Thr Ala Tyr
65                  70                  75                  80
```

```
Met Glu Leu Ser Ser Leu Arg Ser Glu Asp Thr Ala Val Tyr Tyr Cys
                 85                  90                  95

Thr Arg Met Gly Thr Thr Leu Glu Ala Pro Leu Asp Tyr Trp Gly Gln
            100                 105                 110

Gly Thr Leu Val Thr Val Ser Ser Gly Ser Thr Ser Gly Gly Gly Ser
            115                 120                 125

Gly Gly Gly Ser Gly Gly Gly Ser Ser Glu Ile Val Leu Thr Gln
            130                 135                 140

Ser Pro Ala Thr Leu Ser Leu Ser Pro Gly Glu Arg Ala Thr Leu Ser
145                 150                 155                 160

Cys Ser Ala Arg Ser Ser Val Ser Tyr Leu Tyr Trp Tyr Gln Gln Lys
                165                 170                 175

Pro Gly Gln Ala Pro Arg Leu Leu Ile Tyr Asp Thr Ser Asn Leu Ala
                180                 185                 190

Ser Gly Ile Pro Asp Arg Phe Ser Gly Ser Gly Ser Gly Thr Asp Phe
                195                 200                 205

Thr Leu Thr Ile Ser Arg Leu Glu Pro Glu Asp Ala Ala Val Tyr Tyr
            210                 215                 220

Cys Gln Gln Trp Ser Asp Tyr Pro Leu Thr Phe Gly Gly Gly Thr Lys
225                 230                 235                 240

Leu Glu Ile Lys Glu Pro Lys Ser Ser Asp Lys Thr His Thr Cys Pro
                245                 250                 255

Pro Cys Pro Cys Gly Gly Gly Ser Ser Gly Gly Gly Ser Gly Gly
                260                 265                 270

Gln Pro Arg Glu Pro Gln Val Tyr Thr Leu Pro Pro Ser Arg Glu Glu
                275                 280                 285

Met Thr Lys Asn Gln Val Ser Leu Thr Cys Leu Val Lys Gly Phe Tyr
290                 295                 300

Pro Ser Asp Ile Ala Val Glu Trp Glu Ser Asn Gly Gln Pro Glu Asn
305                 310                 315                 320

Asn Tyr Lys Thr Thr Pro Pro Val Leu Asp Ser Asp Gly Ser Phe Phe
                325                 330                 335

Leu Tyr Ser Lys Leu Thr Val Asp Lys Ser Arg Trp Gln Gln Gly Asn
                340                 345                 350

Val Phe Ser Cys Ser Val Met His Glu Ala Leu His Asn His Tyr Thr
                355                 360                 365

Gln Lys Ser Leu Ser Leu Ser Pro Gly
            370                 375

<210> SEQ ID NO 8
<211> LENGTH: 380
<212> TYPE: PRT
<213> ORGANISM: Artificial Sequence
<220> FEATURE:
<223> OTHER INFORMATION: minibody

<400> SEQUENCE: 8

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Ala Asn Tyr
                20                  25                  30

Trp Met His Trp Val Arg Gln Ala Pro Gly Gln Arg Leu Glu Trp Ile
            35                  40                  45

Gly Ala Leu Tyr Pro Gly Asn Val Asp Thr Thr Tyr Asn Gln Lys Phe
50                  55                  60
```

```
Gln Gly Arg Val Thr Ile Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Thr Arg Met Gly Thr Thr Leu Glu Ala Pro Leu Asp Tyr Trp Gly Gln
            100                 105                 110

Gly Thr Leu Val Thr Val Ser Ser Gly Ser Thr Ser Gly Gly Gly Ser
        115                 120                 125

Gly Gly Gly Ser Gly Gly Gly Ser Ser Glu Ile Val Leu Thr Gln
    130                 135                 140

Ser Pro Ala Thr Leu Ser Leu Ser Pro Gly Glu Arg Ala Thr Leu Ser
145                 150                 155                 160

Cys Ser Ala Arg Ser Ser Val Ser Tyr Leu Tyr Trp Tyr Gln Gln Lys
                165                 170                 175

Pro Gly Gln Ala Pro Arg Leu Leu Ile Tyr Asp Thr Ser Asn Leu Ala
            180                 185                 190

Ser Gly Ile Pro Asp Arg Phe Ser Gly Ser Gly Ser Thr Asp Phe
        195                 200                 205

Thr Leu Thr Ile Ser Arg Leu Glu Pro Glu Asp Ala Ala Val Tyr Tyr
    210                 215                 220

Cys Gln Gln Trp Ser Asp Tyr Pro Leu Thr Phe Gly Gly Thr Lys
225                 230                 235                 240

Leu Glu Ile Lys Glu Pro Lys Ser Ser Asp Lys Thr His Thr Cys Pro
                245                 250                 255

Pro Cys Pro Pro Cys Pro Pro Cys Gly Gly Gly Ser Gly Gly Gly
            260                 265                 270

Ser Gly Gly Gln Pro Arg Glu Pro Gln Val Tyr Thr Leu Pro Pro Ser
        275                 280                 285

Arg Glu Glu Met Thr Lys Asn Gln Val Ser Leu Thr Cys Leu Val Lys
                290                 295                 300

Gly Phe Tyr Pro Ser Asp Ile Ala Val Glu Trp Glu Ser Asn Gly Gln
305                 310                 315                 320

Pro Glu Asn Asn Tyr Lys Thr Thr Pro Pro Val Leu Asp Ser Asp Gly
                325                 330                 335

Ser Phe Phe Leu Tyr Ser Lys Leu Thr Val Asp Lys Ser Arg Trp Gln
            340                 345                 350

Gln Gly Asn Val Phe Ser Cys Ser Val Met His Glu Ala Leu His Asn
        355                 360                 365

His Tyr Thr Gln Lys Ser Leu Ser Leu Ser Pro Gly
    370                 375                 380

<210> SEQ ID NO 9
<211> LENGTH: 1194
<212> TYPE: PRT
<213> ORGANISM: Artificial Sequence
<220> FEATURE:
<223> OTHER INFORMATION: hinge

<400> SEQUENCE: 9

Ala Thr Gly Gly Ala Gly Ala Cys Cys Gly Ala Cys Ala Cys Ala Cys
 1               5                  10                  15

Thr Gly Cys Thr Gly Cys Thr Gly Thr Gly Gly Thr Gly Cys Thr
            20                  25                  30

Gly Cys Thr Gly Cys Thr Gly Thr Gly Gly Gly Thr Gly Cys Cys Cys
        35                  40                  45
```

-continued

```
Gly Gly Ala Ala Gly Cys Ala Cys Cys Gly Gly Ala Gly Ala Ala Ala
    50                  55                  60
Thr Cys Gly Thr Gly Cys Thr Gly Ala Cys Cys Cys Ala Gly Thr Cys
65                  70                  75                  80

Cys Cys Cys Thr Gly Cys Thr Ala Cys Cys Cys Thr Gly Ala Gly Cys
                85                  90                  95

Cys Thr Gly Ala Gly Cys Cys Cys Thr Gly Gly Cys Gly Ala Ala Ala
            100                 105                 110

Gly Gly Gly Cys Cys Ala Cys Ala Cys Thr Gly Thr Cys Cys Thr Gly
        115                 120                 125

Cys Thr Cys Cys Gly Cys Cys Ala Gly Gly Ala Gly Cys Ala Gly Cys
    130                 135                 140

Gly Thr Gly Ala Gly Cys Thr Ala Thr Cys Thr Gly Thr Ala Cys Thr
145                 150                 155                 160
Gly Gly Thr Ala Cys Cys Ala Gly Cys Ala Gly Ala Ala Gly Cys Cys
                165                 170                 175

Cys Gly Gly Ala Cys Ala Gly Gly Cys Cys Cys Cys Thr Ala Gly Gly
            180                 185                 190

Cys Thr Gly Cys Thr Gly Ala Thr Cys Thr Ala Cys Gly Ala Cys Ala
        195                 200                 205

Cys Cys Ala Gly Cys Ala Ala Cys Cys Thr Gly Gly Cys Cys Ala Gly
    210                 215                 220

Cys Gly Gly Cys Ala Thr Cys Cys Cys Thr Gly Ala Cys Ala Gly Gly
225                 230                 235                 240

Thr Thr Cys Thr Cys Cys Gly Gly Cys Thr Cys Cys Gly Gly Cys Ala
                245                 250                 255

Gly Cys Gly Gly Cys Ala Cys Ala Gly Ala Thr Thr Thr Cys Ala Cys
            260                 265                 270

Cys Cys Thr Gly Ala Cys Cys Ala Thr Cys Thr Cys Cys Ala Gly Ala
        275                 280                 285

Cys Thr Gly Gly Ala Gly Cys Cys Cys Gly Ala Ala Gly Ala Cys Gly
    290                 295                 300

Cys Cys Gly Cys Cys Gly Thr Cys Thr Ala Cys Thr Ala Cys Thr Gly
305                 310                 315                 320

Cys Cys Ala Gly Cys Ala Gly Thr Gly Gly Ala Gly Cys Gly Ala Thr
                325                 330                 335

Thr Ala Thr Cys Cys Thr Cys Thr Gly Ala Cys Cys Thr Thr Cys Gly
            340                 345                 350

Gly Cys Gly Gly Cys Gly Gly Cys Ala Cys Cys Ala Ala Gly Cys Thr
        355                 360                 365

Cys Gly Ala Gly Ala Thr Cys Ala Ala Gly Gly Gly Cys Ala Gly Cys
    370                 375                 380

Ala Cys Cys Ala Gly Cys Gly Gly Ala Gly Gly Cys Gly Gly Cys Ala
385                 390                 395                 400

Gly Cys Gly Gly Cys Gly Gly Cys Gly Gly Cys Ala Gly Cys Gly Gly
                405                 410                 415

Cys Gly Gly Ala Gly Gly Ala Gly Gly Cys Ala Gly Cys Ala Gly Cys
            420                 425                 430

Cys Ala Ala Gly Thr Gly Cys Ala Gly Cys Thr Gly Gly Thr Gly Cys
        435                 440                 445

Ala Gly Ala Gly Cys Gly Gly Cys Gly Cys Cys Gly Ala Gly Gly Thr
    450                 455                 460

Gly Ala Ala Gly Ala Ala Gly Cys Cys Thr Gly Gly Cys Gly Cys Thr
```

-continued

```
465                 470                 475                 480

Ala Gly Cys Gly Thr Gly Ala Ala Gly Gly Thr Gly Thr Cys Cys Thr
                485                 490                 495
Gly Thr Ala Ala Gly Gly Cys Thr Thr Cys Cys Gly Gly Cys Thr Ala
            500                 505                 510

Cys Ala Gly Cys Thr Thr Cys Gly Cys Cys Ala Ala Cys Thr Ala Cys
        515                 520                 525

Thr Gly Gly Ala Thr Gly Cys Ala Cys Thr Gly Gly Gly Thr Cys Ala
    530                 535                 540

Gly Ala Cys Ala Gly Gly Cys Thr Cys Cys Cys Gly Gly Cys Cys Ala
545                 550                 555                 560
Gly Ala Gly Gly Cys Thr Gly Gly Ala Ala Thr Gly Gly Ala Thr Cys
                565                 570                 575

Gly Gly Cys Gly Cys Cys Cys Thr Gly Thr Ala Cys Cys Cys Cys Gly
            580                 585                 590

Gly Cys Ala Ala Cys Gly Thr Gly Gly Ala Thr Ala Cys Cys Ala Cys
        595                 600                 605

Cys Thr Ala Cys Ala Ala Cys Cys Ala Gly Ala Ala Gly Thr Thr Cys
    610                 615                 620

Cys Ala Gly Gly Gly Cys Ala Gly Ala Gly Thr Cys Ala Cys Cys Ala
625                 630                 635                 640

Thr Thr Ala Cys Cys Ala Gly Gly Gly Ala Cys Ala Cys Ala Ala Gly
                645                 650                 655

Cys Gly Cys Cys Ala Gly Cys Ala Cys Cys Gly Cys Thr Thr Ala Thr
            660                 665                 670

Ala Thr Gly Gly Ala Gly Cys Thr Gly Thr Cys Cys Thr Cys Cys Cys
        675                 680                 685

Thr Cys Ala Gly Gly Ala Gly Cys Gly Ala Gly Gly Ala Cys Ala Cys
    690                 695                 700

Cys Gly Cys Cys Gly Thr Cys Thr Ala Thr Thr Ala Cys Thr Gly Cys
705                 710                 715                 720

Ala Cys Cys Ala Gly Gly Ala Thr Gly Gly Gly Cys Ala Cys Cys Ala
                725                 730                 735

Cys Ala Cys Thr Gly Gly Ala Gly Gly Cys Thr Cys Cys Thr Cys Thr
            740                 745                 750

Gly Gly Ala Cys Thr Ala Thr Thr Gly Gly Gly Gly Cys Cys Ala Gly
        755                 760                 765

Gly Gly Cys Ala Cys Ala Cys Thr Gly Gly Thr Gly Ala Cys Ala Gly
    770                 775                 780

Thr Gly Thr Cys Cys Thr Cys Cys Gly Ala Gly Cys Cys Cys Ala Ala
785                 790                 795                 800

Ala Ala Gly Cys Ala Gly Cys Gly Ala Thr Ala Ala Gly Ala Cys Cys
                805                 810                 815

Cys Ala Cys Ala Cys Cys Thr Gly Cys Cys Cys Thr Cys Cys Thr Thr
            820                 825                 830

Gly Cys Cys Cys Thr Cys Cys Thr Thr Gly Thr Gly Gly Cys Gly Gly
        835                 840                 845

Ala Gly Gly Ala Thr Cys Cys Ala Gly Cys Gly Gly Ala Gly Gly Ala
    850                 855                 860

Gly Gly Ala Ala Gly Cys Gly Gly Ala Gly Gly Cys Cys Ala Ala Cys
865                 870                 875                 880

Cys Cys Ala Gly Gly Gly Ala Ala Cys Cys Thr Cys Ala Gly Gly Thr
                885                 890                 895
```

```
Gly Thr Ala Cys Ala Cys Ala Cys Thr Cys Cys Cys Cys Cys Cys
                900                 905                 910

Ala Gly Cys Ala Gly Gly Ala Gly Gly Ala Gly Thr Gly Ala
        915                 920                 925

Cys Cys Ala Ala Gly Ala Ala Cys Cys Ala Gly Gly Thr Gly Ala Gly
    930                 935                 940

Cys Cys Thr Gly Ala Cys Thr Gly Cys Cys Thr Cys Gly Thr Gly
945                 950                 955                 960

Ala Ala Ala Gly Gly Cys Thr Thr Cys Thr Ala Cys Cys Cys Ala
                965                 970                 975

Gly Cys Gly Ala Cys Ala Thr Cys Gly Cys Cys Gly Thr Gly Ala
                980                 985                 990

Gly Thr Gly Gly Gly Ala Gly Ala  Gly Cys Ala Ala Cys  Gly Gly Cys
                995                 1000                1005

Cys Ala  Ala Cys Cys Cys Gly  Ala Ala Ala Ala Cys  Ala Ala Cys
         1010                1015                   1020

Thr Ala  Cys Ala Ala Ala Ala  Cys Cys Ala Cys Cys  Cys Cys Cys
         1025                1030                   1035

Cys Cys  Thr Gly Thr Cys Cys  Thr Gly Gly Ala Cys  Ala Gly Cys
         1040                1045                   1050

Gly Ala  Thr Gly Gly Cys Ala  Gly Cys Thr Thr Cys  Thr Thr Cys
         1055                1060                   1065

Cys Thr  Cys Thr Ala Cys Ala  Gly Cys Ala Ala Gly  Cys Thr Gly
         1070                1075                   1080

Ala Cys  Cys Gly Thr Gly Gly  Ala Cys Ala Ala Gly  Ala Gly Cys
         1085                1090                   1095

Ala Gly  Ala Thr Gly Gly Cys  Ala Gly Cys Ala Gly  Gly Gly Cys
         1100                1105                   1110

Ala Ala  Cys Gly Thr Gly Thr  Thr Cys Thr Cys Cys  Thr Gly Thr
         1115                1120                   1125

Thr Cys  Cys Gly Thr Gly Ala  Thr Gly Cys Ala Cys  Gly Ala Gly
         1130                1135                   1140

Gly Cys  Cys Cys Thr Cys Cys  Ala Cys Ala Ala Cys  Cys Ala Cys
         1145                1150                   1155

Thr Ala  Cys Ala Cys Cys Cys  Ala Gly Ala Ala Ala  Thr Cys Cys
         1160                1165                   1170

Cys Thr  Gly Thr Cys Cys Cys  Thr Gly Thr Cys Cys  Cys Cys Cys
         1175                1180                   1185

Gly Gly  Cys Thr Gly Ala
         1190

<210> SEQ ID NO 10
<211> LENGTH: 1194
<212> TYPE: PRT
<213> ORGANISM: Artificial Sequence
<220> FEATURE:
<223> OTHER INFORMATION: hinge

<400> SEQUENCE: 10

Ala Thr Gly Gly Ala Gly Ala Cys Cys Gly Ala Thr Ala Cys Cys Cys
1               5                   10                  15

Thr Cys Cys Thr Gly Cys Thr Cys Thr Gly Gly Thr Gly Cys Thr
                20                  25                  30

Gly Cys Thr Gly Cys Thr Gly Thr Gly Gly Gly Thr Gly Cys Cys Thr
            35                  40                  45
```

-continued

```
Gly Gly Ala Ala Gly Cys Ala Cys Ala Gly Gly Cys Cys Ala Gly Gly
    50                  55                  60

Thr Gly Cys Ala Gly Cys Thr Gly Gly Thr Gly Cys Ala Gly Ala Gly
65                  70                  75                  80

Cys Gly Gly Ala Gly Cys Cys Gly Ala Gly Gly Thr Gly Ala Ala Ala
                85                  90                  95

Ala Ala Ala Cys Cys Cys Gly Gly Cys Gly Cys Cys Thr Cys Cys Gly
            100                 105                 110

Thr Gly Ala Ala Gly Gly Thr Gly Ala Gly Cys Thr Gly Cys Ala Ala
        115                 120                 125

Gly Gly Cys Cys Ala Gly Cys Gly Gly Cys Thr Ala Cys Ala Gly Cys
    130                 135                 140

Thr Thr Cys Gly Cys Cys Ala Ala Cys Thr Ala Cys Thr Gly Gly Ala
145                 150                 155                 160

Thr Gly Cys Ala Cys Thr Gly Gly Gly Thr Gly Ala Gly Gly Cys Ala
                165                 170                 175

Gly Gly Cys Cys Cys Cys Thr Gly Gly Cys Cys Ala Gly Ala Gly Gly
            180                 185                 190

Cys Thr Gly Gly Ala Ala Thr Gly Gly Ala Thr Thr Gly Gly Cys Gly
        195                 200                 205

Cys Cys Cys Thr Gly Thr Ala Cys Cys Cys Thr Gly Gly Cys Ala Ala
    210                 215                 220

Cys Gly Thr Gly Gly Ala Cys Ala Cys Cys Ala Cys Cys Thr Ala Cys
225                 230                 235                 240

Ala Ala Cys Cys Ala Gly Ala Ala Ala Thr Thr Cys Cys Ala Gly Gly
                245                 250                 255

Gly Cys Ala Gly Gly Gly Thr Gly Ala Cys Cys Ala Thr Cys Ala Cys
            260                 265                 270

Cys Ala Gly Ala Gly Ala Thr Ala Cys Cys Ala Gly Cys Gly Cys Cys
        275                 280                 285

Ala Gly Cys Ala Cys Cys Gly Cys Thr Thr Ala Cys Ala Thr Gly Gly
    290                 295                 300

Ala Ala Cys Thr Gly Ala Gly Cys Ala Gly Cys Cys Thr Gly Ala Gly
305                 310                 315                 320

Gly Ala Gly Cys Gly Ala Gly Gly Ala Thr Ala Cys Cys Gly Cys Cys
                325                 330                 335

Gly Thr Gly Thr Ala Cys Thr Ala Cys Thr Gly Cys Ala Cys Cys Ala
            340                 345                 350

Gly Gly Ala Thr Gly Gly Gly Cys Ala Cys Ala Ala Cys Cys Cys Thr
        355                 360                 365

Gly Gly Ala Gly Gly Cys Thr Cys Cys Cys Cys Thr Gly Gly Ala Thr
    370                 375                 380

Thr Ala Cys Thr Gly Gly Gly Gly Cys Cys Ala Gly Gly Gly Cys Ala
385                 390                 395                 400

Cys Ala Cys Thr Gly Gly Thr Gly Ala Cys Ala Gly Thr Cys Ala Gly
                405                 410                 415

Cys Ala Gly Cys Gly Gly Cys Ala Gly Cys Ala Cys Ala Ala Gly Cys
            420                 425                 430

Gly Gly Ala Gly Gly Ala Gly Gly Ala Ala Gly Cys Gly Gly Ala Gly
        435                 440                 445

Gly Ala Gly Gly Cys Ala Gly Cys Gly Gly Cys Gly Gly Ala Gly Gly
    450                 455                 460
```

```
Ala Gly Gly Ala Ala Gly Cys Ala Gly Cys Ala Gly Ala Thr Cys
465                 470                 475                 480

Gly Thr Gly Cys Thr Gly Ala Cys Cys Ala Gly Thr Cys Cys Cys
            485                 490                 495

Cys Cys Gly Cys Thr Ala Cys Ala Cys Thr Gly Ala Gly Cys Cys Thr
            500                 505                 510

Gly Ala Gly Cys Cys Cys Thr Gly Gly Cys Gly Ala Gly Ala Gly Ala
        515                 520                 525

Gly Cys Cys Ala Cys Cys Cys Thr Gly Thr Cys Cys Thr Gly Cys Thr
        530                 535                 540

Cys Cys Gly Cys Cys Ala Gly Ala Ala Gly Cys Thr Cys Cys Gly Thr
545                 550                 555                 560

Gly Ala Gly Cys Thr Ala Cys Cys Thr Gly Thr Ala Cys Thr Gly Gly
            565                 570                 575

Thr Ala Cys Cys Ala Gly Cys Ala Gly Ala Ala Cys Cys Thr Gly
            580                 585                 590

Gly Cys Cys Ala Gly Gly Cys Cys Cys Cys Ala Gly Gly Cys Thr
        595                 600                 605

Gly Cys Thr Gly Ala Thr Cys Thr Ala Thr Gly Ala Cys Ala Cys Cys
        610                 615                 620

Ala Gly Cys Ala Ala Cys Cys Thr Gly Gly Cys Cys Thr Cys Cys Gly
625                 630                 635                 640

Gly Cys Ala Thr Thr Cys Cys Cys Gly Ala Cys Ala Gly Gly Thr Thr
            645                 650                 655

Cys Ala Gly Cys Gly Gly Cys Ala Gly Cys Gly Gly Ala Thr Cys Cys
            660                 665                 670

Gly Gly Ala Ala Cys Cys Gly Ala Cys Thr Thr Cys Ala Cys Cys Cys
        675                 680                 685

Thr Gly Ala Cys Cys Ala Thr Cys Thr Cys Cys Ala Gly Ala Cys Thr
690                 695                 700

Cys Gly Ala Gly Cys Cys Cys Gly Ala Gly Gly Ala Thr Gly Cys Cys
705                 710                 715                 720

Gly Cys Cys Gly Thr Gly Thr Ala Thr Ala Cys Thr Gly Cys Cys
        725                 730                 735

Ala Gly Cys Ala Ala Thr Gly Gly Ala Gly Cys Gly Ala Thr Thr Ala
            740                 745                 750

Thr Cys Cys Thr Cys Thr Gly Ala Cys Cys Thr Thr Thr Gly Gly Cys
    755                 760                 765

Gly Gly Ala Gly Gly Cys Ala Cys Cys Ala Ala Gly Cys Thr Cys Gly
    770                 775                 780

Ala Gly Ala Thr Cys Ala Ala Gly Ala Gly Cys Cys Cys Ala Ala
785                 790                 795                 800

Ala Thr Cys Cys Thr Cys Cys Gly Ala Thr Ala Ala Ala Cys Cys
            805                 810                 815

Cys Ala Cys Ala Cys Cys Thr Gly Cys Cys Thr Cys Cys Thr Thr
        820                 825                 830

Gly Thr Cys Cys Thr Cys Cys Thr Thr Gly Thr Gly Cys Gly Gly
        835                 840                 845

Cys Gly Gly Cys Thr Cys Cys Ala Gly Cys Gly Gly Ala Gly Gly Cys
        850                 855                 860

Gly Gly Cys Thr Cys Cys Gly Gly Cys Gly Gly Ala Cys Ala Gly Cys
865                 870                 875                 880

Cys Cys Ala Gly Ala Gly Ala Gly Cys Cys Thr Cys Ala Gly Gly Thr
```

885                 890                 895
Cys Thr Ala Cys Ala Cys Cys Thr Gly Cys Cys Cys Cys Thr
                  900                 905                 910

Ala Gly Cys Ala Gly Gly Gly Ala Ala Gly Ala Thr Gly Ala
              915                 920                 925

Cys Cys Ala Ala Gly Ala Cys Cys Ala Gly Thr Gly Ala Gly
          930                 935                 940

Cys Cys Thr Gly Ala Cys Cys Thr Gly Thr Cys Thr Gly Gly Thr Gly
945                 950                 955                 960

Ala Ala Gly Gly Gly Cys Thr Thr Cys Thr Ala Cys Cys Cys Thr
              965                 970                 975

Cys Cys Gly Ala Thr Ala Thr Gly Cys Cys Gly Thr Cys Gly Ala
          980                 985                 990

Gly Thr Gly Gly Gly Ala Gly Thr  Cys Cys Ala Ala Cys  Gly Gly Cys
              995                 1000                1005

Cys Ala  Gly Cys Cys Gly  Ala Ala Ala Ala Cys  Ala Ala Cys
    1010                 1015                1020

Thr Ala  Cys Ala Ala Ala  Cys Ala Cys Cys  Cys Cys Cys
    1025                 1030                1035

Cys Cys  Cys Gly Thr Gly  Cys  Thr Cys Gly Ala Cys  Thr Cys Cys
    1040                 1045                1050

Gly Ala  Cys Gly Gly Thr Thr  Cys Thr Thr Thr  Thr Thr Cys
    1055                 1060                1065

Cys Thr  Cys Thr Ala Cys  Thr Cys Cys Ala Ala Gly  Cys Thr Gly
    1070                 1075                1080

Ala Cys  Cys Gly Thr Cys Gly  Ala Cys Ala Ala Gly  Thr Cys Cys
    1085                 1090                1095

Ala Gly  Gly Thr Gly Gly  Cys Ala Gly Cys Ala Gly  Gly Gly Cys
    1100                 1105                1110

Ala Ala  Cys Gly Thr Gly Thr  Cys Ala Gly Cys  Thr Gly Cys
    1115                 1120                1125

Ala Gly  Cys Gly Thr Gly Ala  Thr Gly Cys Ala Cys  Gly Ala Gly
    1130                 1135                1140

Gly Cys  Cys Cys Thr Cys Cys  Ala Cys Ala Ala Cys  Cys Ala Cys
    1145                 1150                1155

Thr Ala  Cys Ala Cys Cys Cys  Ala Gly Ala Ala Ala  Thr Cys Cys
    1160                 1165                1170

Cys Thr  Cys Thr Cys Cys Cys  Thr Gly Ala Gly Cys  Cys Cys Cys
    1175                 1180                1185

Gly Gly  Cys Thr Gly Ala
    1190

<210> SEQ ID NO 11
<211> LENGTH: 234
<212> TYPE: PRT
<213> ORGANISM: Artificial Sequence
<220> FEATURE:
<223> OTHER INFORMATION: Cys-Diabody

<400> SEQUENCE: 11

Glu Ile Val Leu Thr Gln Ser Pro Ala Thr Leu Ser Leu Ser Pro Gly
1               5                   10                  15

Glu Arg Ala Thr Leu Ser Cys Ser Ala Arg Ser Ser Val Ser Tyr Leu
            20                  25                  30

Tyr Trp Tyr Gln Gln Lys Pro Gly Gln Ala Pro Arg Leu Leu Ile Tyr

```
                35                  40                  45
Asp Thr Ser Asn Leu Ala Ser Gly Ile Pro Asp Arg Phe Ser Gly Ser
 50                  55                  60

Gly Ser Gly Thr Asp Phe Thr Leu Thr Ile Ser Arg Leu Glu Pro Glu
 65                  70                  75                  80

Asp Ala Ala Val Tyr Tyr Cys Gln Gln Trp Ser Asp Tyr Pro Leu Thr
                 85                  90                  95

Phe Gly Gly Gly Thr Lys Leu Glu Ile Lys Ser Gly Gly Gly Gly Gln
                100                 105                 110

Val Gln Leu Val Gln Ser Gly Ala Glu Val Lys Lys Pro Gly Ala Ser
                115                 120                 125

Val Lys Val Ser Cys Lys Ala Ser Gly Tyr Ser Phe Ala Asn Tyr Trp
                130                 135                 140

Met His Trp Val Arg Gln Ala Pro Gly Gln Arg Leu Glu Trp Ile Gly
145                 150                 155                 160

Ala Leu Tyr Pro Gly Asn Val Asp Thr Thr Tyr Asn Gln Lys Phe Gln
                165                 170                 175

Gly Arg Val Thr Ile Thr Arg Asp Thr Ser Ala Ser Thr Ala Tyr Met
                180                 185                 190

Glu Leu Ser Ser Leu Arg Ser Glu Asp Thr Ala Val Tyr Tyr Cys Thr
                195                 200                 205

Arg Met Gly Thr Thr Leu Glu Ala Pro Leu Asp Tyr Trp Gly Gln Gly
                210                 215                 220

Thr Leu Val Thr Val Ser Ser Gly Gly Cys
225                 230

<210> SEQ ID NO 12
<211> LENGTH: 237
<212> TYPE: PRT
<213> ORGANISM: Artificial Sequence
<220> FEATURE:
<223> OTHER INFORMATION: cys-diabody

<400> SEQUENCE: 12

Glu Ile Val Leu Thr Gln Ser Pro Ala Thr Leu Ser Leu Ser Pro Gly
 1               5                  10                  15

Glu Arg Ala Thr Leu Ser Cys Ser Ala Arg Ser Ser Val Ser Tyr Leu
                 20                  25                  30

Tyr Trp Tyr Gln Gln Lys Pro Gly Gln Ala Pro Arg Leu Leu Ile Tyr
                 35                  40                  45

Asp Thr Ser Asn Leu Ala Ser Gly Ile Pro Asp Arg Phe Ser Gly Ser
 50                  55                  60

Gly Ser Gly Thr Asp Phe Thr Leu Thr Ile Ser Arg Leu Glu Pro Glu
 65                  70                  75                  80

Asp Ala Ala Val Tyr Tyr Cys Gln Gln Trp Ser Asp Tyr Pro Leu Thr
                 85                  90                  95

Phe Gly Gly Gly Thr Lys Leu Glu Ile Lys Ser Gly Gly Gly Gly Gln
                100                 105                 110

Val Gln Leu Val Gln Ser Gly Ala Glu Val Lys Lys Pro Gly Ala Ser
                115                 120                 125

Val Lys Val Ser Cys Lys Ala Ser Gly Tyr Ser Phe Ala Asn Tyr Trp
                130                 135                 140

Met His Trp Val Arg Gln Ala Pro Gly Gln Arg Leu Glu Trp Ile Gly
145                 150                 155                 160

Ala Leu Tyr Pro Gly Asn Val Asp Thr Thr Tyr Asn Gln Lys Phe Gln
```

165                 170                 175
Gly Arg Val Thr Ile Thr Arg Asp Thr Ser Ala Ser Thr Ala Tyr Met
            180                 185                 190

Glu Leu Ser Ser Leu Arg Ser Glu Asp Thr Ala Val Tyr Tyr Cys Thr
        195                 200                 205

Arg Met Gly Thr Thr Leu Glu Ala Pro Leu Asp Tyr Trp Gly Gln Gly
    210                 215                 220

Thr Leu Val Thr Val Ser Ser Gly Gly Cys Pro Pro Cys
225                 230                 235

<210> SEQ ID NO 13
<211> LENGTH: 240
<212> TYPE: PRT
<213> ORGANISM: Artificial Sequence
<220> FEATURE:
<223> OTHER INFORMATION: cys-diabody

<400> SEQUENCE: 13

Glu Ile Val Leu Thr Gln Ser Pro Ala Thr Leu Ser Leu Ser Pro Gly
1               5                   10                  15

Glu Arg Ala Thr Leu Ser Cys Ser Ala Arg Ser Ser Val Ser Tyr Leu
            20                  25                  30

Tyr Trp Tyr Gln Gln Lys Pro Gly Gln Ala Pro Arg Leu Leu Ile Tyr
        35                  40                  45

Asp Thr Ser Asn Leu Ala Ser Gly Ile Pro Asp Arg Phe Ser Gly Ser
    50                  55                  60

Gly Ser Gly Thr Asp Phe Thr Leu Thr Ile Ser Arg Leu Glu Pro Glu
65                  70                  75                  80

Asp Ala Ala Val Tyr Tyr Cys Gln Gln Trp Ser Asp Tyr Pro Leu Thr
                85                  90                  95

Phe Gly Gly Gly Thr Lys Leu Glu Ile Lys Ser Gly Gly Gly Gly Gln
            100                 105                 110

Val Gln Leu Val Gln Ser Gly Ala Glu Val Lys Lys Pro Gly Ala Ser
        115                 120                 125

Val Lys Val Ser Cys Lys Ala Ser Gly Tyr Ser Phe Ala Asn Tyr Trp
    130                 135                 140

Met His Trp Val Arg Gln Ala Pro Gly Gln Arg Leu Glu Trp Ile Gly
145                 150                 155                 160

Ala Leu Tyr Pro Gly Asn Val Asp Thr Thr Tyr Asn Gln Lys Phe Gln
                165                 170                 175

Gly Arg Val Thr Ile Thr Arg Asp Thr Ser Ala Ser Thr Ala Tyr Met
            180                 185                 190

Glu Leu Ser Ser Leu Arg Ser Glu Asp Thr Ala Val Tyr Tyr Cys Thr
        195                 200                 205

Arg Met Gly Thr Thr Leu Glu Ala Pro Leu Asp Tyr Trp Gly Gln Gly
    210                 215                 220

Thr Leu Val Thr Val Ser Ser Gly Gly Cys Pro Pro Cys Pro Pro Cys
225                 230                 235                 240

<210> SEQ ID NO 14
<211> LENGTH: 243
<212> TYPE: PRT
<213> ORGANISM: Artificial Sequence
<220> FEATURE:
<223> OTHER INFORMATION: cys-diabody

<400> SEQUENCE: 14

```
Glu Ile Val Leu Thr Gln Ser Pro Ala Thr Leu Ser Leu Ser Pro Gly
1               5                   10                  15

Glu Arg Ala Thr Leu Ser Cys Ser Ala Arg Ser Ser Val Ser Tyr Leu
            20                  25                  30

Tyr Trp Tyr Gln Gln Lys Pro Gly Gln Ala Pro Arg Leu Leu Ile Tyr
        35                  40                  45

Asp Thr Ser Asn Leu Ala Ser Gly Ile Pro Asp Arg Phe Ser Gly Ser
    50                  55                  60

Gly Ser Gly Thr Asp Phe Thr Leu Thr Ile Ser Arg Leu Glu Pro Glu
65                  70                  75                  80

Asp Ala Ala Val Tyr Tyr Cys Gln Gln Trp Ser Asp Tyr Pro Leu Thr
                85                  90                  95

Phe Gly Gly Gly Thr Lys Leu Glu Ile Lys Ser Gly Gly Gly Gly Gln
            100                 105                 110

Val Gln Leu Val Gln Ser Gly Ala Glu Val Lys Lys Pro Gly Ala Ser
        115                 120                 125

Val Lys Val Ser Cys Lys Ala Ser Gly Tyr Ser Phe Ala Asn Tyr Trp
    130                 135                 140

Met His Trp Val Arg Gln Ala Pro Gly Gln Arg Leu Glu Trp Ile Gly
145                 150                 155                 160

Ala Leu Tyr Pro Gly Asn Val Asp Thr Thr Tyr Asn Gln Lys Phe Gln
                165                 170                 175

Gly Arg Val Thr Ile Thr Arg Asp Thr Ser Ala Ser Thr Ala Tyr Met
            180                 185                 190

Glu Leu Ser Ser Leu Arg Ser Glu Asp Thr Ala Val Tyr Tyr Cys Thr
        195                 200                 205

Arg Met Gly Thr Thr Leu Glu Ala Pro Leu Asp Tyr Trp Gly Gln Gly
    210                 215                 220

Thr Leu Val Thr Val Ser Ser Gly Gly Cys Pro Cys Pro Pro Cys
225                 230                 235                 240

Pro Pro Cys

<210> SEQ ID NO 15
<211> LENGTH: 234
<212> TYPE: PRT
<213> ORGANISM: Artificial Sequence
<220> FEATURE:
<223> OTHER INFORMATION: cys-diabody

<400> SEQUENCE: 15

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Ala Asn Tyr
            20                  25                  30

Trp Met His Trp Val Arg Gln Ala Pro Gly Gln Arg Leu Glu Trp Ile
        35                  40                  45

Gly Ala Leu Tyr Pro Gly Asn Val Asp Thr Thr Tyr Asn Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Met Gly Thr Thr Leu Glu Ala Pro Leu Asp Tyr Trp Gly Gln
            100                 105                 110

Gly Thr Leu Val Thr Val Ser Ser Ser Gly Gly Gly Gly Glu Ile Val
```

```
                  115                 120                 125
Leu Thr Gln Ser Pro Ala Thr Leu Ser Leu Ser Pro Gly Glu Arg Ala
            130                 135                 140
Thr Leu Ser Cys Ser Ala Arg Ser Ser Val Ser Tyr Leu Tyr Trp Tyr
145                 150                 155                 160
Gln Gln Lys Pro Gly Gln Ala Pro Arg Leu Leu Ile Tyr Asp Thr Ser
                165                 170                 175
Asn Leu Ala Ser Gly Ile Pro Asp Arg Phe Ser Gly Ser Gly Ser Gly
            180                 185                 190
Thr Asp Phe Thr Leu Thr Ile Ser Arg Leu Glu Pro Glu Asp Ala Ala
                195                 200                 205
Val Tyr Tyr Cys Gln Gln Trp Ser Asp Tyr Pro Leu Thr Phe Gly Gly
            210                 215                 220
Gly Thr Lys Leu Glu Ile Lys Gly Gly Cys
225                 230

<210> SEQ ID NO 16
<211> LENGTH: 237
<212> TYPE: PRT
<213> ORGANISM: Artificial Sequence
<220> FEATURE:
<223> OTHER INFORMATION: cys-diabody

<400> SEQUENCE: 16

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Ser Phe Ala Asn Tyr
            20                  25                  30
Trp Met His Trp Val Arg Gln Ala Pro Gly Gln Arg Leu Glu Trp Ile
        35                  40                  45
Gly Ala Leu Tyr Pro Gly Asn Val Asp Thr Thr Tyr Asn Gln Lys Phe
    50                  55                  60
Gln Gly Arg Val Thr Ile Thr Arg Asp Thr Ser Ala Ser Thr Ala Tyr
65                  70                  75                  80
Met Glu Leu Ser Ser Leu Arg Ser Glu Asp Thr Ala Val Tyr Tyr Cys
                85                  90                  95
Thr Arg Met Gly Thr Thr Leu Glu Ala Pro Leu Asp Tyr Trp Gly Gln
            100                 105                 110
Gly Thr Leu Val Thr Val Ser Ser Gly Gly Gly Glu Ile Val
        115                 120                 125
Leu Thr Gln Ser Pro Ala Thr Leu Ser Leu Ser Pro Gly Glu Arg Ala
            130                 135                 140
Thr Leu Ser Cys Ser Ala Arg Ser Ser Val Ser Tyr Leu Tyr Trp Tyr
145                 150                 155                 160
Gln Gln Lys Pro Gly Gln Ala Pro Arg Leu Leu Ile Tyr Asp Thr Ser
                165                 170                 175
Asn Leu Ala Ser Gly Ile Pro Asp Arg Phe Ser Gly Ser Gly Ser Gly
            180                 185                 190
Thr Asp Phe Thr Leu Thr Ile Ser Arg Leu Glu Pro Glu Asp Ala Ala
                195                 200                 205
Val Tyr Tyr Cys Gln Gln Trp Ser Asp Tyr Pro Leu Thr Phe Gly Gly
            210                 215                 220
Gly Thr Lys Leu Glu Ile Lys Gly Gly Cys Pro Pro Cys
225                 230                 235
```

```
<210> SEQ ID NO 17
<211> LENGTH: 240
<212> TYPE: PRT
<213> ORGANISM: Artificial Sequence
<220> FEATURE:
<223> OTHER INFORMATION: cys-diabody

<400> SEQUENCE: 17

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Ala Asn Tyr
            20                  25                  30

Trp Met His Trp Val Arg Gln Ala Pro Gly Gln Arg Leu Glu Trp Ile
        35                  40                  45

Gly Ala Leu Tyr Pro Gly Asn Val Asp Thr Thr Tyr Asn Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Met Gly Thr Thr Leu Glu Ala Pro Leu Asp Tyr Trp Gly Gln
            100                 105                 110

Gly Thr Leu Val Thr Val Ser Ser Gly Gly Gly Glu Ile Val
        115                 120                 125

Leu Thr Gln Ser Pro Ala Thr Leu Ser Leu Ser Pro Gly Glu Arg Ala
    130                 135                 140

Thr Leu Ser Cys Ser Ala Arg Ser Ser Val Ser Tyr Leu Tyr Trp Tyr
145                 150                 155                 160

Gln Gln Lys Pro Gly Gln Ala Pro Arg Leu Leu Ile Tyr Asp Thr Ser
                165                 170                 175

Asn Leu Ala Ser Gly Ile Pro Asp Arg Phe Ser Gly Ser Gly Ser Gly
            180                 185                 190

Thr Asp Phe Thr Leu Thr Ile Ser Arg Leu Glu Pro Glu Asp Ala Ala
        195                 200                 205

Val Tyr Tyr Cys Gln Gln Trp Ser Asp Tyr Pro Leu Thr Phe Gly Gly
    210                 215                 220

Gly Thr Lys Leu Glu Ile Lys Gly Gly Cys Pro Pro Cys Pro Pro Cys
225                 230                 235                 240

<210> SEQ ID NO 18
<211> LENGTH: 243
<212> TYPE: PRT
<213> ORGANISM: Artificial Sequence
<220> FEATURE:
<223> OTHER INFORMATION: cys-diabody

<400> SEQUENCE: 18

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Ala Asn Tyr
            20                  25                  30

Trp Met His Trp Val Arg Gln Ala Pro Gly Gln Arg Leu Glu Trp Ile
        35                  40                  45

Gly Ala Leu Tyr Pro Gly Asn Val Asp Thr Thr Tyr Asn Gln Lys Phe
    50                  55                  60

Gln Gly Arg Val Thr Ile Thr Arg Asp Thr Ser Ala Ser Thr Ala Tyr
65                  70                  75                  80
```

Met Glu Leu Ser Ser Leu Arg Ser Glu Asp Thr Ala Val Tyr Tyr Cys
                85                  90                  95

Thr Arg Met Gly Thr Thr Leu Glu Ala Pro Leu Asp Tyr Trp Gly Gln
            100                 105                 110

Gly Thr Leu Val Thr Val Ser Ser Gly Gly Gly Gly Glu Ile Val
        115                 120                 125

Leu Thr Gln Ser Pro Ala Thr Leu Ser Leu Ser Pro Gly Glu Arg Ala
        130                 135                 140

Thr Leu Ser Cys Ser Ala Arg Ser Ser Val Ser Tyr Leu Tyr Trp Tyr
145                 150                 155                 160

Gln Gln Lys Pro Gly Gln Ala Pro Arg Leu Leu Ile Tyr Asp Thr Ser
                165                 170                 175

Asn Leu Ala Ser Gly Ile Pro Asp Arg Phe Ser Gly Ser Gly Ser Gly
            180                 185                 190

Thr Asp Phe Thr Leu Thr Ile Ser Arg Leu Glu Pro Glu Asp Ala Ala
        195                 200                 205

Val Tyr Tyr Cys Gln Gln Trp Ser Asp Tyr Pro Leu Thr Phe Gly Gly
        210                 215                 220

Gly Thr Lys Leu Glu Ile Lys Gly Gly Cys Pro Pro Cys Pro Pro Cys
225                 230                 235                 240

Pro Pro Cys

<210> SEQ ID NO 19

<400> SEQUENCE: 19

000

<210> SEQ ID NO 20

<400> SEQUENCE: 20

000

<210> SEQ ID NO 21

<400> SEQUENCE: 21

000

<210> SEQ ID NO 22
<211> LENGTH: 20
<212> TYPE: PRT
<213> ORGANISM: Artificial Sequence
<220> FEATURE:
<223> OTHER INFORMATION: signal peptide

<400> SEQUENCE: 22

Met Glu Thr Asp Thr Leu Leu Leu Trp Val Leu Leu Leu Trp Val Pro
1               5                   10                  15

Gly Ser Thr Gly
            20

<210> SEQ ID NO 23
<211> LENGTH: 20
<212> TYPE: PRT
<213> ORGANISM: Artificial Sequence
<220> FEATURE:
<223> OTHER INFORMATION: signal peptide

<400> SEQUENCE: 23

```
Met Glu Thr Asp Thr Leu Leu Leu Trp Val Leu Leu Leu Trp Val Pro
1               5                   10                  15

Gly Ser Thr Gly
            20

<210> SEQ ID NO 24
<211> LENGTH: 20
<212> TYPE: PRT
<213> ORGANISM: Artificial Sequence
<220> FEATURE:
<223> OTHER INFORMATION: signal peptide

<400> SEQUENCE: 24

Met Glu Thr Asp Thr Leu Leu Leu Trp Val Leu Leu Leu Trp Val Pro
1               5                   10                  15

Gly Ser Thr Gly
            20

<210> SEQ ID NO 25
<211> LENGTH: 20
<212> TYPE: PRT
<213> ORGANISM: Artificial Sequence
<220> FEATURE:
<223> OTHER INFORMATION: signal peptide

<400> SEQUENCE: 25

Met Glu Thr Asp Thr Leu Leu Leu Trp Val Leu Leu Leu Trp Val Pro
1               5                   10                  15

Gly Ser Thr Gly
            20

<210> SEQ ID NO 26
<211> LENGTH: 20
<212> TYPE: PRT
<213> ORGANISM: Artificial Sequence
<220> FEATURE:
<223> OTHER INFORMATION: signal peptide

<400> SEQUENCE: 26

Met Glu Thr Asp Thr Leu Leu Leu Trp Val Leu Leu Leu Trp Val Pro
1               5                   10                  15

Gly Ser Thr Gly
            20

<210> SEQ ID NO 27
<211> LENGTH: 20
<212> TYPE: PRT
<213> ORGANISM: Artificial Sequence
<220> FEATURE:
<223> OTHER INFORMATION: signal peptide

<400> SEQUENCE: 27

Met Glu Thr Asp Thr Leu Leu Leu Trp Val Leu Leu Leu Trp Val Pro
1               5                   10                  15

Gly Ser Thr Gly
            20

<210> SEQ ID NO 28
<211> LENGTH: 20
<212> TYPE: PRT
<213> ORGANISM: Artificial Sequence
<220> FEATURE:
<223> OTHER INFORMATION: signal peptide

<400> SEQUENCE: 28
```

```
Met Glu Thr Asp Thr Leu Leu Leu Trp Val Leu Leu Leu Trp Val Pro
1               5                   10                  15

Gly Ser Thr Gly
            20

<210> SEQ ID NO 29
<211> LENGTH: 20
<212> TYPE: PRT
<213> ORGANISM: Artificial Sequence
<220> FEATURE:
<223> OTHER INFORMATION: signal peptide

<400> SEQUENCE: 29

Met Glu Thr Asp Thr Leu Leu Leu Trp Val Leu Leu Leu Trp Val Pro
1               5                   10                  15

Gly Ser Thr Gly
            20

<210> SEQ ID NO 30
<211> LENGTH: 20
<212> TYPE: PRT
<213> ORGANISM: Artificial Sequence
<220> FEATURE:
<223> OTHER INFORMATION: signal peptide

<400> SEQUENCE: 30

Met Glu Thr Asp Thr Leu Leu Leu Trp Val Leu Leu Leu Trp Val Pro
1               5                   10                  15

Gly Ser Thr Gly
            20

<210> SEQ ID NO 31
<211> LENGTH: 20
<212> TYPE: PRT
<213> ORGANISM: Artificial Sequence
<220> FEATURE:
<223> OTHER INFORMATION: signal peptide

<400> SEQUENCE: 31

Met Glu Thr Asp Thr Leu Leu Leu Trp Val Leu Leu Leu Trp Val Pro
1               5                   10                  15

Gly Ser Thr Gly
            20

<210> SEQ ID NO 32
<211> LENGTH: 20
<212> TYPE: PRT
<213> ORGANISM: Artificial Sequence
<220> FEATURE:
<223> OTHER INFORMATION: signal peptide

<400> SEQUENCE: 32

Met Glu Thr Asp Thr Leu Leu Leu Trp Val Leu Leu Leu Trp Val Pro
1               5                   10                  15

Gly Ser Thr Gly
            20

<210> SEQ ID NO 33
<211> LENGTH: 20
<212> TYPE: PRT
<213> ORGANISM: Artificial Sequence
<220> FEATURE:
<223> OTHER INFORMATION: signal peptide
```

```
<400> SEQUENCE: 33

Met Glu Thr Asp Thr Leu Leu Leu Trp Val Leu Leu Leu Trp Val Pro
1               5                   10                  15

Gly Ser Thr Gly
            20

<210> SEQ ID NO 34
<211> LENGTH: 28
<212> TYPE: PRT
<213> ORGANISM: Artificial Sequence
<220> FEATURE:
<223> OTHER INFORMATION: hinge

<400> SEQUENCE: 34

Glu Pro Lys Ser Ser Asp Lys Thr His Thr Cys Pro Pro Cys Pro Pro
1               5                   10                  15

Cys Gly Gly Gly Ser Ser Gly Gly Gly Ser Gly Gly
            20                  25

<210> SEQ ID NO 35
<211> LENGTH: 31
<212> TYPE: PRT
<213> ORGANISM: Artificial Sequence
<220> FEATURE:
<223> OTHER INFORMATION: hinge

<400> SEQUENCE: 35

Glu Pro Lys Ser Ser Asp Lys Thr His Thr Cys Pro Pro Cys Pro Pro
1               5                   10                  15

Cys Pro Pro Cys Gly Gly Gly Ser Ser Gly Gly Gly Ser Gly Gly
            20                  25                  30

<210> SEQ ID NO 36
<211> LENGTH: 28
<212> TYPE: PRT
<213> ORGANISM: Artificial Sequence
<220> FEATURE:
<223> OTHER INFORMATION: hinge

<400> SEQUENCE: 36

Glu Pro Lys Ser Ser Asp Lys Thr His Thr Cys Pro Pro Cys Pro Pro
1               5                   10                  15

Cys Gly Gly Gly Ser Ser Gly Gly Gly Ser Gly Gly
            20                  25

<210> SEQ ID NO 37
<211> LENGTH: 31
<212> TYPE: PRT
<213> ORGANISM: Artificial Sequence
<220> FEATURE:
<223> OTHER INFORMATION: hinge

<400> SEQUENCE: 37

Glu Pro Lys Ser Ser Asp Lys Thr His Thr Cys Pro Pro Cys Pro Pro
1               5                   10                  15

Cys Pro Pro Cys Gly Gly Gly Ser Ser Gly Gly Gly Ser Gly Gly
            20                  25                  30

<210> SEQ ID NO 38
<211> LENGTH: 62
<212> TYPE: PRT
<213> ORGANISM: Artificial Sequence
<220> FEATURE:
<223> OTHER INFORMATION: MAX16H5
```

<400> SEQUENCE: 38

Glu Val Gln Leu Gln Gln Ser Gly Thr Val Leu Ala Arg Pro Gly Ala
1               5                   10                  15

Ser Val Gln Met Ser Cys Lys Ala Ser Gly Tyr Ser Phe Ala Asn Tyr
            20                  25                  30

Trp Met His Trp Val Lys Gln Arg Pro Gly Gln Gly Leu Gln Trp Ile
        35                  40                  45

Gly Ala Leu Tyr Pro Gly Asn Val Asp Thr Thr Tyr Asn Gln
    50                  55                  60

<210> SEQ ID NO 39
<211> LENGTH: 62
<212> TYPE: PRT
<213> ORGANISM: Homo sapiens

<400> SEQUENCE: 39

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln
    50                  55                  60

<210> SEQ ID NO 40
<211> LENGTH: 62
<212> TYPE: PRT
<213> ORGANISM: Artificial Sequence
<220> FEATURE:
<223> OTHER INFORMATION: IAB41

<400> SEQUENCE: 40

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Ala Asn Tyr
            20                  25                  30

Trp Met His Trp Val Arg Gln Ala Pro Gly Gln Arg Leu Glu Trp Ile
        35                  40                  45

Gly Ala Leu Tyr Pro Gly Asn Val Asp Thr Thr Tyr Asn Gln
    50                  55                  60

<210> SEQ ID NO 41
<211> LENGTH: 60
<212> TYPE: PRT
<213> ORGANISM: Artificial Sequence
<220> FEATURE:
<223> OTHER INFORMATION: MAX16H5

<400> SEQUENCE: 41

Gln Ile Val Leu Thr Gln Ser Pro Ala Ile Met Ser Ala Ser Pro Gly
1               5                   10                  15

Glu Lys Val Ala Met Thr Cys Ser Ala Arg Ser Ser Val Ser Tyr Leu
            20                  25                  30

Tyr Trp Tyr Gln Gln Lys Pro Gly Ser Ser Pro Arg Leu Leu Ile Tyr
        35                  40                  45

Asp Thr Ser Asn Leu Ala Ser Gly Val Pro Val Arg
    50                  55                  60

```
<210> SEQ ID NO 42
<211> LENGTH: 43
<212> TYPE: PRT
<213> ORGANISM: Homo sapiens

<400> SEQUENCE: 42

Glu Ile Val Leu Thr Gln Ser Pro Ala Thr Leu Ser Leu Ser Pro Gly
1               5                   10                  15

Glu Arg Ala Thr Leu Ser Cys Trp Tyr Gln Gln Lys Pro Gly Leu Ala
            20                  25                  30

Pro Arg Leu Leu Ile Tyr Gly Ile Pro Asp Arg
        35                  40

<210> SEQ ID NO 43
<211> LENGTH: 60
<212> TYPE: PRT
<213> ORGANISM: Artificial Sequence
<220> FEATURE:
<223> OTHER INFORMATION: IAB41

<400> SEQUENCE: 43

Glu Ile Val Leu Thr Gln Ser Pro Ala Thr Leu Ser Leu Ser Pro Gly
1               5                   10                  15

Glu Arg Ala Thr Leu Ser Cys Ser Ala Arg Ser Ser Val Ser Tyr Leu
            20                  25                  30

Tyr Trp Tyr Gln Gln Lys Pro Gly Gln Ala Pro Arg Leu Leu Ile Tyr
        35                  40                  45

Asp Thr Ser Asn Leu Ala Ser Gly Ile Pro Asp Arg
    50                  55                  60

<210> SEQ ID NO 44
<211> LENGTH: 433
<212> TYPE: PRT
<213> ORGANISM: Homo sapiens

<400> SEQUENCE: 44

Lys Lys Val Val Leu Gly Lys Lys Gly Asp Thr Val Glu Leu Thr Cys
1               5                   10                  15

Thr Ala Ser Gln Lys Lys Ser Ile Gln Phe His Trp Lys Asn Ser Asn
            20                  25                  30

Gln Ile Lys Ile Leu Gly Asn Gln Gly Ser Phe Leu Thr Lys Gly Pro
        35                  40                  45

Ser Lys Leu Asn Asp Arg Ala Asp Ser Arg Arg Ser Leu Trp Asp Gln
    50                  55                  60

Gly Asn Phe Pro Leu Ile Ile Lys Asn Leu Lys Ile Glu Asp Ser Asp
65                  70                  75                  80

Thr Tyr Ile Cys Glu Val Glu Asp Gln Lys Glu Glu Val Gln Leu Leu
                85                  90                  95

Val Phe Gly Leu Thr Ala Asn Ser Asp Thr His Leu Leu Gln Gly Gln
            100                 105                 110

Ser Leu Thr Leu Thr Leu Glu Ser Pro Pro Gly Ser Ser Pro Ser Val
        115                 120                 125

Gln Cys Arg Ser Pro Arg Gly Lys Asn Ile Gln Gly Gly Lys Thr Leu
    130                 135                 140

Ser Val Ser Gln Leu Glu Leu Gln Asp Ser Gly Thr Trp Thr Cys Thr
145                 150                 155                 160

Val Leu Gln Asn Gln Lys Lys Val Glu Phe Lys Ile Asp Ile Val Val
                165                 170                 175
```

```
Leu Ala Phe Gln Lys Ala Ser Ser Ile Val Tyr Lys Lys Glu Gly Glu
            180                 185                 190

Gln Val Glu Phe Ser Phe Pro Leu Ala Phe Thr Val Glu Lys Leu Thr
            195                 200                 205

Gly Ser Gly Glu Leu Trp Trp Gln Ala Glu Arg Ala Ser Ser Ser Lys
210                 215                 220

Ser Trp Ile Thr Phe Asp Leu Lys Asn Lys Glu Val Ser Val Lys Arg
225                 230                 235                 240

Val Thr Gln Asp Pro Lys Leu Gln Met Gly Lys Lys Leu Pro Leu His
            245                 250                 255

Leu Thr Leu Pro Gln Ala Leu Pro Gln Tyr Ala Gly Ser Gly Asn Leu
            260                 265                 270

Thr Leu Ala Leu Glu Ala Lys Thr Gly Lys Leu His Gln Glu Val Asn
            275                 280                 285

Leu Val Val Met Arg Ala Thr Gln Leu Gln Lys Asn Leu Thr Cys Glu
            290                 295                 300

Val Trp Gly Pro Thr Ser Pro Lys Leu Met Leu Ser Leu Lys Leu Glu
305                 310                 315                 320

Asn Lys Glu Ala Lys Val Ser Lys Arg Glu Lys Ala Val Trp Val Leu
            325                 330                 335

Asn Pro Glu Ala Gly Met Trp Gln Cys Leu Leu Ser Asp Ser Gly Gln
            340                 345                 350

Val Leu Leu Glu Ser Asn Ile Lys Val Leu Pro Thr Trp Ser Thr Pro
            355                 360                 365

Val Gln Pro Met Ala Leu Ile Val Leu Gly Gly Val Ala Gly Leu Leu
            370                 375                 380

Leu Phe Ile Gly Leu Gly Ile Phe Phe Cys Val Arg Cys Arg His Arg
385                 390                 395                 400

Arg Arg Gln Ala Glu Arg Met Ser Gln Ile Lys Arg Leu Leu Ser Glu
            405                 410                 415

Lys Lys Thr Cys Gln Cys Pro His Arg Phe Gln Lys Thr Cys Ser Pro
            420                 425                 430

Ile

<210> SEQ ID NO 45
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 45

Lys Ala Ser Gly Tyr Ser Phe Ala Asn Tyr Trp Met His
1               5                   10

<210> SEQ ID NO 46
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 46

Glu Trp Ile Gly Ala Leu Tyr Pro Gly Asn Val Asp Thr Thr
1               5                   10

<210> SEQ ID NO 47
```

```
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 47

Thr Arg Met Gly Thr Thr Leu Glu Ala Pro Leu Asp Tyr
1               5                   10

<210> SEQ ID NO 48
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 48

Ser Ala Arg Ser Ser Val Ser Tyr Leu Tyr
1               5                   10

<210> SEQ ID NO 49
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 49

Tyr Asp Thr Ser Asn Leu Ala Ser
1               5

<210> SEQ ID NO 50
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 50

Gln Gln Trp Ser Asp Tyr Pro Leu Thr
1               5
```